(12) United States Patent
Wardleworth et al.

(10) Patent No.: US 6,809,098 B2
(45) Date of Patent: Oct. 26, 2004

(54) COMPOUNDS

(75) Inventors: Michael Wardleworth, Chesire (GB); Alexander Graham Dossetter, Chesire (GB); Christopher Thomas Halsall, Lancashire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/227,193

(22) Filed: Aug. 21, 2002

(65) Prior Publication Data

US 2003/0171354 A1 Sep. 11, 2003

Related U.S. Application Data

(63) Continuation-in-part of application No. PCT/GB02/00679, filed on Feb. 15, 2002.

(51) Int. Cl.[7] ................ C07D 401/12; C07D 209/16; C07D 417/12; A61K 31/404; A61P 5/02

(52) U.S. Cl. ................ 514/235.2; 546/277.4; 546/201; 546/194; 546/187; 514/339; 514/397; 514/254.09; 514/323; 514/414; 514/383; 514/365; 514/415; 514/318; 514/316; 548/312.1; 548/467; 548/262.8; 548/181; 548/505; 544/373; 544/143

(58) Field of Search .............. 546/277.4, 201, 546/194, 187; 514/339, 397, 254.9, 323, 414, 383, 365, 415, 235.2, 318, 316; 548/312.1, 467, 262.8, 181, 505; 544/373, 143

(56) References Cited

FOREIGN PATENT DOCUMENTS

| WO | WO 97/21435 A1 | 6/1997 |
|---|---|---|
| WO | WO 97/21703 A1 | 6/1997 |
| WO | WO 97/21704 A1 | 6/1997 |
| WO | WO 97/21707 A1 | 6/1997 |
| WO | WO 98/55116 A1 | 12/1998 |
| WO | WO 98/55119 A1 | 12/1998 |
| WO | WO 98/55123 A1 | 12/1998 |
| WO | WO 98/55470 A1 | 12/1998 |
| WO | WO 98/55479 A1 | 12/1998 |
| WO | WO 99/21553 A1 | 5/1999 |
| WO | WO 99/21557 A1 | 5/1999 |
| WO | WO 99/41251 A1 | 8/1999 |
| WO | WO 99/41252 A1 | 8/1999 |
| WO | WO 99/51231 A1 | 10/1999 |
| WO | WO 99/51232 A1 | 10/1999 |
| WO | WO 99/51233 A1 | 10/1999 |
| WO | WO 99/51234 A1 | 10/1999 |
| WO | WO 99/51595 A1 | 10/1999 |
| WO | WO 99/51596 A1 | 10/1999 |
| WO | WO 00/04013 A1 | 1/2000 |
| WO | WO 00/53178 A1 | 9/2000 |
| WO | WO 00/53179 A1 | 9/2000 |
| WO | WO 00/53180 A1 | 9/2000 |
| WO | WO 00/53181 A1 | 9/2000 |
| WO | WO 00/53185 A1 | 9/2000 |
| WO | WO 00/53602 A1 | 9/2000 |
| WO | WO 00/69433 A1 | 11/2000 |

OTHER PUBLICATIONS

Ashton, W. et al, Substituted Indole–5–carboxamides and –acetamides as Potent Nonpeptide GnRH Receptor Antagonists, Bioorganic & Medicinal Chemistry Letters 11: 1723–1726 (2001).

Ashton, W. et al, Potent Nonpeptide GnRH Receptor Antagonists Derived from Substituted Indole–5–carboxamides and –acetamides Bearing a Pyridine Side–Chain Terminus, Bioorganic & Medicinal Chemistry Letters 11: 1727–1731 (2001).

Ashton, W. et al, Orally Bioavailable, Indole–Based Nonpeptide GnRH Receptor Antagonists with High Potency and Functional Activity, Bioorganic & Medicinal Chemistry Letters 11:2597–2602 (2001).

Chu, L. et al, SAR Studies of Novel 5–Substituted 2–Arylindoles as Nonpeptidyl GnRH Receptor Antagonists, Bioorganic & Medicinal Chemistry Letters 11: 515–517 (2001).

Chu, L. et al, Initial Structure–Activity Relationship of a Novel Class of Nonpeptidyl GnRH Receptor Antagonists: 2–Arylindoles, Bioorganic & Medicinal Chemistry Letters 11: 509–513 (2001).

Freidinger, R., Nonpeptidic ligands for peptide and protein receptors, Current Opinion in Chemical Biology 3: 395–406 (1999).

Lin, P. et al, Heterocyclic Derivatives of 2–(3,5–Dimethylphenyl) tryptamine as GnRH Receptor Antagonists, Bioorganic & Medicinal Chemistry Letters 11: 1077–1080 (2001).

Lin, P. et al, 2–(3,5–Dimethylphenyl) tryptamine Derivatives That Bind to the GnRH Receptor, Bioorganic & Medicinal Chemistry Letters 11: 1073–1076 (2001).

(List continued on next page.)

Primary Examiner—Mukund J. Shah
Assistant Examiner—Hong Liu
(74) Attorney, Agent, or Firm—Ropes & Gray LLP

(57) ABSTRACT

The present invention relates to compounds of formula I which are antagonists of gonadotropin releasing hormone (GnRH) activity. The invention also relates to pharmaceutical formulations, the use of a compound of the present invention in the manufacture of a medicament, a method of therapeutic treatment using such a compound and processes for producing the compounds.

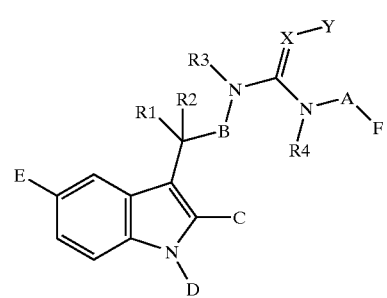

13 Claims, No Drawings

OTHER PUBLICATIONS

Goulet, M., Gonadotropin Releasing Hormone Antagonists, Annual Reports in Medicinal Chemistry 30: 169–178 (1995).

Simeone, J. et al, Synthesis of chiral β–methyl tryptamine–derived GnRH antagonists, Tetrahedron Letters 42: 6459–6461 (2001).

Ujjainwalla, F. et al, Total syntheses of 6– and 7–azaindole derived GnRH antagonists, Tetrahedron Letters 42: 6459–6461 (2001).

Walsh, T. et al, A convergent synthesis of (S)–β–methyl–2–aryltryptamine based gonadotropin releasing hormone antagonists, Tetrahedron 57: 5233–5241 (2001).

Young, J. et al, 2–Arylindoles as Gonadotropin Releasing Hormone (GnRH) Antagonists: Optimization of the Tryptamine Side Chain, Bioorganic & Medicinal Chemistry Letters 12: 827–832 (2002).

Simeone et al., "Modification of the Pyridine Moiety of Non–peptidyl Indole GnRH Receptor Antagonists," Bioorganic & Medicinal Chemistry Letters 12:3329–3332 (2002).

Ujjainwalla et al., "Total synthesis of 6– and 7–azaindole Derived GnRH antagonists," Tetrahedron Letters 42:6441–6445 (2001).

Gibbs et al., "Pharmaceutical Research in Molecular Oncology," Cell 79:193–198 (1994).

COMPOUNDS

This application is a continuation-in-part of PCT application Ser. No. PCT/GB02/00679, filed on Feb. 15, 2002, which claims priority from Swedish Application No. 0100566-9, filed on Feb. 20, 2001, the specifications of each of which are hereby incorporated by reference in their entirety. PCT Application PCT/GB02100679 was published under PCT Article 21(2) in English.

The present invention relates to compounds which are antagonists of gonadotropin releasing hormone (GnRH) activity. The invention also relates to pharmaceutical formulations, the use of a compound of the present invention in the manufacture of a medicament, a method of therapeutic treatment using such a compound and processes for producing the compounds.

BACKGROUND TO THE INVENTION

Gonadotropin releasing hormone (GnRH) is a decapeptide that is secreted by the hypothalamus into the hypophyseal portal circulation in response to neural and/or chemical stimuli, causing the biosynthesis and release of luteinizing hormone (LH) and follicle-stimulating hormone (FSH) by the pituitary. GnRH is also known by other names, including gonadoliberin, LH releasing hormone (LHRH), FSH releasing hormone (FSH RH) and LH/FSH releasing factor (LH/FSH RF).

GnRH plays an important role in regulating the action of LH and FSH (by regulation of their levels), and thus has a role in regulating the levels of gonadal steroids in both sexes, including the sex hormones progesterone, oestrogens and androgens. More discussion of GnRH can be found in WO 98/5519 and WO 97/14697, the disclosures of which are incorporated herein by reference.

It is believed that several diseases would benefit from the regulation of GnRH activity, in particular by antagonising such activity. These include sex hormone related conditions such as sex hormone dependent cancer, benign prostatic hypertrophy and myoma of the uterus. Examples of sex hormone dependent cancers are prostatic cancer, uterine cancer, breast cancer and pituitary gonadotrophe adenoma.

The following disclose compounds purported to act as GnRH antagonists: WO 00/04013, WO 99/41252, WO 99/41251, WO 98/55123, WO 97/21704, WO 97/21703, WO 97/21707, WO 97/21435, WO 97/44041, WO 98/55119, WO 99/51596 and WO 97/14697.

It would be desirable to provide further compounds, such compounds being GnRH antagonists.

SUMMARY OF THE INVENTION

The present invention accordingly provides a compound of formula I or a pharmaceutically acceptable salt or solvate thereof

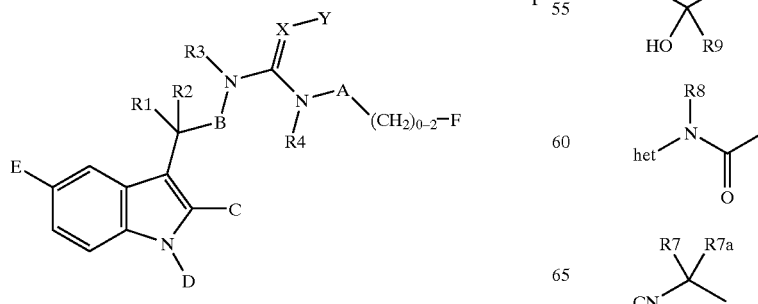

I

For A, either:

(i) A represents a single bond; optionally substituted C1 to C8 alkylene; a C2 to C12 group having at least one alkene double bond; a 3- to 8-membered heterocyclic ring containing from 1 to 4 heteroatoms independently selected from O, N and S or —R—Ar—R'—, where R and R' are independently selected from a bond, optionally substituted C1 to C8 alkylene and a C2 to C12 group having at least one alkene double bond; and Ar represents optionally substituted aryl; or (ii) the structure N—A(—R4) represents a 3- to 8-membered heterocyclic ring optionally containing from 1 to 3 further heteroatoms independently selected from O, N and S, N—A(—R4) being optionally substituted;

B represents a bond or optionally substituted C1 to C5 alkylene;

C represents a mono- or bi-cyclic aromatic ring structure optionally having at least one substituent selected from CN; NR5R6; an optionally substituted C1 to C8 alkyl; optionally substituted C1 to C8 alkoxy; halogen;

D represents hydrogen; optionally substituted C1 to C8 alkyl; or $(CH_2)_b$—R, wherein R represents C3 to C8 cycloalkyl;

E is selected from an optionally substituted 3- to 8-membered heterocyclic ring containing is from 1 to 4 heteroatoms independently selected from O, N and S; II; III; IV; V; VI; VII, VIIa, VIIb, VIIc, and VIId,

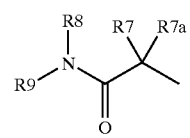

II

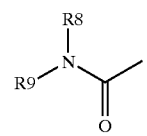

III

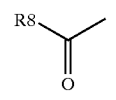

IV

V

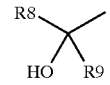

VI

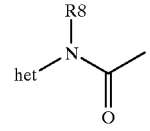

VII

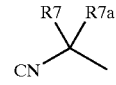

VIIa

VIIb

R9—O—C(R7)(R7a)—C(=O)—O—

VIIc

R9—N(R8)—C(R7)(R7a)—C(=O)—N—

VIId

C₁₋₄alkyl\
    C—
C₁₋₄alkyl/ \H wherein het represents an optionally substituted 3- to 8-membered heterocyclic ring containing from 1 to 4 heteroatoms independently selected from O, N and S;

F is optionally substituted and represents phenyl or a 3- to 8-membered heterocyclic ring containing from 1 to 4 heteroatoms independently selected from O, N and S;

For X and V, either:
  (iii) X represents N and Y represents CN or H; or X represents CH and Y represents NO₂; or
  (iv) X—Y represents O;

For R1 and R2, either:
  (v) R1 and R2 are independently selected from hydrogen and optionally substituted C1 to C8 alkyl; or
  (vi) R1 and R2 together represent carbonyl; or
  (vii)

R1—B—N—R3 represents an optionally substituted 3- to 8-membered heterocyclic ring containing from 1 to 3 further heteroatoms independently selected from O, N and S, and R2 meets the definition in option (v);

is R3 meets the definition in option (vii) or represents hydrogen or optionally substituted C1 to C8 alkyl;

R4 meets the definition in option (ii) or represents hydrogen or optionally substituted C1 to C8 alkyl;

R5 and R6 are independently selected from H; optionally substituted C1 to C8 alkyl and optionally substituted aryl;

For R7 and R7a, either:
  (viii) R7 and R7a are independently selected from H or optionally substituted C1 to C8 alkyl; or
  (ix)

R7—◁—R7a represents an optionally substituted 3 to 7-membered cycloalkyl ring;

For R8 and R9, either:
  (x) R8 is selected from H; optionally substituted C1 to C8 alkyl; optionally substituted aryl; —R—Ar, where R represents C1 to C8 alkylene and Ar represents optionally substituted aryl; and optionally substituted 3- to 8-membered heterocyclic ring optionally containing from 1 to 3 further heteroatoms independently selected from O, N and S; and R9 is selected from H; optionally substituted C1 to C8 alkyl and optionally substituted aryl; or
  (xi) wherein E represents structure II or III, NR8(-R9) represents an optionally substituted 3- to 8-membered heterocyclic ring optionally containing from 1 to 3 further heteroatoms independently selected from O, N and S; or
  (xii) wherein E represents structure VI,

R8—▽—R9 represents an optionally substituted 3- to 8-membered heterocyclic ring optionally containing from 1 to 4 heteroatoms independently selected from O, N and S;

b represents zero or an integer from 1 to 6.

In one embodiment, a compound of formula I or a pharmaceutically acceptable salt or solvate thereof is provided, with the proviso that a compound wherein X represents CH, Y represents NO₂, N—A(—R4) meets the definition in option (ii) and F represents optionally substituted phenyl is excluded.

The present invention also provides a pharmaceutical formulation comprising such a compound and a pharmaceutically acceptable diluent or carrier.

Furthermore, the present invention provides the following uses of the compound:
  (a) Use in the manufacture of a medicament, for antagonising gonadotropin releasing hormone activity.
  (b) Use in the manufacture of a medicament for administration to a patient, for reducing the secretion of luteinising hormone by the pituitary gland of the patient.
  (c) Use in the manufacture of a medicament for administration to a patient, for therapeutically treating and/or preventing a sex hormone related condition in the patient.

The present invention also relates to a method of antagonising gonadotropin releasing hormone activity in a patient, comprising administering the compound to the patient.

In addition, the invention provides a process of producing the compound.

DETAILED DESCRIPTION OF THE INVENTION

As discussed above, the present invention provides a compound of formula I or a pharmaceutically acceptable salt or solvate thereof

I

For A, either:
  (i) A represents a single bond; optionally substituted C1 to C8 alkylene (preferably, C1 to C4 alkylene, for example methylene or ethylene); a C2 to C12 (preferably, C2 to C8) group having at least one (eg, 1, 2 or 3) alkene double bond; a 3- to 8-membered heterocyclic ring containing from 1 to 4 heteroatoms independently selected from O, N and S (preferably a saturated monocyclic 5–6 membered heterocyclic ring) or —R—Ar—R'—, where R and R' are independently selected from a bond, optionally substituted C1 to C8 alkylene (preferably, C1 to C4 alkylene, for example methylene or ethylene) and a C2 to C12 (preferably, C2 to C8) group having at least one (eg, 1, 2 or 3) alkene double bond; and Ar represents optionally substituted aryl (eg, optionally substituted phenyl); or (ii) the structure N—A(—R4) represents a 3- to 8-membered heterocyclic ring (preferably, a 5- or 6-membered monocyclic ring) optionally containing from 1 to 3 (eg, 1) further heteroatoms independently selected from O, N and S, N—A(—R4) being optionally substituted.

B represents a bond or optionally substituted C1 to C5 alkylene (preferably, C1 to C4 alkylene, for example methylene or ethylene).

C represents a mono- or bi-cyclic aromatic ring structure (preferably, phenyl, pyridyl or thienyl) optionally having at least one substituent (eg, 1, 2 or 3 substituents) selected from CN; NR5R6; an optionally substituted C1 to C8 alkyl (preferably, C1 to C4 alkyl, eg, methyl); optionally substituted C1 to C8 alkoxy (preferably, C1 to C6 alkoxy, eg, methoxy); halogen (eg, F, Br or Cl).

Preferably, C represents

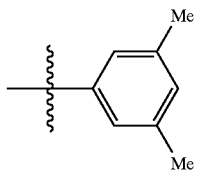

wherein Me represents methyl.

D represents hydrogen; optionally substituted C1 to C8 alkyl (preferably, C1 to C6 alkyl, eg, methyl); or $(CH_2)_b$—R, wherein R represents C3 to C8 cycloalkyl (eg, C3, C4, C5 or C6 cycloalkyl).

E is selected from an optionally substituted 3- to 8-membered heterocyclic ring (preferably, a 5- or 6-membered monocyclic ring) containing from 1 to 4 (eg, 1 or 2) heteroatoms independently selected from O, N and S; II; III; IV; V; VI; VII, VIIa, VIIb, VIIc, and VIId

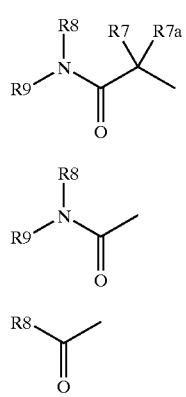

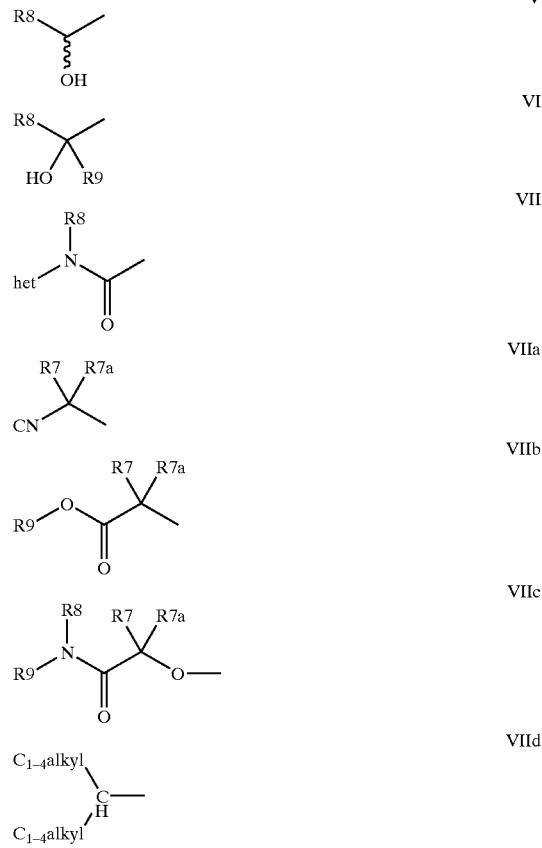

wherein het represents an optionally substituted 3- to 8-membered heterocyclic ring (preferably, a 5- or 6-membered monocyclic ring) containing from 1 to 4 (eg, 1 or 2) heteroatoms independently selected from O, N and S.

Preferably E is selected from a group of formula II, VIIa, VIIb, VIIc or VIId:

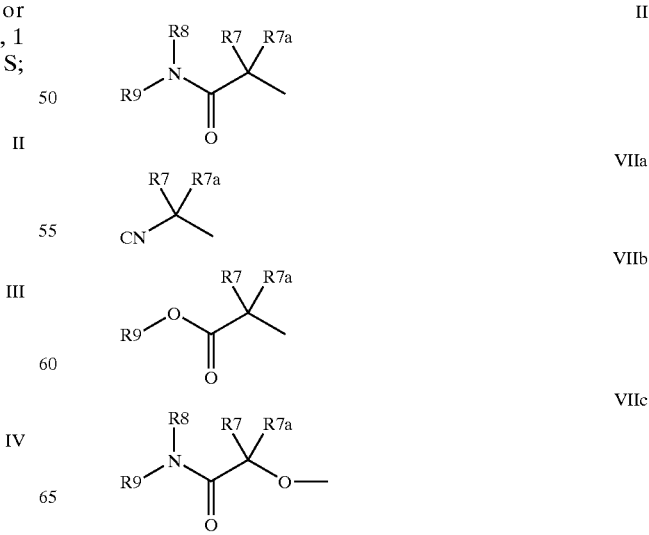

-continued

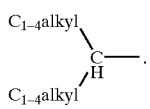
VIId

Further preferably E is selected from one of the following groups:

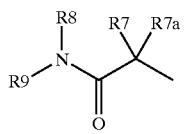
II

VIIa

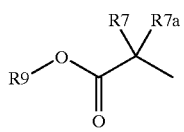
VIIb

Yet further preferably E is selected from one of the following groups:

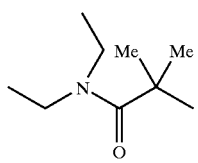 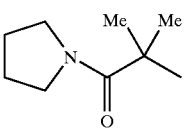

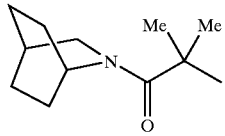 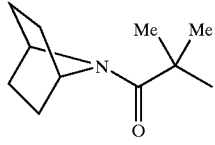

wherein Me represents methyl.

Most preferably E is selected from one of the following groups:

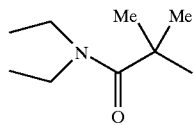 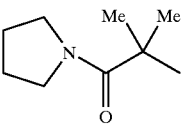

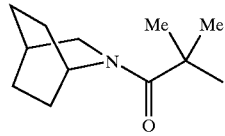 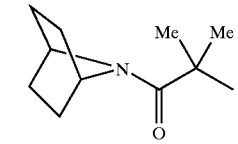

Preferably the group —(CH$_2$)$_{0-2}$—F represents —(CH$_2$)$_{0-1}$—F. Most preferably F is linked to A via a direct bond.

F is optionally substituted and represents phenyl or a 3- to 8-membered heterocyclic ring (preferably, a 5- or 6-membered monocyclic ring) containing from 1 to 4 (eg, 1 or 2) heteroatoms independently selected from O, N and S.

Preferably, F is optionally substituted and represents pyridyl, VIII, IX, X, XI, XII, XIII, XIV or XIVa

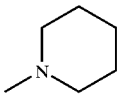
VIII

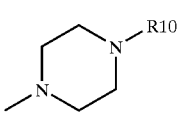
IX

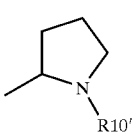
X

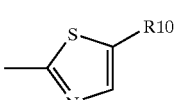
XI

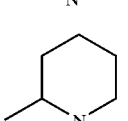
XII

XIII

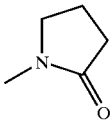
XIV

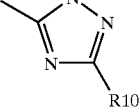
XIVa

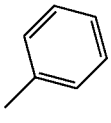

wherein

R10 represents hydrogen; optionally substituted C1 to C8 alkyl (preferably, C1 to C6 alkyl, eg, methyl); OH; halogen (eg, F, Cl or Br); CN; C1 to C8 alkoxy (preferably, C1 to C6 alkoxy, eg, methoxy), or CF$_3$; and R10' represents hydrogen or optionally substituted C1 to C8 alkyl (preferably, C1 to C6 alkyl, eg, methyl).

For X and Y, either:

(iii) X represents N and Y represents CN or H; or X represents CH and Y represents NO$_2$; or (iv) X—Y represents O.

For R1 and R2, either:

(v) R1 and R2 are independently selected from hydrogen and optionally substituted C1 to C8 alkyl (preferably, C1 to C6 alkyl, eg, methyl); or (vi) R1 and R2 together represent carbonyl; or (vii)

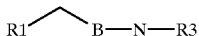

represents an optionally substituted 3- to 8-membered heterocyclic ring (preferably, a 5- or 6-membered monocyclic ring) containing from 1 to 3 (eg, 1 or 2) further heteroatoms independently selected from O, N and S, and R2 meets the definition in option (v).

In one embodiment, R1 and R2 each represent H and B represents C1 alkylene.

R3 meets the definition in option (vii) or represents hydrogen or optionally substituted C1 to C8 alkyl (preferably, C1 to C6 alkyl, eg, methyl).

R4 meets the definition in option (ii) or represents hydrogen or optionally substituted C1 to C8 alkyl (preferably, C1 to C6 alkyl, eg, methyl).

R5 and R6 are independently selected from H; optionally substituted C1 to C8 alkyl (preferably, C1 to C6 alkyl, eg, methyl); and optionally substituted aryl (eg, phenyl).

For R7 and R7a, either:

(viii) R7 and R7a are independently selected from H or optionally substituted C1 to C8 alkyl (preferably, C1 to C6 alkyl, eg, methyl; in one embodiment R7 and R7a are both methyl); or (ix)

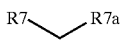

represents an optionally substituted 3 to 7-membered (eg, 3-, 4-, 5- or 6-membered) cycloalkyl ring;

For R8 and R9, either:

(x) R8 is selected from H; optionally substituted C1 to C8 alkyl (preferably, C1 to C6 alkyl, eg, methyl; in one embodiment both R8 and R9 are ethyl); optionally substituted aryl (eg, optionally substituted phenyl); —R—Ar, where R represents C1 to C8 alkylene (preferably, C1 to C6 alkylene, eg, methylene or ethylene) and Ar represents optionally substituted aryl (eg, optionally substituted phenyl); and an optionally substituted 3- to 8-membered heterocyclic ring (preferably, a 5- or 6-membered monocyclic ring) containing from 1 to 3 (eg, 1 or 2) further heteroatoms independently selected from O, N and S; and R9 is selected from H; optionally substituted C1 to C8 alkyl (preferably, C1 to C6 alkyl, eg, methyl) and optionally substituted aryl (eg, optionally substituted phenyl); or (xi) wherein E represents structure II or III, NR8(-R9) represents an optionally substituted 3- to 8-membered heterocyclic ring (preferably, a 5- or 6-membered monocyclic ring) containing from 1 to 3 (eg, 1 or 2) further heteroatoms independently selected from O, N and S; or (xii) wherein E represents structure VI,

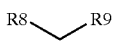

represents an optionally substituted 3- to 8-membered heterocyclic ring (preferably, a 5- or 6-membered monocyclic ring) containing from 1 to 4 (eg, 1 or 2) heteroatoms independently selected from O, N and S.

b represents zero or an integer from 1 to 6.

In the present specification, unless otherwise indicated, an alkyl, alkylene or alkenyl moiety may be linear or branched.

The term "alkylene" refers to the group —CH$_2$—. Thus, C$_8$ alkylene for example is —(CH$_2$)$_8$—

The term "aryl" refers to phenyl or naphthyl.

The term "halo" refers to fluoro, chloro, bromo or iodo.

The term "heterocyclic ring" refers to a 5–10 membered aromatic mono or bicyclic ring or a 5–10 membered saturated or partially saturated mono or bicyclic ring, said aromatic, saturated or partially unsaturated rings containing up to 5 heteroatoms independently selected from nitrogen, oxygen or sulphur, linked via ring carbon atoms or ring nitrogen atoms where a bond from a nitrogen is allowed, for example no bond is possible to the nitrogen of a pyridine ring, but a bond is possible through the 1-nitrogen of a pyrazole ring. Examples of 5- or 6-membered aromatic heterocyclic rings include pyrrolyl, furanyl, imidazolyl, triazolyl, pyrazinyl, pyrimidinyl, pyridazinyl, pyridinyl, isoxazolyl, oxazolyl, 1,2,4 oxadiazolyl, isothiazolyl, thiazolyl and thienyl. A 9 or 10 membered bicyclic aromatic heterocyclic ring is an aromatic bicyclic ring system comprising a 6-membered ring fused to either a 5 membered ring or another 6 membered ring. Examples of 5/6 and 6/6 bicyclic ring systems include benzofuranyl, benzimidazolyl, benzthiophenyl, benzthiazolyl, benzisothiazolyl, benzoxazolyl, benzisoxazolyl, indolyl, pyridoimidazolyl, pyrimidoimidazolyl, quinolinyl, isoquinolinyl, quinoxalinyl, quinazolinyl, phthalazinyl, cinnolinyl and naphthyridinyl. Examples of saturated or partially saturated heterocyclic rings include pyrrolinyl, pyrrolidinyl, morpholinyl, piperidinyl, piperazinyl, dihydropyridinyl and dihydropyrimidinyl.

The term "aromatic ring" refers to a 5–10 membered aromatic mono or bicyclic ring optionally containing up to 5 heteroatoms independently selected from nitrogen, oxygen or sulphur. Examples of such "aromatic rings" include: phenyl, pyrrolyl, furanyl, imidazolyl, triazolyl, pyrazinyl, pyrimidinyl, pyridazinyl, pyridinyl, isoxazolyl, oxazolyl, 1,2,4 oxadiazolyl, isothiazolyl, thiazolyl and thienyl. Preferred aromatic rings include 'phenyl, thienyl and pyridyl.

Where optional substitution is mentioned at various places, this refers to one, two, three or more optional substituents. Unless otherwise indicated above (ie, where a list of optional substituents is provided), each substituent can be independently selected from C1 to C8 alkyl (eg, C2 to C6 alkyl, and most preferably methyl); O(C3 to C8 cycloalkyl), preferably O-cyclopropyl, or O-cyclobutyl or O-cyclopentyl; O(C1 to C6 alkyl), preferably Omethyl or O(C2 to C4 alkyl); halo, preferably Cl or F; CHal$_3$, CHHal$_2$, CH$_2$Hal, OCHal$_3$, OCHHal$_2$ or OCH$_2$Hal, wherein Hal represents halogen (preferably F); CH$_2$OR, NRCOR', NRSO$_2$R' or N—R—R', wherein R and R' independently represent H or C1 to C8 alkyl (preferably methyl or C2 to C6 alkyl or C2 to C4 alkyl), or N—R—R' represents an optionally substituted C3 to C8, preferably C3 to C6, heterocyclic ring optionally containing from 1 to 3 further heteroatoms independently selected from O, N and S; H; or COOR" or COR", R" representing H, optionally substituted phenyl or C1 to C6 alkyl (preferably methyl, ethyl, i-propyl or t-butyl). For optional substitution of the heterocyclic ring represented by N—R—R', at least one (eg, one, two or three) substituents may be provided independently selected from C1 to C6 alkyl (eg, C2 to C4 alkyl, more preferably methyl); phenyl; OCF$_3$; OCHF$_2$; —O(C1-C8 alkyl), preferably —O-methyl, —O-ethyl or —O(C3 to C6 alkyl); —C(O)O(C1–C8 alkyl), preferably —C(O)O-methyl, —C(O)O-ethyl, —C(O)O-tert-butyl or —C(O)O(C3 to C6 alkyl); —C(O)O-phenyl; —O-phenyl; —C(O) (C1–C8 alkyl), preferably —C(O)-methyl, —C(O)-ethyl or —C(O)(C3 to C6 alkyl); —C(O)

OH; —S(C1–C8 alkyl), preferably —S-methyl, —S-ethyl or —S(C3 to C6 alkyl); OH; halogen (eg, F, Cl or Br); NR*R** where R* and R** are independently H or C1 to C6 alkyl (preferably C2 to C4 alkyl, more preferably methyl, most preferably R=R'=methyl); and nitro.

Where optional substitution of a ring is mentioned at various places, this most preferably refers to one, two, three or more substituents selected from C1 to C8 alkyl (eg, C2 to C6 alkyl, and most preferably methyl); —O(C1 to C8 alkyl), preferably —O-methyl, —O-ethyl or —O(C3 to C6 alkyl); halogen (eg, F, Cl or Br); CN; and NO$_2$.

A further preferred group of compounds of the invention comprises a compound of Formula Ia:

Formula Ia

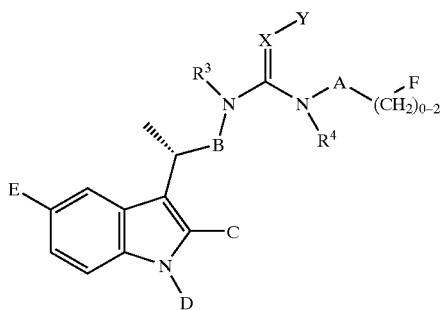

wherein:

A, B, C, D, E, F, X, Y, R$^3$ and R$^4$ are as defined above; or a salt, pro-drug or solvate thereof.

Particularly preferred compounds according to the present invention are:

2-(2-(3,5-dimethylphenyl)-3-{2-[(2-nitro-1-{[2-(4-pyridinyl)ethyl]amino}ethenyl)amino]ethyl}-1H-indol-5-yl)-N,N-diethyl-2-methylpropanamide;

2-[3-2{-[((cyanoimino){[2-(4-pyridinyl)ethyl]amino}methyl)amino]ethyl}-2-(3,5-dimethylphenyl)-1H-indol-5-yl]-N,N-diethyl-2-methylpropanamide;

2-[3-2{-[((cyanoimino){[2-(2-pyridinyl)ethyl]amino}methyl)amino]ethyl}-2-(3,5-dimethylphenyl)-1H-indol-5-yl]-N,N-diethyl-2-methylpropanamide;

2-[3-2{-[((cyanoimino){[2-(1-imidazoyl)ethyl]amino}methyl)amino]ethyl}-2-(3,5-dimethylphenyl)-1H-indol-5-yl]-N,N-diethyl-2-methylpropanamide;

2-[2-(3,5-dimethylphenyl)-3-(2-{[(phenethylamino)carbonyl]amino}ethyl)-1H-indol-5-yl]-N,N-diethyl-2-methylpropanamide;

2-[2-(3,5-dimethylphenyl)-3-(2-{[(4-pyridinyl)ethyl]amino)carbonyl]amino}ethyl)-1H-indol-5-yl]-N,N-diethyl-2-methylpropanamide;

2-[3-2{-[((cyanoimino){[3-(4-methylpiperazino)propyl]amino}methyl)amino]ethyl}-2-(3,5-dimethylphenyl)-1H-indol-5-yl]-N,N-diethyl-2-methylpropanamide;

2-[3-2-{-[((cyanoimino){[2-(2-piperidinyl)ethyl]amino}methyl)amino]ethyl}-2-(3,5-dimethylphenyl)-1H-indol-5-yl]-N,N-diethyl-2-methylpropanamide;

2-[3-[2-({(cyanoimino)[3-(4-pyridinyl)-pyrrolidin-1-yl]methy}lamino)ethyl]-2-(3,5-dimethylphenyl)-1H-indol-5-yl]-N,N-diethyl-2-methylpropanamide;

2-[3-2{-[((cyanoimino){[2-(4-pyridinyl)ethyl]aminomethyl}methyl)amino]ethyl}-2-(3,5-dimethylphenyl)-1H-indol-5-yl]-N,N-diethyl-2-methylpropanamide;

2-[3-[2-[(2-nitro-1-([3-(4-pyridinyl)-pyrrolidin-1-yl]ethenyl}amino)ethyl]-2-(3,5-dimethylphenyl)-1H-indol-5-yl]-N,N-diethyl-2-methylpropanamide;

2-[3-[2-((carbonyl)[3-(4-pyridinyl)-pyrrolidin-1-yl]amino)ethyl]-2-(3,5-dimethylphenyl)-1H-indol-5-yl]-N,N-diethyl-2-methylpropanamide;

2-[3-[2-({(imino)[3-(4-pyridinyl)-pyrrolidin-1-yl]methyl}amino)ethyl]-2-(3,5-dimethylphenyl)-1H-indol-5-yl]-N,N-diethyl-2-methylpropanamide; and 2-[3-[2-({(cyanoimino)[3-(4-pyridinyl)-pyrrolidin-1-yl]methyl}amino)ethyl]-2-(3,5-dimethylphenyl)-1H-indol-5-yl]-1-cyclopropylcarboxylic acid-diethylamide.

The compounds of formula I can be prepared by a process comprising a step selected from (a) to (e) as follows:

(a) Reaction of XV as follows

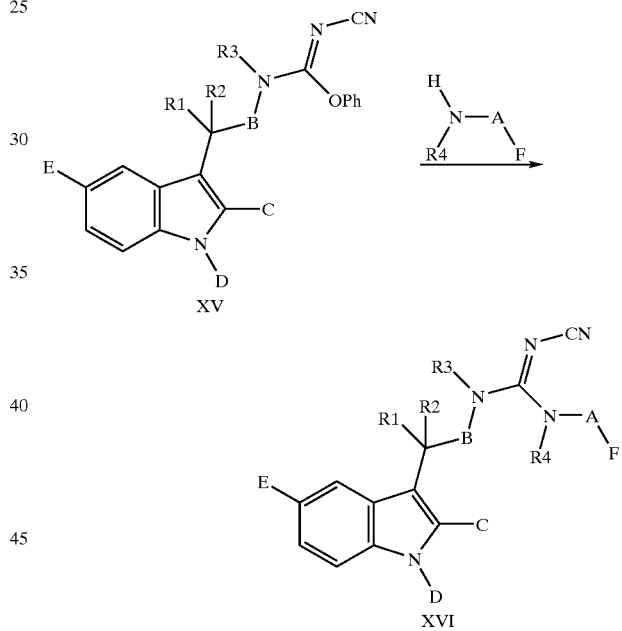

(b) Cleavage of the CN group of XVI in the presence of acid to produce XVII

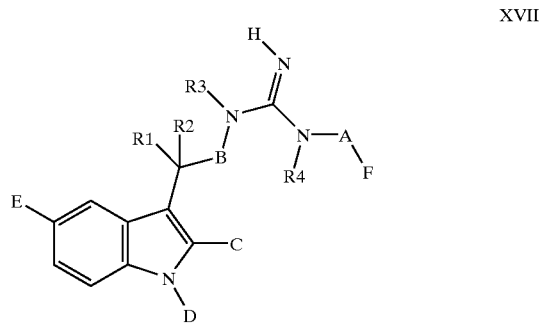

(c) Reaction of XVIII as follows

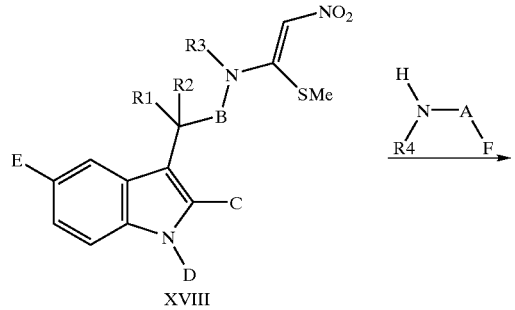

XVIII

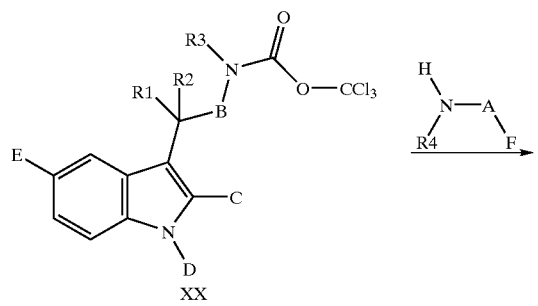

XIX (d) Reaction of XX as follows

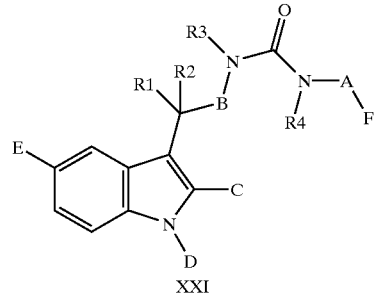

XX

XXI (e) Reaction of XXII as follows

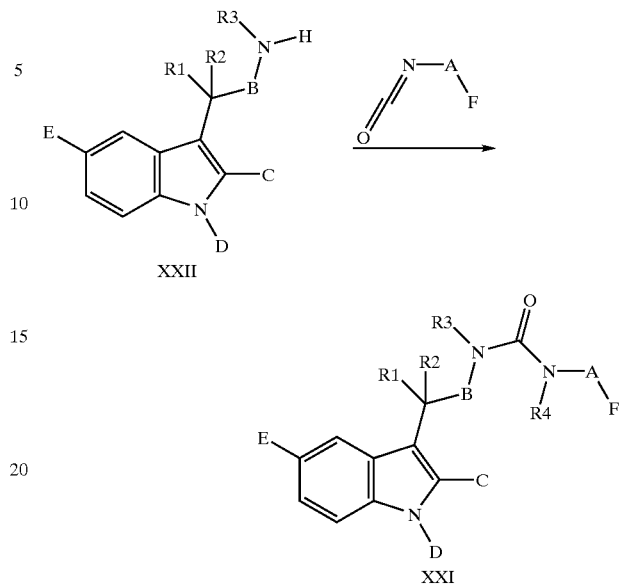

XXII

XXI

It will be appreciated by those skilled in the art that in the processes of the present invention certain functional groups such as hydroxyl or amino groups in the starting reagents or intermediate compounds may need to be protected by protecting groups. Thus, the preparation of the compounds of formula I may involve, at an appropriate stage, the addition and subsequent removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The invention also contemplates pharmaceutically acceptable salts and solvates of compounds of formula I.

EXPERIMENTAL

General Reaction Schemes

In the following schemes, group C has been depicted as substituted phenyl for illustration purposes only. Other definitions of C are also appropriate.

Scheme a.
Fischer indole synthesis.

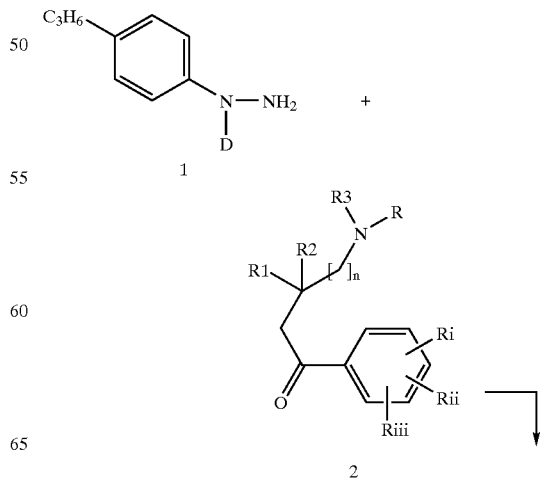

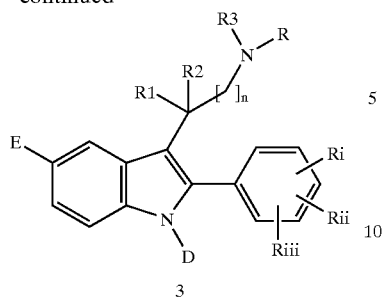

Tryptamines, such as 3 can be synthesised by the classic Fisher indole synthesis reaction by the condensation of a hydrazine 1 and a ketone 2, bearing hydrogen atoms α to the carbonyl (Scheme a). Treatment of these reactants in a suitable solvent, such as acetic acid, ethanol, tert-butanol, toluene, in the presence of an acid, such as sulphuric, hydrochloric, polyphosphoric and/or a Lewis acid, for example, boron trifluoride, zinc chloride, magnesium bromide, at elevated temperatures (for example 100° C.), gives the desired product. R represents a protecting group, eg tert-butylcarbamate or phthalimide.

Tryptamines, such as represented in structure 5, can also be made using aldehydes 4, bearing hydrogen atoms α to the carbonyl, by cyclisation using the conditions above. In this case the substituent at the 2-position must be added later (see scheme d).

Tryptamine may also be synthesised utilising the Granburg reaction, wherein a hyradazine 1 is mixed with ketone 6, bearing a chlorine atom γ to the carbonyl, and heated in a suitable solvent such as ethanol, tert-butanol, toluene at a temperature between 50° C. and 120° C. (Scheme c).

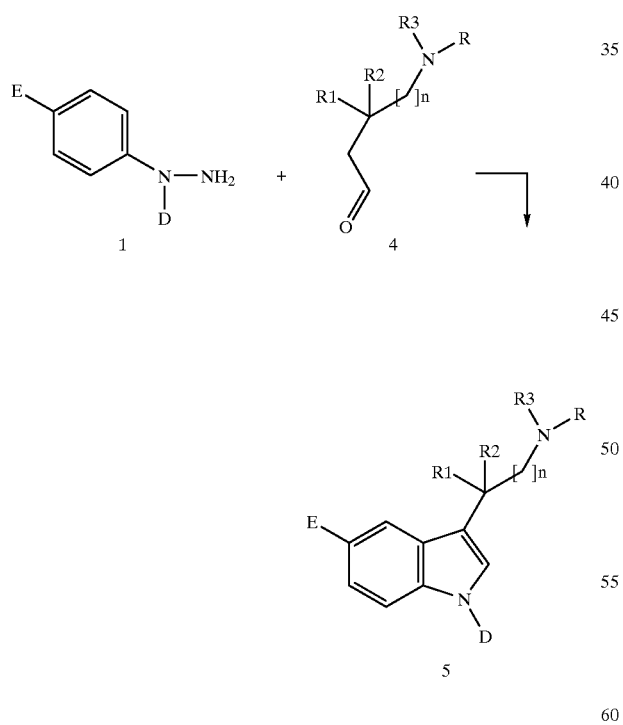

The tryptamine 5 can be treated with a 'bromine source', such as molecular bromide, pyridinium tibromide, pyrrolidone hydrobromide or polymer supported reagent equivalents, in an inert solvent such as chloroform, methylene chloride at −10° C. to 25° C. to yield the 2-bromo compound 8 (Scheme d). Reaction under Suzuki conditions with a palladium(0) catalyst, a weak base such aqueous sodium carbonate or saturated sodium hydrogen carbonate and the like, and a substituted aryl boronic acid from commercial sources or prepared (as described in: Gronowitz, S.; Hornfeldt, A.-B.; Yang, Y.,-H *Chem. Sci.* 1986, 26, 311–314), in an inert solvent such as toluene, benzene, dioxane, THF, DMF and the like, with heating between 25° C. and 100° C., preferably 80° C., for a period of 1–12 hours, to give the desired compound 3.

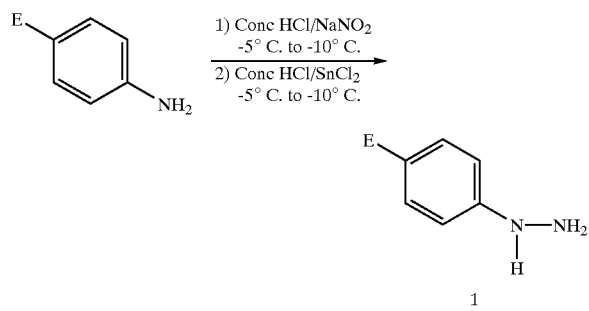

The hydrazines 1 can be purchased from commercial sources either as a free base or suitable salt (e.g. hydrochloride), which are both acceptable under the reaction conditions. Hydrazines may be synthesised by the two-step process of diazotisation of an aniline, under the preferred conditions of concentrated hydrochloric acid sodium nitrite at a temperature between −10° C. and −5° C., then reduction under the preferred conditions of tin(II) chloride in concentrated hydrochloric acid at a temperature between −10° C. and −5° C.

Scheme e.

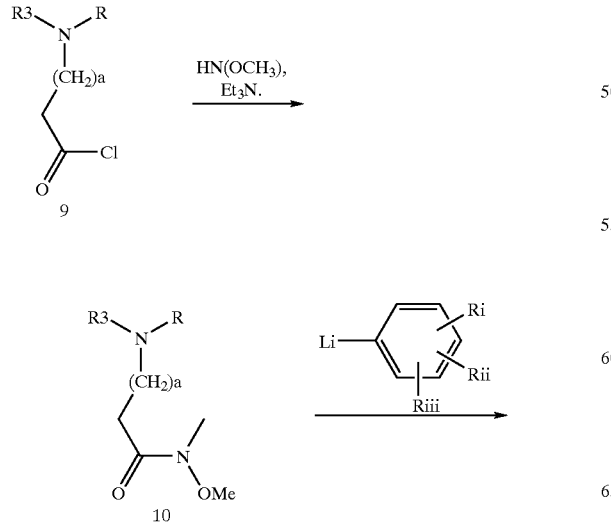

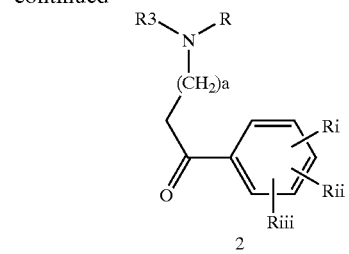

Substituted ketones 2 can be prepared, as outlined in Scheme e starting from appropriate acid chlorides such as 9. Treatment of the acid chloride with N,N-dimethylhydroxylamine hydrochloride in the presence of an amine base such as triethylamine, and a suitable solvent such as methylene chloride at a temperature of −10° C. to 25° C., yields the amide 10. Further reaction with a substituted aryl organolithium (prepared essentially as described in Wakefield B. J.; *Organolithium Methods* Academic Press Limited, 1988, pp. 27–29 and references therein) in an inert solvent such as tetrahydrofuran, diethyl ether, benzene, toluene or mixture thereof and the like, at a temperature between −100° C. and 0° C. then quenching of the reaction mixture with a mineral acid such as hydrochloric acid, yields the aryl ketone 2.

Scheme f.

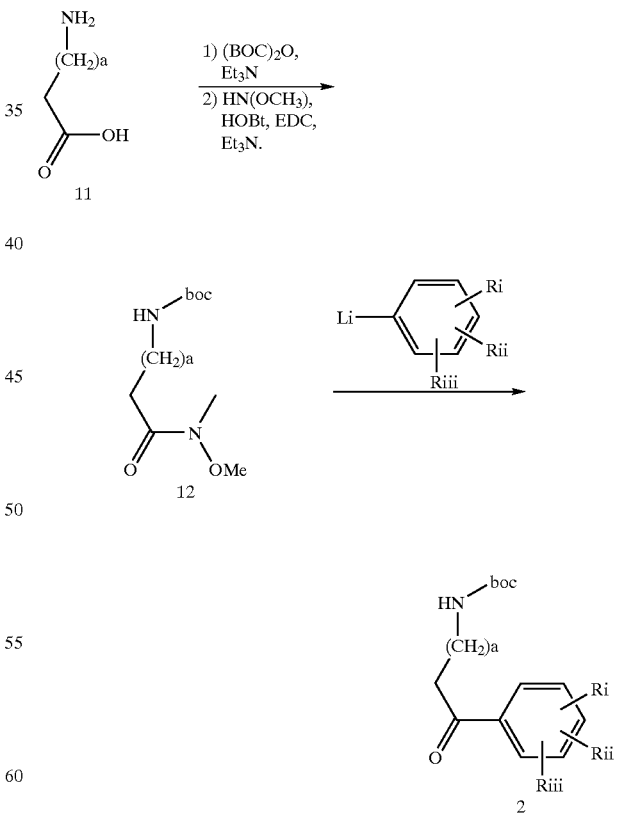

Commencing with a readily available amino acid with a suitable chain length [a] 11, the nitrogen atom can be brought in at the beginning of the synthesis by the route shown in Scheme f. Protection of the amine group of 11 with a tert-butylcarbamate group is achieved by condensation with di-tert-butyl dicarbonate in the presence of an amine base, for example triethylamine, in an inert solvent such as methylene chloride, chloroform, benzene, toluene, tetrahydrofuran and mixtures thereof and the like, at a temperature of −10° C. to 25° C. Coupling of the acid product with N,N-dimethylhydroxylamine in the presence of a coupling reagent 1-(3-dimethylaminopropyl)-3-ethylcarbodiimide hydrochloride (EDC) or 1,3-dicyclohexylcarbodiimide (DCC) or the like, with or without 1-hydroxybenotriazole (HOBt), and suitable amine base, such as triethylamine and the like, in an inert solvent such as methylene chloride, chloroform, dimethylformamide, or mixture thereof, at or near room temperature for a period of 3 to 24 h provided the corresponding coupled product 12. Following the same route described above for scheme d, the aryl group can then be installed.

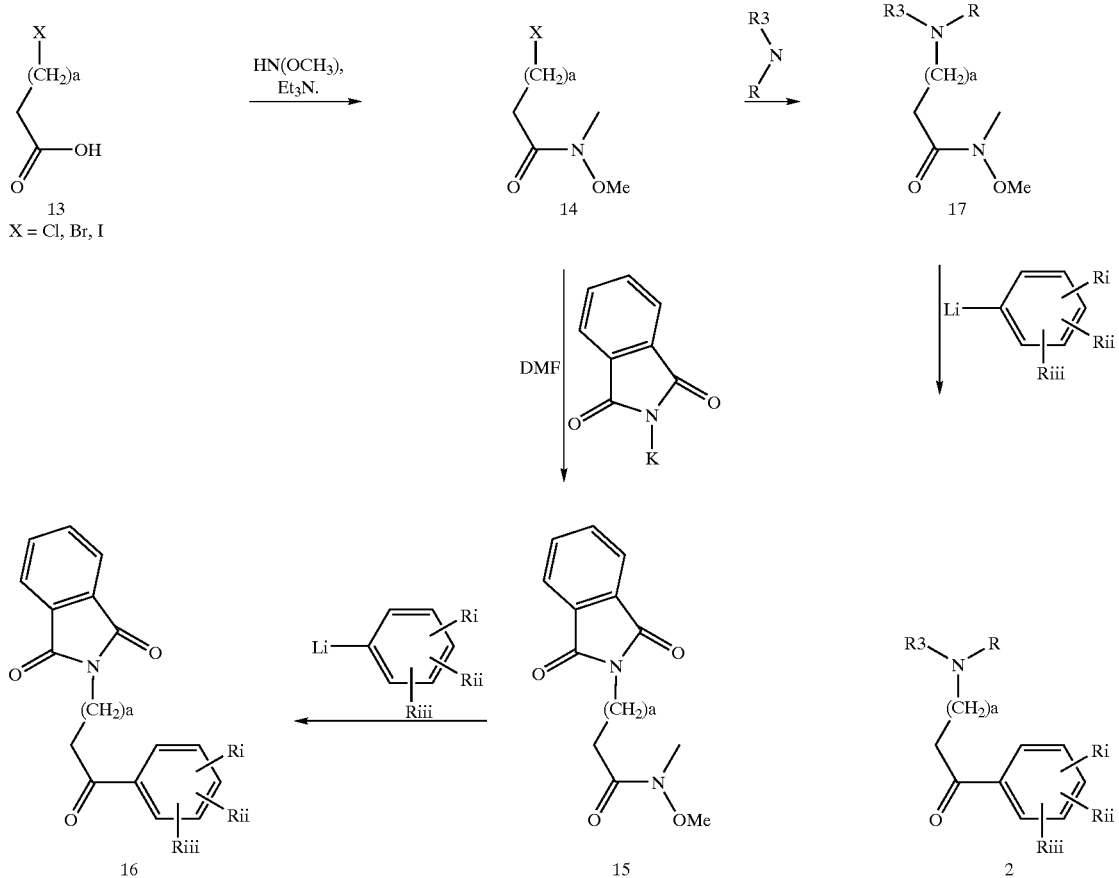

Scheme g illustrates another method for the synthesis of ketone such as 2 and 16, where the nitrogen group is introduced at a latter stage. As above a Weinreb amide 14 can be synthesised from an acid chloride. Treatment with the required amine, in an inert solvent such as THF, toluene, water and the such like can displace the group X to give 17. As above the aryl group can be introduced by displacement of the Weinreb amide with a suitable aryl lithium nucleophile. Alternatively the nitrogen atom can be introduced already protected as a phthalimide by displacement of the group x by potassium phthalimide, or similar salt thereof, by heating in an inert polar solvent such as DMF, DMSO, THF, toluene with or without the presence of a catalyst such as tetrabutylammonium iodide and the such like, to yield the compound 15. Again displacement of the Weinreb amide with an organolithium species completes the synthesis of a ketone suitable for cyclisation under the Fischer condition described above for indole synthesis.

Scheme h.

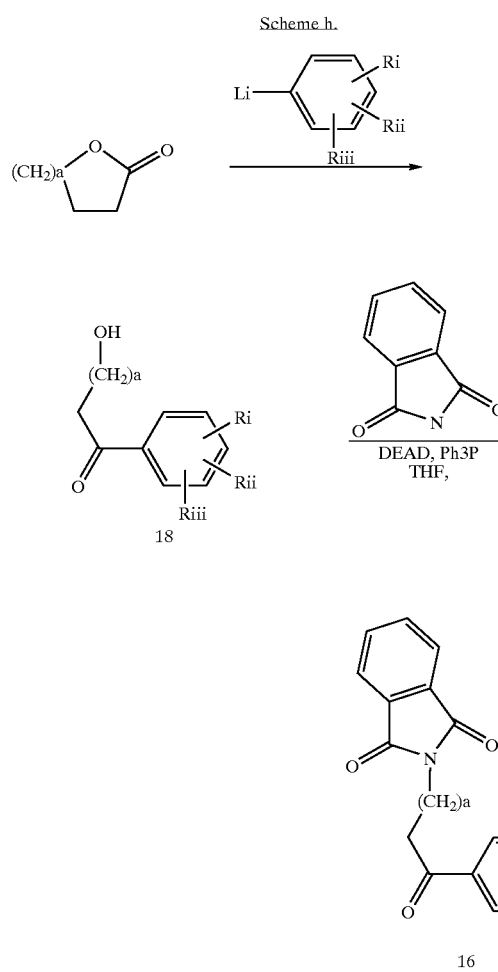

An alternative approach to a phthalimide protected nitrogen ketone, such as 16, can be taken by firstly treating a lactone, with an organolithium species as in the above schemes in a suitable solvent such as THF or ether at a low temperature of between −100° C. and −50° C. to yield a primary alcohol 18 (Scheme h). The hydroxyl function of 18 is replaced with a phthalimide group by a Mitsunobu reaction with an activating agent such as diethyldiazocarboxylate (DEAD), diisopropyldiazocarboxlate or the like with triphenylphosphine, tri-butylphosphine and the like, in an inert solvent such as benzene, toluene, tetrahydrofuran or mixtures thereof to give the desired ketone 16.

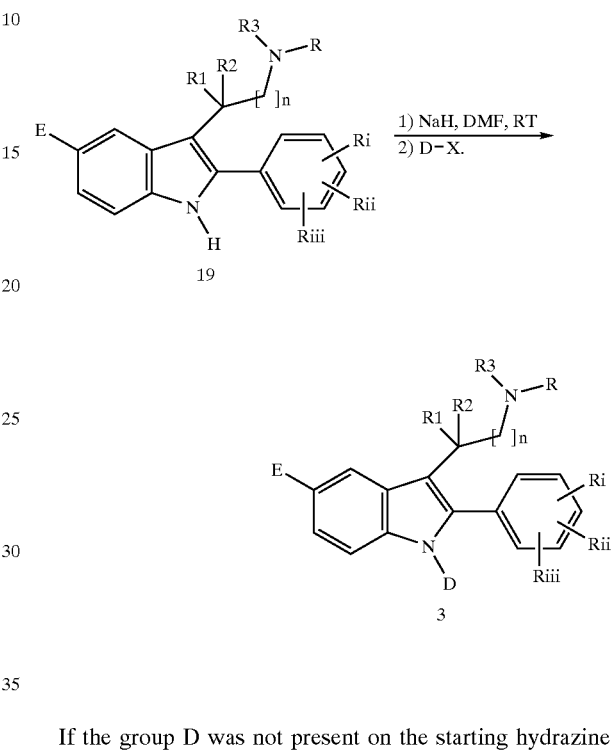

If the group D was not present on the starting hydrazine before cyclisation to form an indole it may be added post cyclisation by an alkylation reaction (19→3). The indole is deprotonated by a strong base, such as sodium hydride, n-butyl lithium, lithium diisopropylamine, sodium hydroxide, potassium tert-butoxide in a suitable inert solvent such as THF, DMF, DMSO and the such like, and an alkyl halide added and the mixture stirred at room temperature.

Scheme i

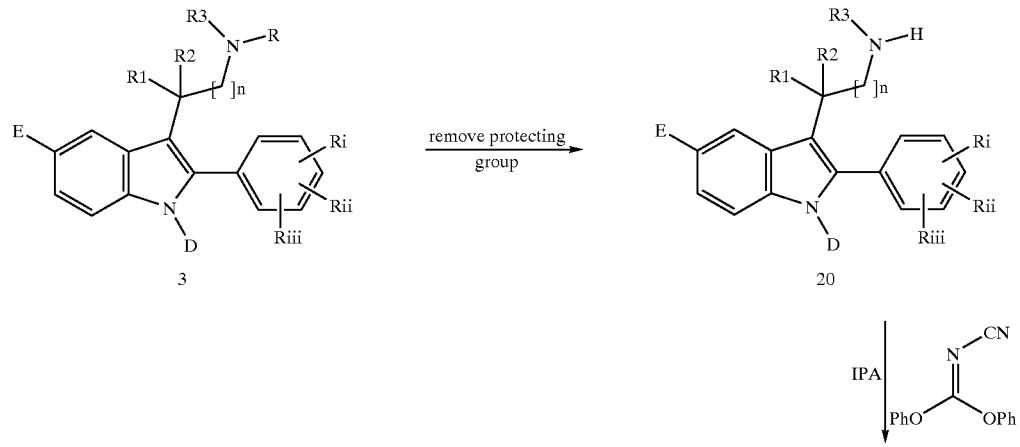

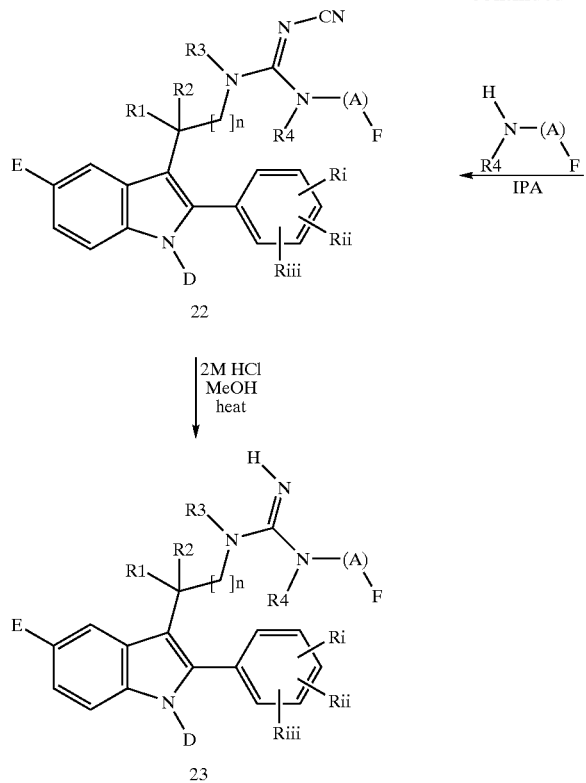

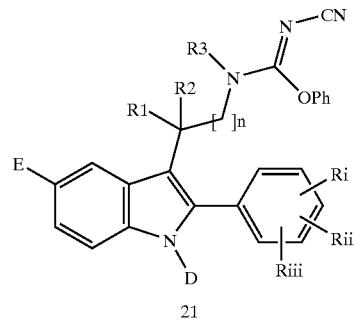

Depending on the route used above a tryptamine 20 suitable for conversion to a cyano-guandine can be formed by removal of the protecting group, for example if a tert-butylcarbamate group was used then removal is accomplished using a strong acid, for example trifluoroacetic acid or hydrochloric acid in an inert solvent such as methylene chloride, chloroform, THF or dioxane at a temperature between −20° C. and 25° C. A phthalimide group, for example, can be removed by hydrazine in a suitable solvent for example methanol, ethanol, methylene chloride, chloroform, THF dioxane at a temperature between −20° C. and 25° C. The primary amine 20 can be converted to a cyano-guanidine 22 by the two step process of reaction with diphenyl cyanocarbonimidate in an inert organic solvent such as isoproplyl alcohol, methylene chloride, chloroform, benzene, tetrahydrofuran and the like, at a temperature between −20° C. and 50° C., followed by condensation with an appropriately substituted amine in an inert organic from the list above, with heating at a temperature between −20° C. and 100° C. (Scheme I 20→21→22). Further treatment of 22 with 2 molar Hydrochloric acid in methanol at elevated temperature yields guanidine compounds 23.

Scheme j.

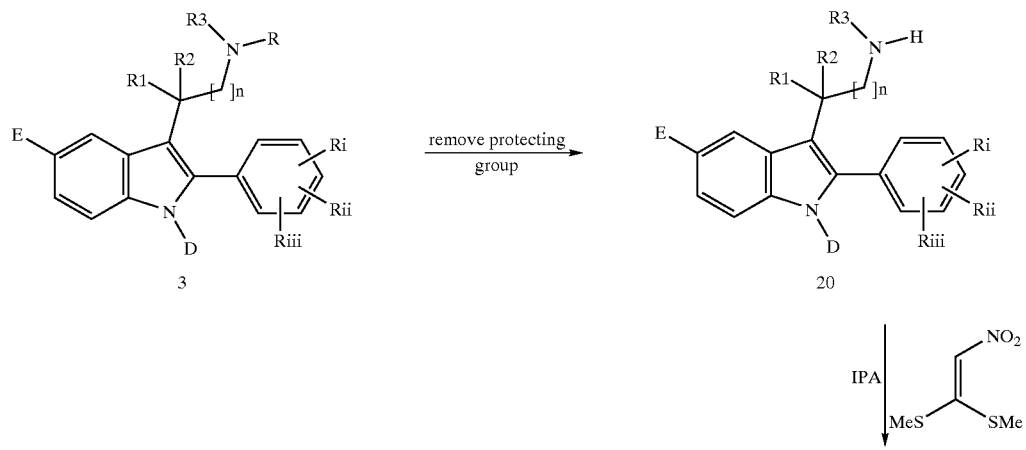

25

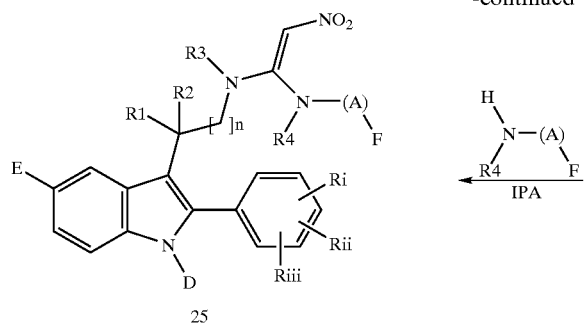

26

-continued

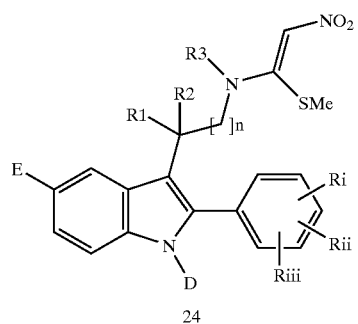

Similarly, reaction with 1,1'-bis(methylthio)-2-nitroethylene in an inert solvent such methylene chloride, chloroform, benzene, tetrahydrofuran and the like, followed by condensation with an appropriately substituted amine in an inert organic solvent from the list above yields the nitroethyleneimidazo[1,2-a]pyridine 25 (Scheme j, 20→24→25).

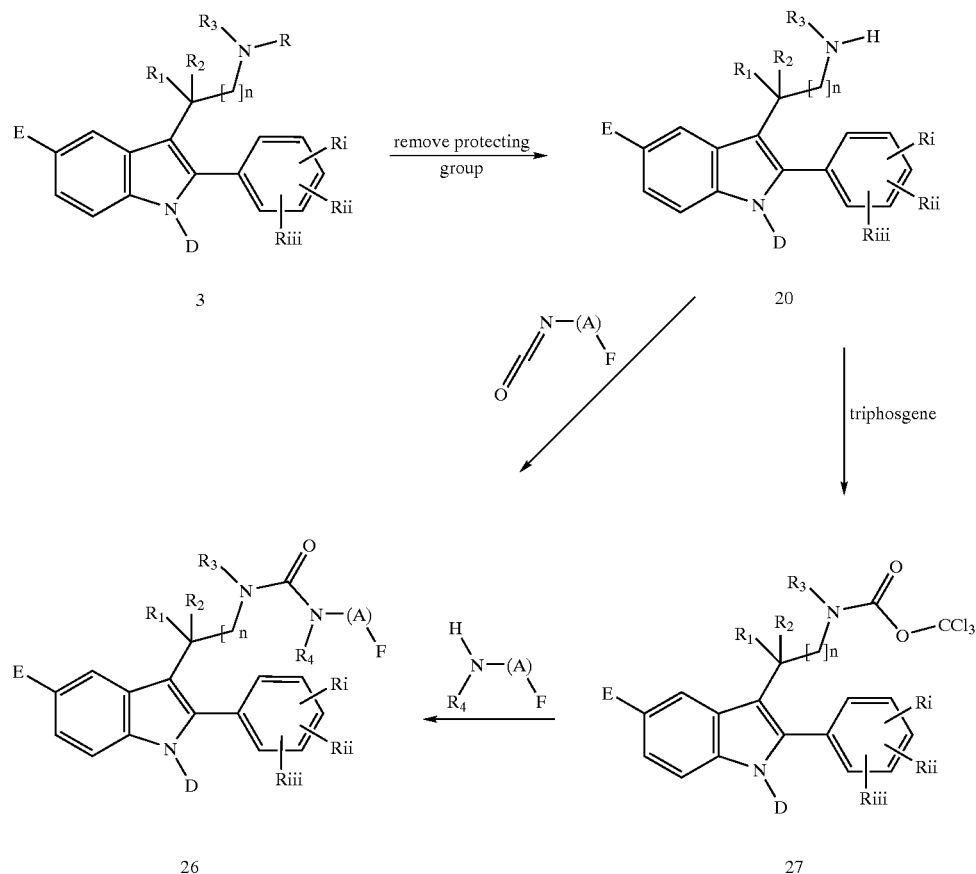

Again in a similar fashion the suitable tryptamine 20, derived from deprotection, can be converted to a urea by either direct treatment with an iso-cyanate in an inert solvent such as methylene chloride, chloroform or THF and the such like, or by a two step procedure of reaction with triphosgene (20→27) followed by addition of an amine (27→26), bearing the required substitution to yield 26.

EXAMPLES

The invention will now be illustrated with the following non-limiting Examples in which, unless otherwise stated:

(i) evaporations were carried out by rotary evaporation in vacuo and work-up procedures were carried out after removal of residual solids such as drying agents by filtration;

(ii) operations were carried out at room temperature, that is in the range 18–25° C. and under an atmosphere of an inert gas such as argon or nitrogen;

(iii) yields are given for illustration only and are not necessarily the maximum attainable;

(iv) the structures of the end-products of the Formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet; quin, quintet;

(v) intermediates were not generally fully characterised and purity was assessed by thin layer chromatography (TLC), high-performance liquid chromatography (HPLC), infra-red (IR) or NMR analysis;

(vi) chromatography was performed on silica (Merck Keiselgel: Art.9385);

| Abbreviations | |
|---|---|
| brine | a saturated solution of sodium chloride in distilled water |
| DCC | 1,3-dicyclohexylcarbodiimide |
| DEAD | diethyldiazocarboxylate |
| DMSO | Dimethyl sulphoxide |
| DMF | dimethylformamide |
| EDC | 1-(3-dimethylaminopropyl)-3-ethylcarbodiimide hydrochloride |
| HOBt | 1-hydroxybenotriazole |
| IPA | isopropyl alcohol |
| RM | reaction mixture |
| RT | room temperature |
| THF | tetrahydrofuran |

Example 1

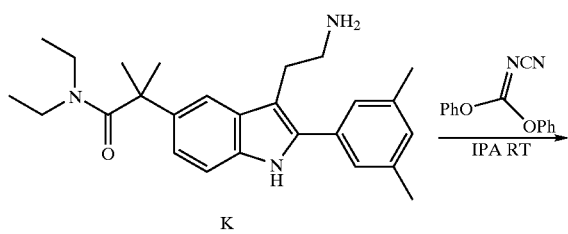

K

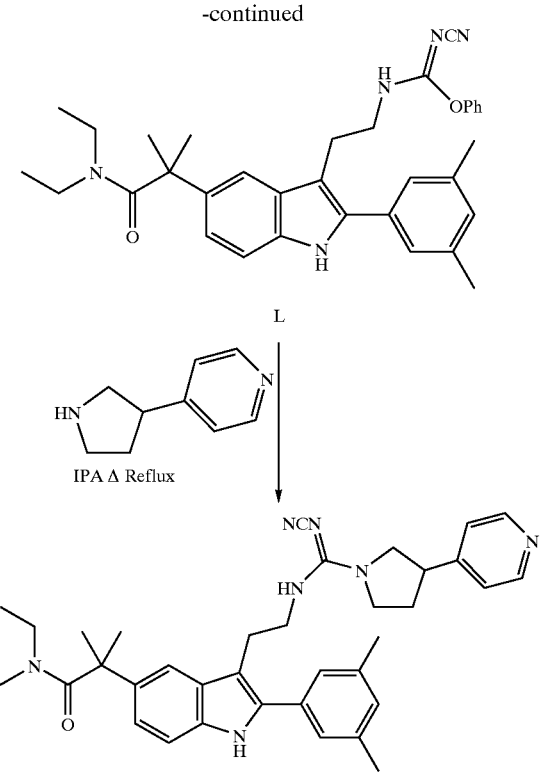

EXAMPLE 1

4-Pyrrolidin-3-yl pyridine (1.00 g, 6.76 mmol) was added to a stirred suspension of L (1.00 g, 1.80 mmol) in IPA (5 ml) and the mixture heated at reflux for 36 hours. The RM was concentrated in vacuo and the residues purified by chromatography on $SiO_2$ (Isolute, 50 g), eluting with a gradient 0–10% $MeOH/CH_2Cl_2$ to give Example 1 as a white foam 672 mg(61%).

$^1$H NMR (300 MHz, $CDCl_3$) 0.60–0.80 (m,3H); 1.00–1.20 (m,3H); 1.60 (s, 6H); 1.80–2.00(m,1H); 2.10–2.30 (m,1H); 2.35 (s,6H); 2.80–3.00 (m,2H); 3.10–3.50 (m, 8H); 3.60–3.80 (m,3H); 4.40 (m, 1H); 6.97 (s,1H); 7.00–7.15 (m,3H); 7.20 (s,2H); 7.28–7.36 (m,1H); 7.41 (s,1H); 8.22 (s,1H); 8.48–8.60 (m,2H).

MS (ES$^+$) m/z (M+H)$^+$604.56

MS (ES$^-$) m/z (M−H)$^-$602.54

Preparation of Intermediate L

Diphenyl cyanocarbonimidate (1.5 g, 6.3 mmol) was added to a stirred solution of K (1.5 g, 3.7 mmol) in IPA and the mixture stirred 18 hours at RT. The RM was concentrated in vacuo and the residues redissolved in EtOAc (150 ml). The organics were washed with saturated $NaHCO_3$ (3×70 ml), brine (2×75 ml), dried ($MgSO_4$), filtered and evaporated. The crudes were purified by flash chromatography on $SiO_2$ (Merck 9385) eluting with a gradient 0–5% MeOH/ $CH_2Cl_2$ to give L as an off-white foam 1.9 g(95.4%).

$^1$H NMR (300 MHz, $CDCl_3$) 0.60–0.80 (m,3H); 1.00–1.20 (m,3H); 1.55(s,6H);2.35 (s,6H); 2.75–3.20 (m,2H); 3.10–3.45 (m, 4H); 3.60–3.75 (m,2H); 6.30–6.45 (m,1H); 6.67–6.80 (m,2H); 7.00–7.50 (m,9H); 8.18 (s,1H).

MS (ES$^+$) m/z (M+H)$^+$550.36

MS (ES$^-$) m/z (M−H)$^-$548.30, 454.38

Preparation of Intermediate K
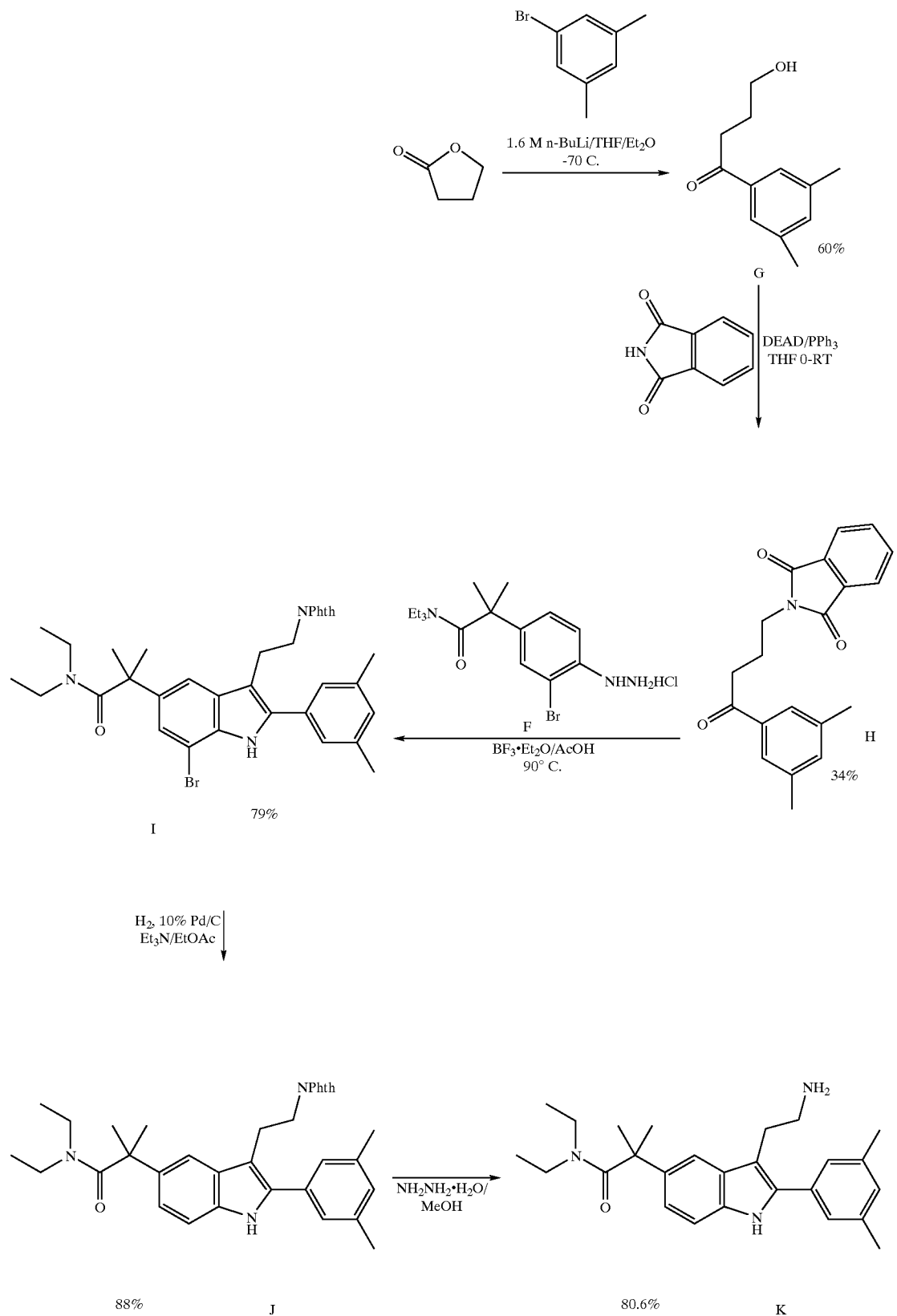

n-BuLi (1.6M in Hexanes) (100 ml, 160 mmol) was added dropwise to a stirred, cooled (−78° C.) solution of 5-Bromoxylene (21.73 ml, 160 mmol) in THF (235 ml) and Et$_2$O (235 ml) such that the internal temperature remained <−65° C. The resulting yellow suspension was allowed to stir for 1.25 hours before it was added via a cannula to a stirred, cooled (−78° C.) solution of—Butyrolactone (14.7 ml, 192 mmol) in THF (180 ml) such that the internal temperature remained <−70° C. The mixture was then stirred at this temperature for a further 5 hours, quenched with saturated NH$_4$Cl (200 ml) and extracted with Et$_2$O (3×100 ml). The combined organics were washed with brine (2×100 ml), dried (MgSO$_4$), filtered and concentrated to a yellow oil. This was then purified by chromatography on SiO$_2$ (Merck 9385) eluting with 45% EtOAc/i-Hexane to give G as a pale yellow oil 15.74 g(60%).

$^1$H NMR (300 MHz, DMSO-D$_6$) 1.70 (q,2H); 2.30 (s,6H); 2.98 (t,2H; 3.42 (q,2H); 4.43 (t,1H); 7.22 (s,1); 7.52(s, 2H).

Diethyl Azodicarboxylate (22.5 ml, 143 mmol) was added dropwise to a stirred, cooled (−5° C.) solution of G (24.0 g, 124 mmol), Phthalimide (20.0 g, 136 mmol) and Triphenylphosphine (36.0 g, 136 mmol) in THF (450 ml) such that the internal temperature remained <0° C. The RM was stirred for 1 hr at this temperature, diluted with EtOAc (600 ml) and washed with water (250 ml) and brine (250 ml). The organics were then dried (MgSO$_4$), filtered and concentrated to a yellow semi-solid. The crudes were purified by chromatography on SiO$_2$ (Merck 9385) eluting with 25% EtOAc/i-Hexane to give H as a white powder 13.3 g (34%).

$^1$H NMR (300 MHz, DMSO-D$_6$) 1.80–2.00 (m,2H); 2.28 (s,6H); 3.03 (t,2H); 3.62 (t,2H); 7.22 (s,1H); 7.47 (s,2H); 7.70 7.90 (m, 4H).

BF$_3$.Et$_2$O (30 ml) was added to a stirred solution of F (27.0 g, 74 mmol) and H (24.4 g, 77 mmol) in AcOH (450 ml) and the resulting mixture heated at 90° C. for 48 hours. The RM was evaporated to dryness and the residues treated with saturated NaHCO$_3$ (100 ml). The resulting solids were collected by filtration, triturated with MeOH/CHCl$_3$ and re-filtered. The filtrates were concentrated to give I as an off-white powder 36 g (79%).

$^1$H NMR (300 MHz, CDCl$_3$) 0.60–0.75(m,3H); 1.00–1.15 (m,3H); 1.54 (s,6H); 2.25 (s,6H); 2.80–2.95 (m,2H); 3.24–3.40 (m,2H); 3.15–3.23 (m, 2H); 3.80–3.90 (m,2H); 6.80 (s,1H); 7.06 (s,2H); 7.12 (s,1H); 7.45 (s,1H); 7.55–7.70 (m,4H); 8.02 (s,1H).

LCMS (ES$^+$) m/z (M+H)$^+$613.9, 615.9 (UV 254 nm 100%) p A solution of I (42.0 g, 68 mmol) in MeOH (1000 ml) and Et$_3$N (10 ml) was treated with 10% Pd/C (10.0 g) and stirred under H$_2$ (2 Bar) for 48 hours. The catalyst was removed by filtration through Celite (545) and the filtrates evaporated. The residues were redissolved in EtOAc, washed with water, dried (MgSO$_4$), filtered and concentrated in vacuo to give J as a yellow foam 32.2 g (88%).

$^1$H NMR (300 MHz, CDCl$_3$) 0.60–0.80 (m,3H); 1.05–1.25 (m,3H); 1.60 (s,6H); 2.30 (s,6H); 2.85–3.05 (m,2H); 3.20–3.50 (m,4H); 3.90–4.00 (m, 2H); 6.85 (s,1H); 6.95–7.05 (m,1H); 7.12 (s,2H); 7.20–7.35 (m,1H+CHCl$_3$); 7.55–7.7 (m,3H); 7.70–7.80 (m, 2H); 8.00 (s,1H).

LCMS (ES$^+$) m/z (M+H)$^+$536.59 (UV 254 nm 100%)
LCMS (ES$^-$) m/z (M−H)$^-$534.58 (UV 254 nm 100%)

Hydrazine Hydrate (40 ml, 192 mmol) was added to a stirred solution of J (28 g, 52.3 mmol) in a mixture of MeOH (200 ml) and CH$_2$Cl$_2$ (200 ml) and stirred for 48 hours at RT. A further portion of Hydrazine Hydrate (40 ml) was added and stirring continued for another 24 hours. The RM was filtered, washed with saturated NaHCO$_3$ (4×150 ml), brine (2×100 ml), dried (MgSO$_4$), filtered and evaporated. The crudes were purified by flash chromatography on SiO$_2$ (Merck 9385) eluting with EtOAc followed by 10% MeOH/ CH$_2$Cl$_2$ to give K as a pale yellow foam 17.1 g(80.6%).

$^1$H NMR (300 MHz, CDCl$_3$) 0.60–0.80 (m,3H); 1.05–1.25 (m,3H); 1.60 (s,6H); 1.76 (s,2H+H$_2$O); 2.38 (s,6H); 2.80–3.12 (m,6H); 3.25–3.45 (m, 2H); 7.00 (s,1H); 7.02–7.07(m,1H); 7.17 (s,2H); 7.25–7.35 (m,1H); 7.42 (s,1H); 8.12 (s,1H).

LCMS (ES$^+$) m/z (M+M)$^+$406.56 (UV 254 nm 100%)
LCMS (ES$^-$) m/z (M−H)$^-$404.57 (UV 254 nm 100%)
Preparation of Intermediate F

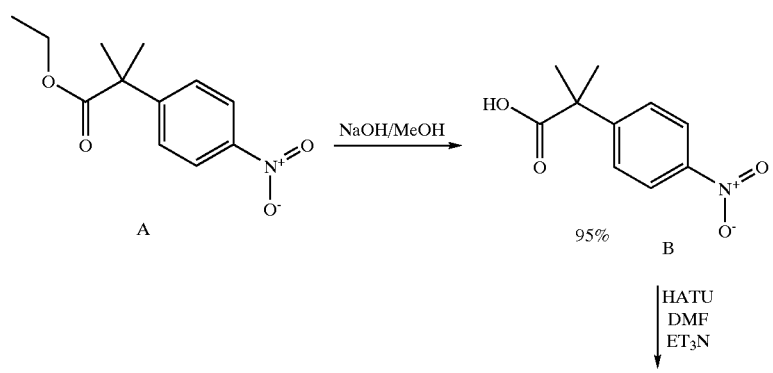

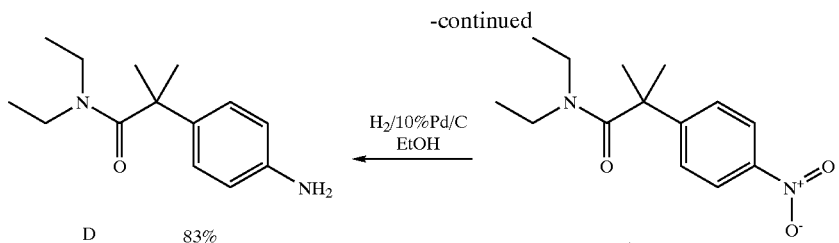

-continued

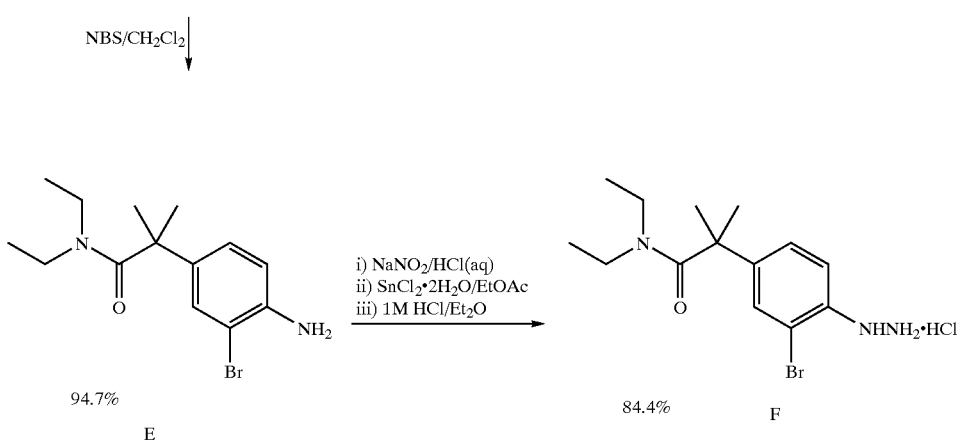

2N NaOH (510 ml, 1.02 mol) was added to a stirred solution of A (48.5 g, 205 mmol) in MeOH (550 ml) and the resulting mixture heated at reflux for 2 hours. The RM was concentrated, acidified to pH 4 with 2N HCl and extracted with EtOAc (4×200 ml). The combined organics were washed with brine (3×150 ml), dried (MgSO$_4$) filtered and evaporated to give B as a cream powder 40.3 g (95%).

$^1$H NMR (300 MHz, CDCl$_3$) 1.66 (s,6H); 7.55 (m,2H); 8.20 (m,2H).

O-(7-Azabenzotriazol-1-yl)-N,N,N',N'-Tetramethyluronium Hexafluoro-Phosphate (89.0 g, 290 mmol) was added portionwise to a stirred, cooled (0° C.) solution of B (40.3 g,192 mmol) in DMF (300 ml) and Diethylamine (300 ml). The resulting mixture was left to warm to RT and stir 70 hours. DMF was removed in vacuo and the residues redissolved in EtOAc (500 ml), washed with water (3×200 ml), brine (2×200 ml), dried MgSO$_4$, filtered and evaporated.

The crudes were purified by flash chromatography on SiO$_2$ (600 g, Merck 9385) eluting with 35% EtOAc/i-Hexane. Appropriate fractions were combined and evaporated to give C as yellow crystalline solid 44.2 g (87%).

$^1$H NMR (300 MHz, CDCl$_3$) 0.60–0.90 (m, 3H); 0.90–1.25 (m, 3H); 1.58 (s,6H); 2.65–2.95 (m, 2H); 3.20–3.45 (m, 2H); 7.40 (m, 2H), 8.20 (m, 2H).

LCMS (ES$^+$) m/z (M+H)$^+$265.48 (UV 254 nm 100%)

A solution of C (89.0 g, 338 mmol) in EtOH (2 L) was treated with 10% Pd/C (50% wet) (10.0 g) then stirred under H$_2$ (3 Bar) at RT for 3 hours. The RM was filtered through Celite (545) and evaporated to give D as a tan solid 65.5 g (83%).

$^1$H NMR (300 MHz, CDCl$_3$) 0.60–0.90 (m,3H); 0.90–1.25 (m,3H); 1.48 (s,6H); 2.80–3.10 (m,2H); 3.15–3.45 (m,2H); 3.45–3.75 (bs,2H); 6.60–6.70 (m,2H); 6.90–7.05 (m, 2H).

MS (ES$^+$) m/z (M+H)$^+$235.61

N-Bromosuccinimide (18.24 g, 102.6 mmol) was added portionwise to a stirred, cooled (0° C.) solution of D (24.0 g, 102.6 mmol) in CH$_2$Cl$_2$ (250 ml) and the mixture stirred for 2 hours. The RM was evaporated, the residues redissolved in EtOAc (200 ml), washed with saturated NaHCO$_3$ (aq) (3×200 ml), water (2×200 ml), brine (200 ml), dried MgSO$_4$, filtered and evaporated. The crudes were purified by flash chromatography on SiO$_2$ (500 g, Merck 9385) eluting with 5% MeOH/CH$_2$Cl$_2$. Appropriate fractions were combined and evaporated to give E as a tan solid 30.4 g (94.7%).

$^1$H NMR(300 MHz, CDCl$_3$) 0.60–0.90 (m,3H); 0.90–1.25 (m,3H); 1.48 (s,6H); 2.80–3.10 (m,2H); 3.15–3.50 (m,2H); 3.80–4.20 (bs,2H); 6.72 (m,1H); 6.95 (m,1H); 7.25 (m, 1H).

MS (ES$^+$) m/z (M+H)$^+$313.23, 315.26

A solution of E (15 g, 48 mmol) in conc HCl (48 ml) was cooled to −10° C. and to it was added dropwise a solution of NaNO$_2$ (3.97 g, 57.5 mmol) in water (24 ml) such that the internal temperature remained <−8° C. The resulting solution was left to stir for 1 hr at this temperature before it was added dropwise to a solution of SnCl$_2$.2H$_2$O (53.0 g, 235 mmol) in conc HCl (36.5 ml) at −12° C. such that the internal temperature remained <−10° C. The mixture was stirred for 2 hours at −10° C. then allowed to warm to 10° C. before it was quenched into water (600 ml), neutralised with solid NaHCO$_3$, filtered and extracted with EtOAc (3×400 ml). The organics were dried (MgSO$_4$), filtered and evaporated to a yellow oil. This was treated with 1M HCl/Et$_2$O and dried to give the HCl salt of F as a free flowing white powder 14.7 g (84.4%)

$^1$H NMR (300 MHz, DMSO-D$_6$) 0.50–0.85 (m,3H); 0.85–1.10 (m,3H); 1.40 (s,6H); 2.70–3.00 (m,2H); 3.00–3.40(m,2H); 7.00–7.10 (m,1H); 7.10–7.20(m, 1H); 7.20–7.30 (m,1H).

LCMS (ES$^+$) m/z (M+H)$^+$328.3, 330.3 (UV 254 nm 95%)

Following a procedure similar to that described in Example 1, the examples 1.01 to 1.30 were prepared.

| STRUCTURE | EXAMPLE | MS (ES)+ |
|---|---|---|
| 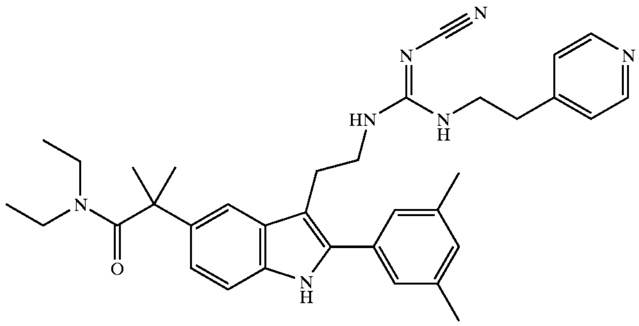 | 1.01 | 578.74(M + H)+ |
| 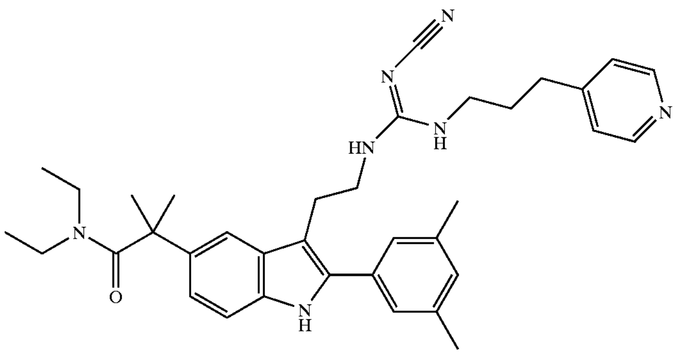 | 1.02 | 592.44(M + H)+ |
| 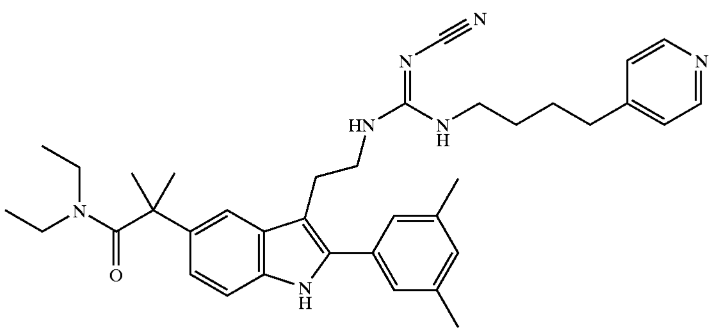 | 1.03 | 606.76(M + H)+ |
| 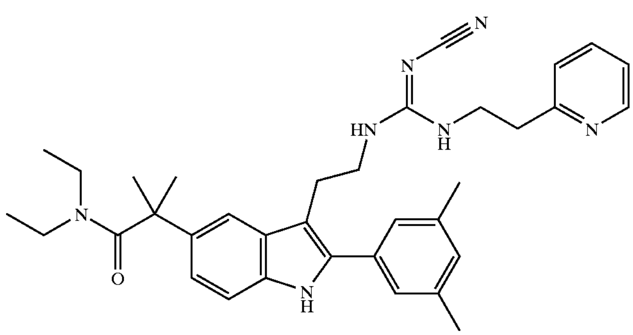 | 1.04 | 578.72(M + H)+ |

-continued

| STRUCTURE | EXAMPLE | MS (ES)+ |
|---|---|---|
| 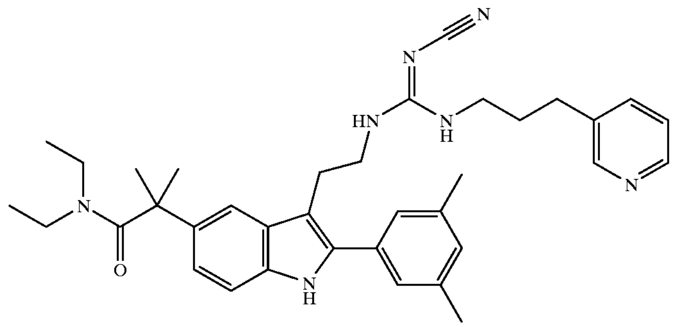 | 1.05 | 592.74(M + H)+ |
| 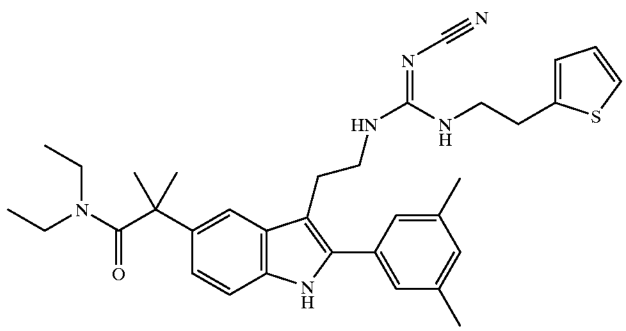 | 1.06 | 583.70(M + H)+ |
| 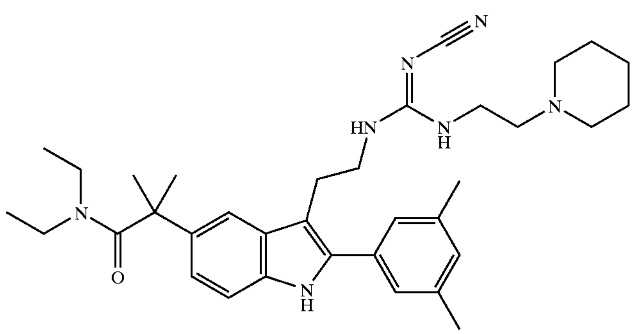 | 1.07 | 584.79(M + H)+ |
| 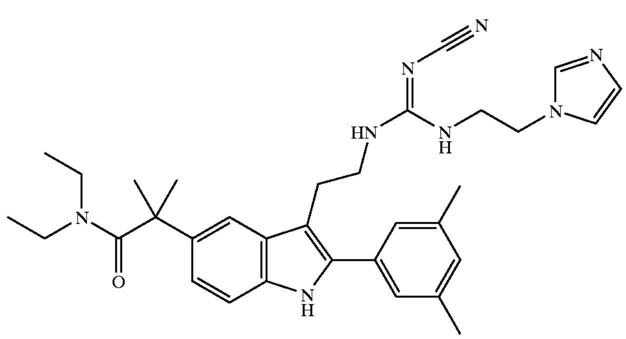 | 1.08 | 567.74(M + H)+ |

-continued
| STRUCTURE | EXAMPLE | MS (ES)+ |
|---|---|---|
| 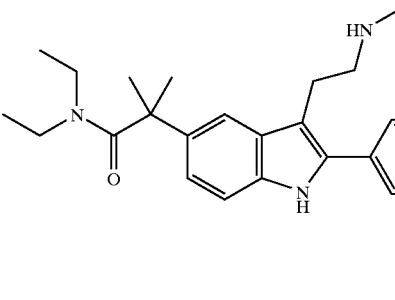 | 1.09 | 582.74(M + H)+ |
| 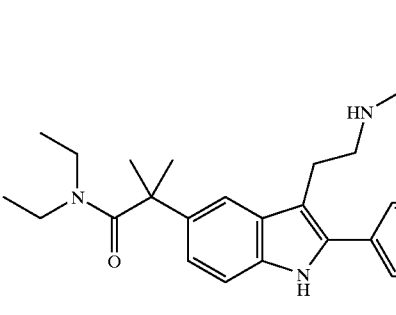 | 1.10 | 598.71(M + H)+ |
| 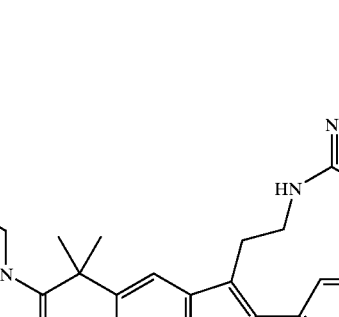 | 1.11 | 648.99(M + H)+ |
| 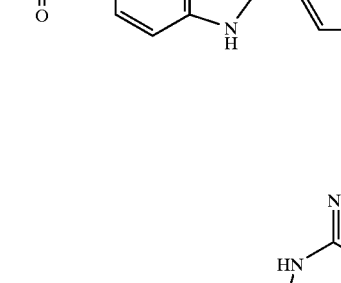 | 1.12 | 598.86(M + H)+ |

-continued
| STRUCTURE | EXAMPLE | MS (ES)+ |
|---|---|---|
| 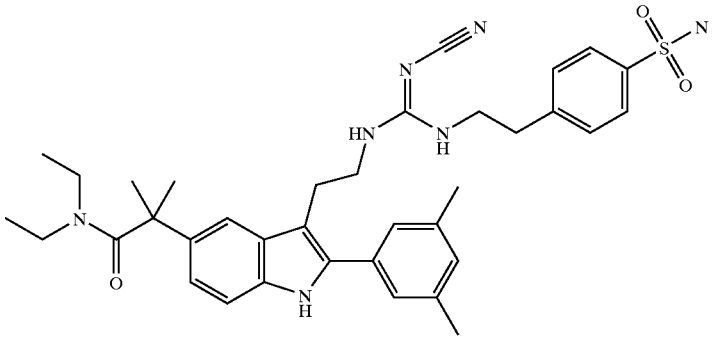 | 1.13 | 656.84(M + H)+ |
| 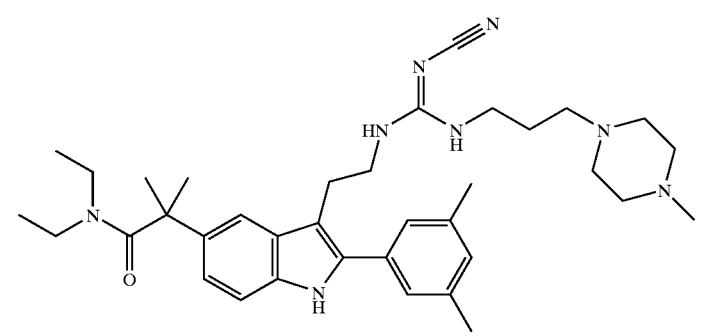 | 1.14 | 613.93(M + H)+ |
| 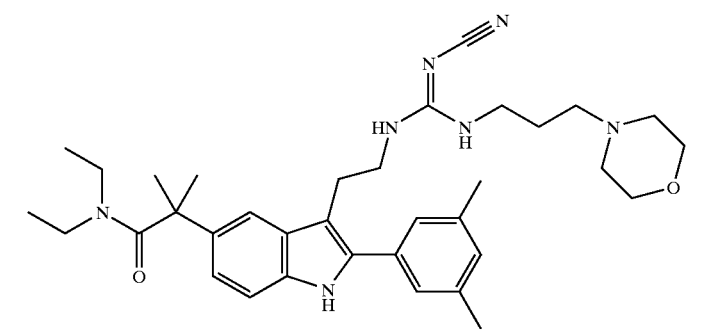 | 1.15 | 600.89(M + H)+ |
| 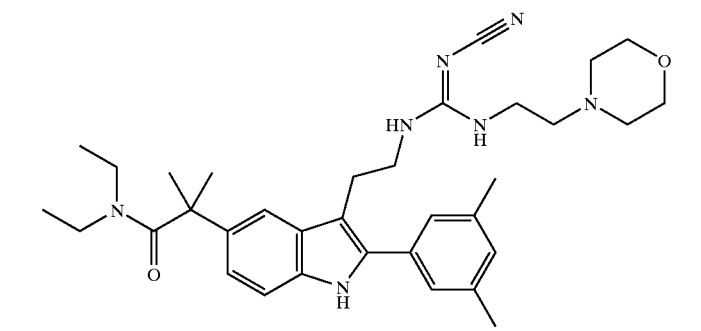 | 1.16 | 586.85(M + H)+ |

| STRUCTURE | EXAMPLE | MS (ES)+ |
|---|---|---|
| 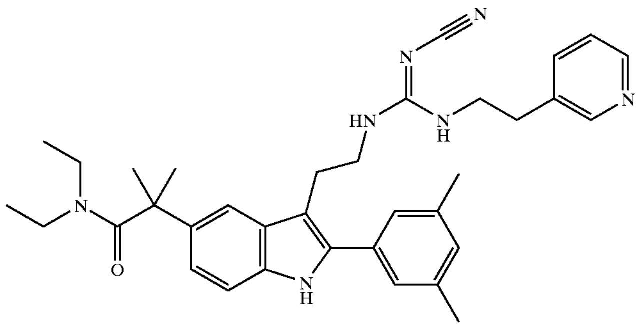 | 1.17 | 578.7(M + H)+ |
| 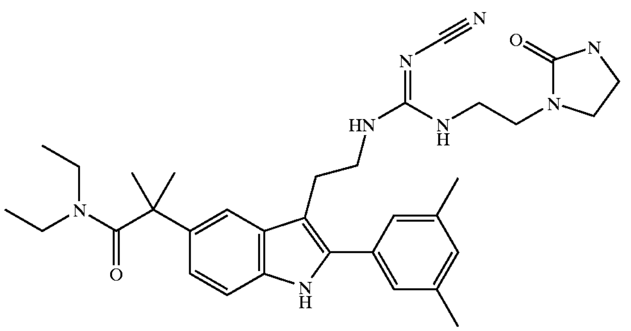 | 1.18 | 585.83(M + H)+ |
| 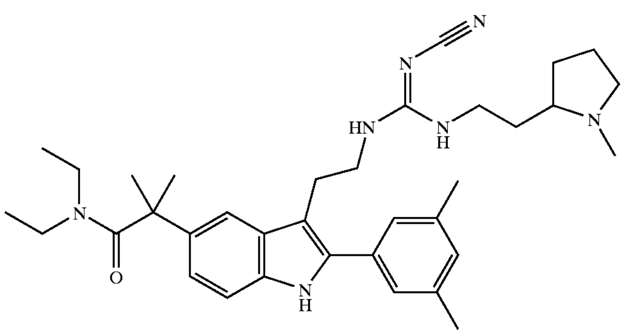 | 1.19 | 584.87(M + H)+ |
| 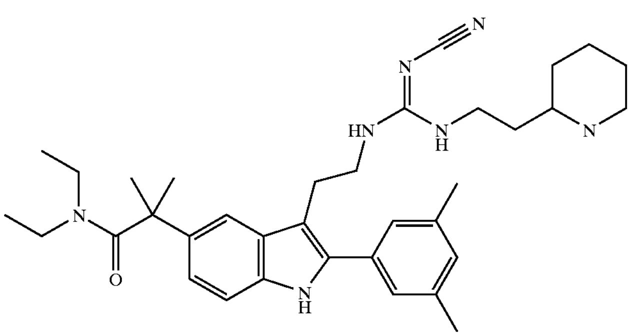 | 1.20 | 584.54(M + H)+ |

-continued

| STRUCTURE | EXAMPLE | MS (ES)+ |
|---|---|---|
| 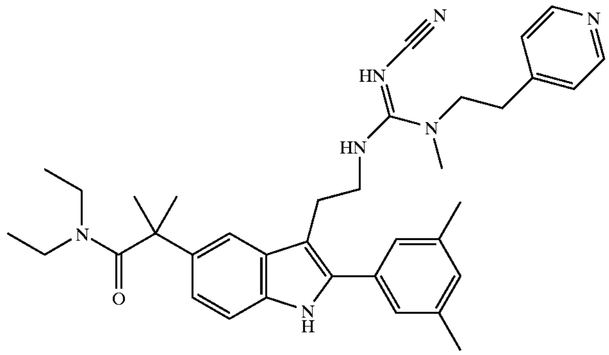 | 1.21 | 592.53(M + H)+ |
| 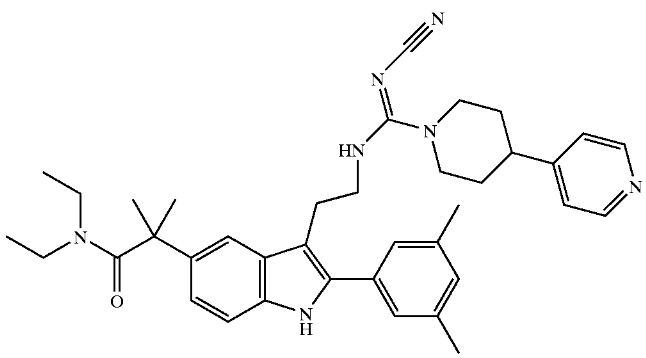 | 1.22 | 618.55(M + H)+ |
| 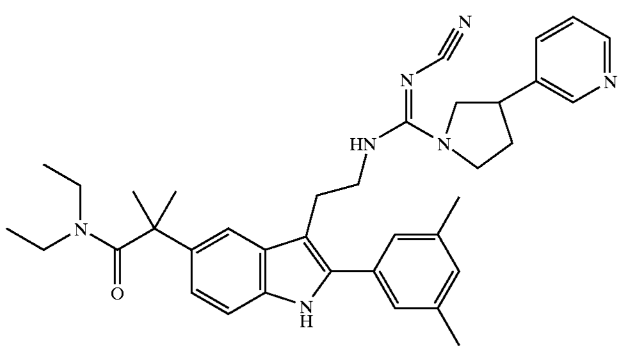 | 1.23 | 604.6(M + H)+ |
| 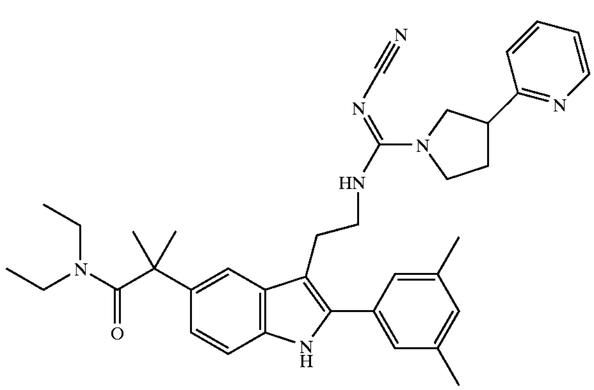 | 1.24 | 604.54(M + H)+ |

-continued
| STRUCTURE | EXAMPLE | MS (ES)+ |
|---|---|---|
| 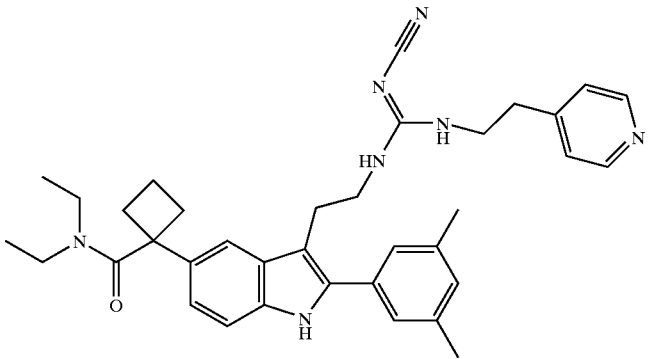 | 1.25 | 590.76(M + H)+ |
| 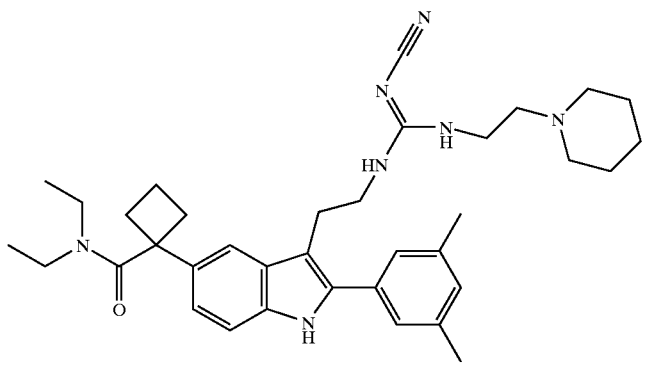 | 1.26 | 596.78(M + H)+ |
| 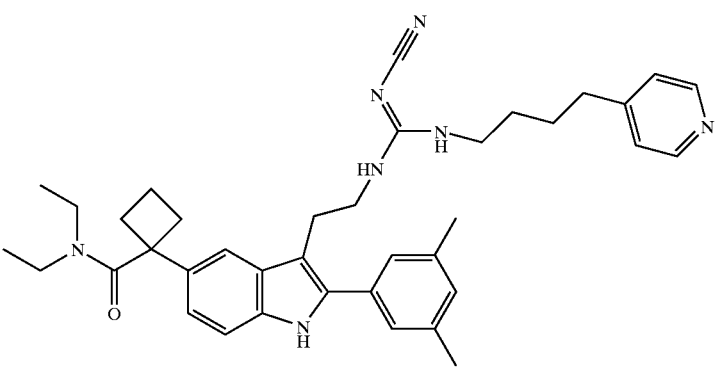 | 1.27 | 618.58(M + H)+ |
| 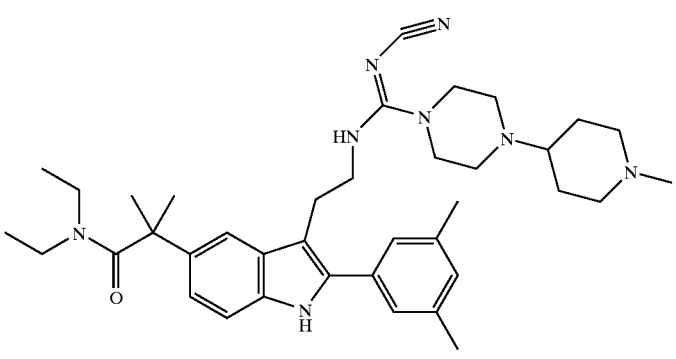 | 1.28 | 639.73(M + H)+ |

-continued
| STRUCTURE | EXAMPLE | MS (ES)+ |
|---|---|---|
| 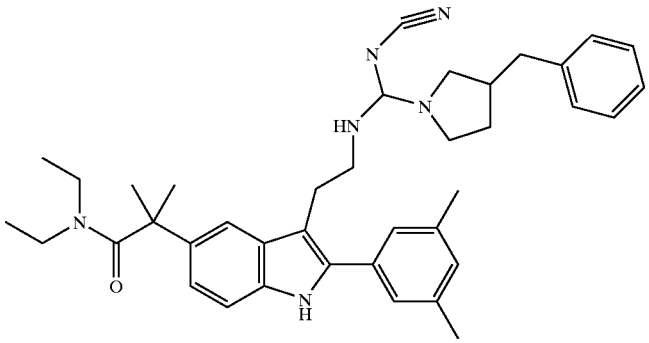 | 1.29 | 617.55(M + H)+ |
| 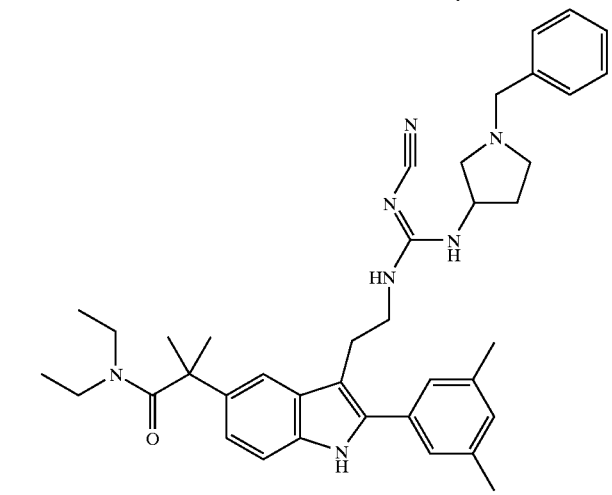 | 1.30 | 632.52(M + H)+ |
Example 2
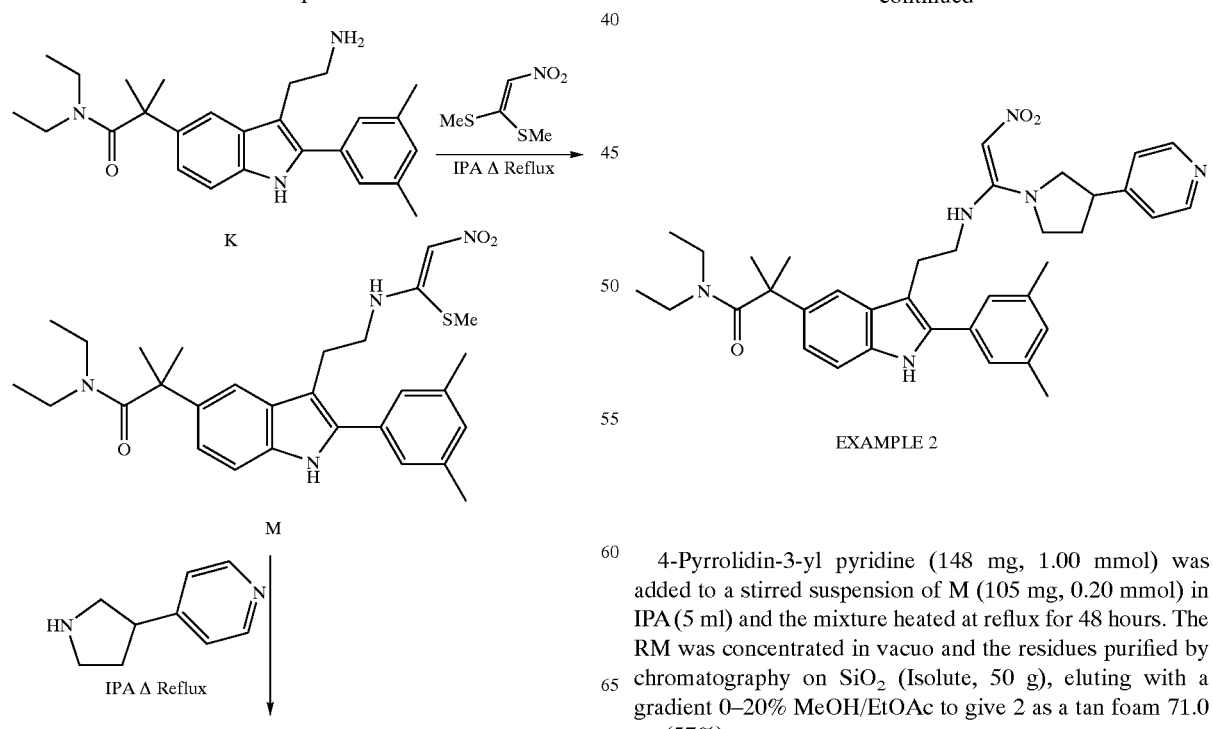
EXAMPLE 2
4-Pyrrolidin-3-yl pyridine (148 mg, 1.00 mmol) was added to a stirred suspension of M (105 mg, 0.20 mmol) in IPA (5 ml) and the mixture heated at reflux for 48 hours. The RM was concentrated in vacuo and the residues purified by chromatography on SiO₂ (Isolute, 50 g), eluting with a gradient 0–20% MeOH/EtOAc to give 2 as a tan foam 71.0 mg(57%).

¹H NMR (300 MHz, CDCl₃) 0.45–0.65 (m,3H); 0.85–1.05 (m,3H); 1.45 (d,6H); 1.70–1.90 (m,1H); 2.00–2.20 (m,1H); 2.20 (s,6H); 2.60–2.90 (m,2H); 3.00–3.30 (m, 8H); 3.30–3.50 (m,3H); 6.28 (s,1H); 6.80–7.00 (m,6H); 7.10–7.25 (m,2H); 8.05 (s,1H); 8.37 (d,2H); 9.90 (t,1H).

MS (ES⁺) m/z (M+H)⁺623.28
MS (ES⁻) m/z (M−H)⁻621.23

Preparation of Intermediate M 1,1 Bis(methylthio)-2-nitroethylene (515 mg,3.1 mmol) was added to a stirred solution of K (1.1 g, 2.72 mmol) in CH₃CN (70 ml) and heated at reflux for 18 hours. The RM was concentrated in-vacuo and the crudes purified by chromatography on SiO₂ (Merck 9385), eluting with 5% MeOH/CH₂Cl₂ to give M as a yellow foam 1.4 g(98%).

¹H NMR (300 MHz, CDCl₃) 0.60–0.80 (m,3H); 1.05–1.25 (m,3H); 1.60 (s,6H); 2.38(s,6H); 2.80–3.05 (m,2H); 3.25–3.50 (m, 4H); 3.68 (q,2H); 6.42 (s,1H); 7.05 (s,1H); 7.06–7.15 (m,3H); 7.32 (d,1H); 7.45 (s,1H); 8.11 (s,1H).

MS (ES⁺) m/z (M+H)⁺523.44
MS (ES⁻) m/z (M−H)⁻521.49

Following a procedure similar to that described in Example 2, the following compound was prepared.

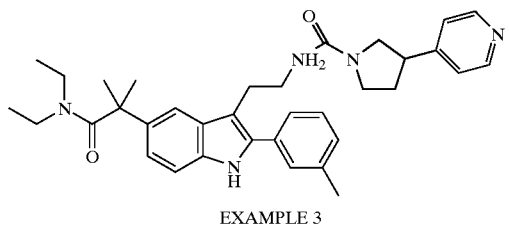

EXAMPLE 3

A solution of K (see Example 1) (100 mg, 0.25 mmol) and Diisopropyl ethylamine (36.0 mg,0.25 mmol) in CH₂Cl₂ (1 ml) was added to a solution of Triphosgene (29.7 mg, 0.10 mmol) in CH₂Cl₂ (1 ml) and the mixture stirred for 15 minutes. A solution of Diisopropylethylamine (36.0 mg, 0.25 mmol) and 4-Pyrrolidin-3-yl pyridine (37.0 mg,0.25 mmol) in CH₂Cl₂ (1 ml) was added and the mixture stirred for 60 hours. The RM was concentrated in-vacuo and the

| STRUCTURE | EXAMPLE | MS (ES)+ |
|---|---|---|
| ![structure] | 2.01 | 597.57(M + H)+ |

Example 3

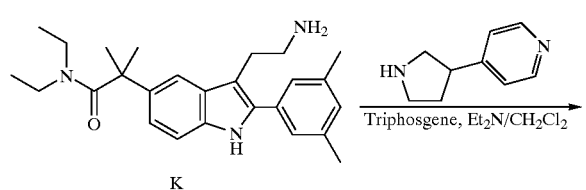

residues purified by chromatography on SiO₂ (Isolute, 50 g), eluting with a gradient 0–10% MeOH/CH₂Cl₂ to give Example 3 as a pale yellow foam 88.0 mg(60%).

¹H NMR (300 MHz, CDCl₃) 0.60–0.80 (m,3H); 1.00–1.30 (m,3H); 1.60 (s,6H); 1.80–2.00 (m,1H); 2.15–2.30 (m,1H); 2.35 (s,6H); 2.80–3.00 (m,2H); 3.05–3.45 (m, 8H); 3.50–3.70 (m,3H); 4.20 (m,1H); 6.85 (s,1H); 7.00–7.10 (m,3H); 7.22 (s,2H); 7.30 (d,1H); 7.45 (d,1H); 8.12 (s,1H); 8.50 (d,2H).

MS (ES⁺) m/z (M+H)⁺580.72
MS (ES⁻) m/z (M−H)⁻578.77

Following a procedure similar to that described in Example 3, examples 3.01 to 3.06 were prepared.

| STRUCTURE | EXAMPLE | MS (ES)+ |
|---|---|---|
| 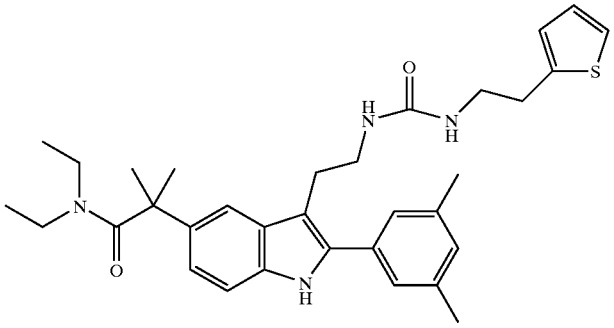 | 3.01 | 559.56(M + H)+ |
| 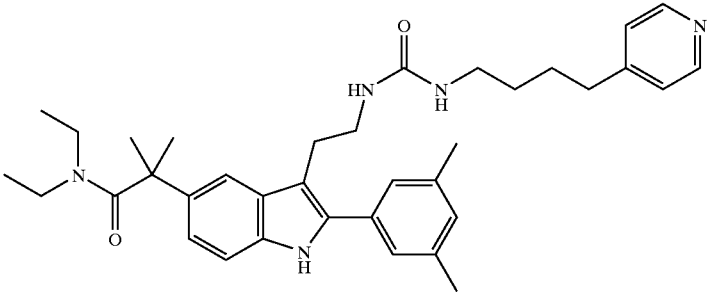 | 3.02 | 582.3(M + H)+ |
| 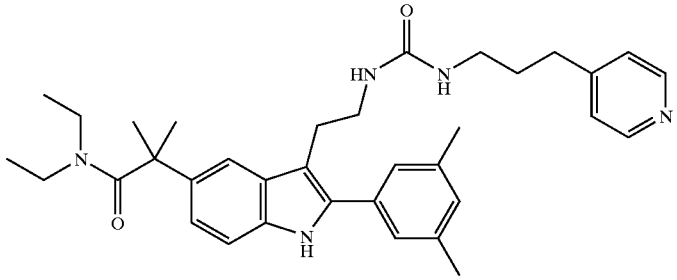 | 3.03 | 568.71(M + H)+ |
| 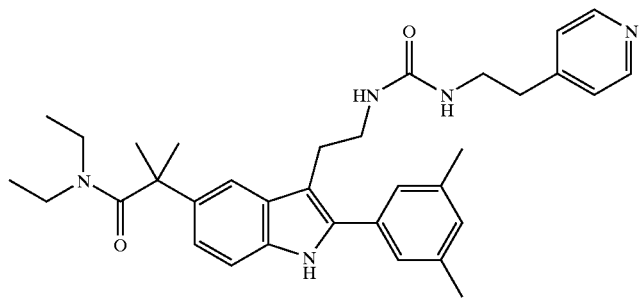 | 3.04 | 554.68(M + H)+ |
| 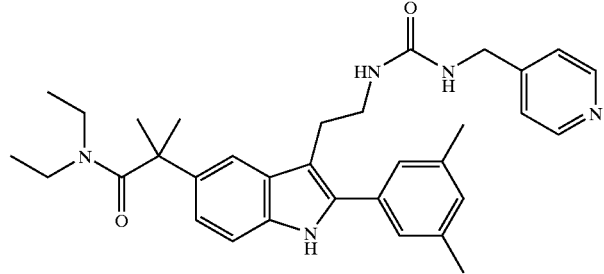 | 3.05 | 540.68(M + H)+ |

-continued

| STRUCTURE | EXAMPLE | MS (ES)+ |
|---|---|---|
| 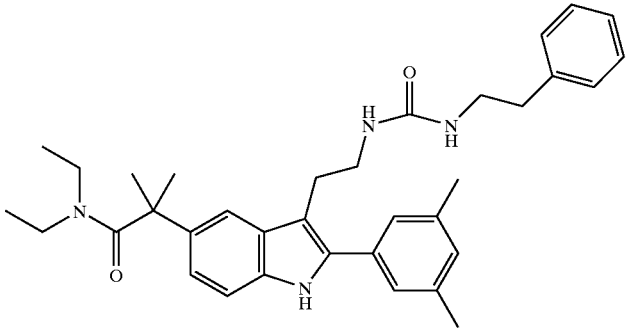 | 3.06 | 553.38(M + H)+ |

Example 4

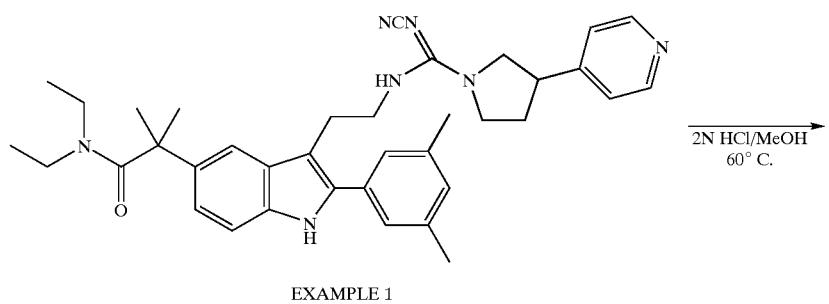

EXAMPLE 1

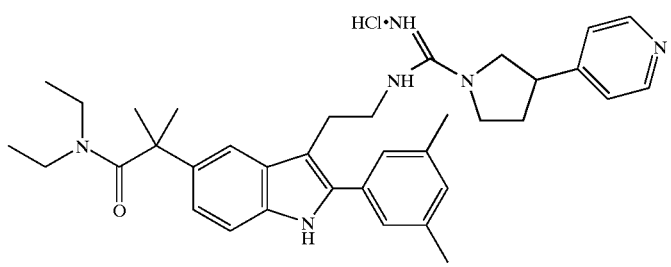

EXAMPLE 4

2N HCl (5 ml) was added to a stirred solution of Example 1 (150 mg, 0.22 mmol) in MeOH (5 ml) the resulting mixture was heated at 60° C. for 18 hours. The RM was evaporated to dryness and the residues partitioned between saturated NaHCO$_3$ (100 ml) and EtOAc (3×25 ml). Combined organics were concentrated in vacuo and the crudes purified by flash chromatography on SiO$_2$ (Isolute, 50 g), eluting a gradient 0–25% MeOH/CH$_2$Cl$_2$ to give Example 4 as a white solid 55.6 mg (38.0%).

$^1$H NMR (300 MHz, DMSO-D$_6$) 0.50–0.80 (m,3H); 0.90–1.10 (m,3H); 1.45 (s,6H); 1.80–2.10 (m,1H); 2.20–2.40 (m,1); 2.30 (s,6H); 2.70–2.95 (m,2H); 3.05–3.55 (m, 10H); 3.55–3.70 (m,1H); 6.90 (s,1H); 7.00 (s,1H); 7.15–7.45 (m,7H); 7.50 (s,2H); 8.50 (d,2H); 11.15 (s,1H).

MS (ES$^+$) m/z (M+H)$^+$579.5

MS (ES$^-$) m/z (M−H)$^-$577.6

Following a procedure similar to that described in Example 4, the examples 4.01 to 4.05 were prepared.

| | STRUCTURE | MS (ES)+ | ¹H NMR (300MHz, DMSO-D₆ + CD₃COOD) |
|---|---|---|---|
| 4.01 | 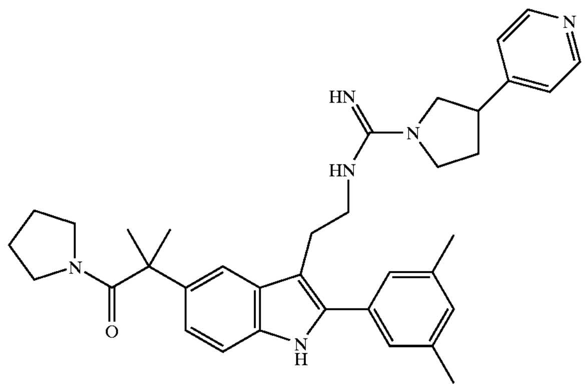 | 577.36 (M + H)⁺ 575.37 (M − H)⁻ | δ1.3–1.7(m, 10H); 1.80–2.05(m, 1H); 2.2–2.4(m, 7H); 2.6–2.8(m, 2H); 3.0–3.5(m, 10H); 3.6(t, 1H); 6.9(d, 1H); 6.95(s, 1H); 7.15–7.35(m, 5H); 7.38(s, 1H); 8.5(d, 2H). |
| 4.02 | 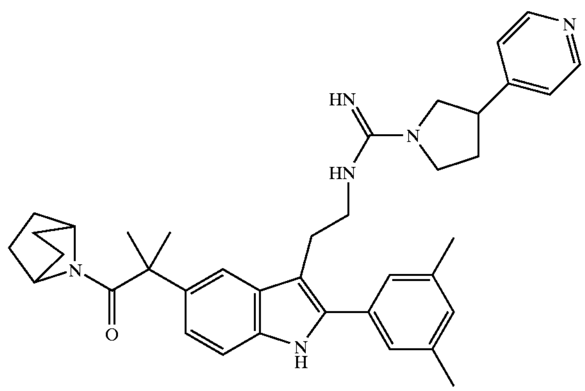 | 603.43 (M + H)⁺ 601.35 (M − H)⁻ | δ1.3–1.7(m, 14H); 1.80–2.05(m, 1H); 2.2–2.4(m, 7H); 3.0–3.6(m, 10H); 3.65(t, 1H); 6.9–7.05(m, 2H); 7.12–7.35(m, 5H); 7.4(s, 1H); 8.5(d, 2H). |
| 4.03 | 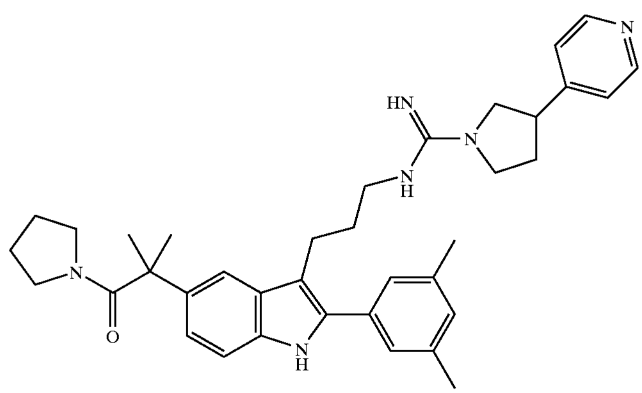 | 591.34 (M + H)⁺ 589.36 (M − H)⁻ | δ1.25–1.65(m, 10H); 1.7–1.9(m, 2H); 1.9–2.1(m, 1H); 2.1–2.4(m, 7H); 2.55–2.75(m, 2H); 2.88(t, 2H); 3.15(t, 2H); 3.2–3.6(m, 6H); 3.7(t, 1H); 6.9(d, 1H); 6.95(s, 1H); 7.15(s, 2H); 7.2–7.4(m, 4H); 8.5(d, 2H). |
| 4.04 | 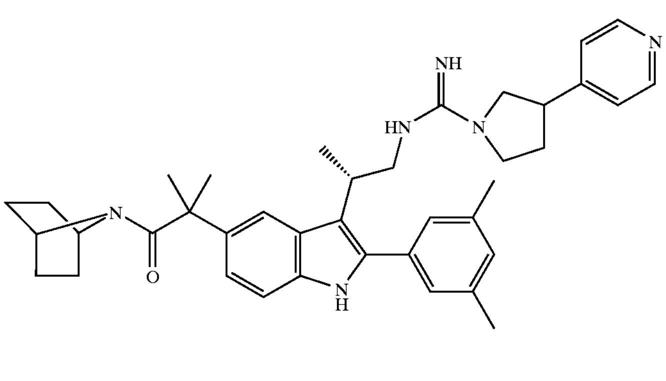 | 615(M − H)⁻ | NMR (400Mz, 373° K, DMSO-d6) δ 1.19(m, 4H); 1.35(m, 4H); 1.43(d, 3H); 1.53(d, 6H); 2.00(m, 1H); 2.33(m, 7H); 3.25–3.73(m, 8H); 4.08(s, 2H); 6.94(broad s, 1H); 6.98 & 7.03(2m, 1H); 7.06(d of d, 1H); 7.14(s, 2H); 7.22(m, 3H); 7.30 & 7.34(2d, 1H); 7.49 & 7.51(2m, 1H); 8.47 & 8.51(2d, 2H); 10.68 & 10.80(2s, 1H). |

-continued

| STRUCTURE | MS (ES)+ | ¹H NMR (300MHz, DMSO-D₆ + CD₃COOD) |
|---|---|---|
| 4.05 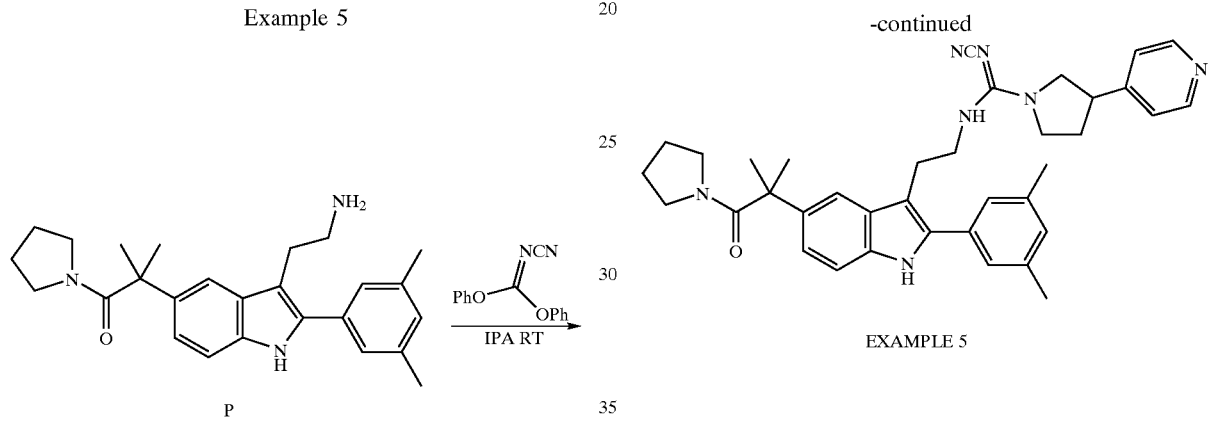 | 629 (M − H)⁻ | NMR(400Mz, 373° K, DMSO-d6) δ 1.12–1.47(m, 9H); 1.50(m, 7H); 2.00(m, 1H); 2.32(m, 7H); 3.15–3.74(complex, 13H); 6.84–7.04 (complex, 3H); 7.14(s, 2H); 7.21 (m, 3H); 7.29 & 7.33(2d, 1H); 7.43 & 7.45(2s, 1H); 8.47 & 8.51(2d, 2H); 10.64 & 10.76(2s, 1H). |

Example 5

4-Pyrrolidin-3-yl pyridine (1.48 g, 10 mmol) was added to a stirred suspension of Q (1.0 g, 2 mmol) in IPA (50 mL) and the mixture heated at reflux for 18 hrs. The RM was concentrated in vacuo and the residues purified by chromatography on $SiO_2$ (Isolute, 50 g), eluting with a gradient 0–10% MeOH/CH₂Cl₂ to give Example 5 as a white foam 860 mg(71%).

¹H NMR (300 MHz, CDCl₃) δ 1.45–1.8 (m,10H+H₂O); 1.80–2.00(m,1H); 2.16–2.30 (m,1H); 2.35 (s,6H); 2.7–2.84 (m,2H); 3.20–3.80 (m, 11H); 4.46–4.56 (m,1H); 6.92–7.48 (m,8H); 8.37 (s,1H); 8.48–8.60 (m,2H).

MS (ES⁺) m/z (M+H)⁺ 602.34

MS (ES⁻) m/z (M−H)⁻ 600.33

Preparation of Intermediate Q

P was treated with Diphenyl cyanocarbonimidate analogously as for the preparation of L (see Example 1) to give Q.

MS (ES⁺) m/z (M+H)⁺ 548.28

MS (ES⁻) m/z (M−H)⁻ 546.27

Preparation of Intermediate P
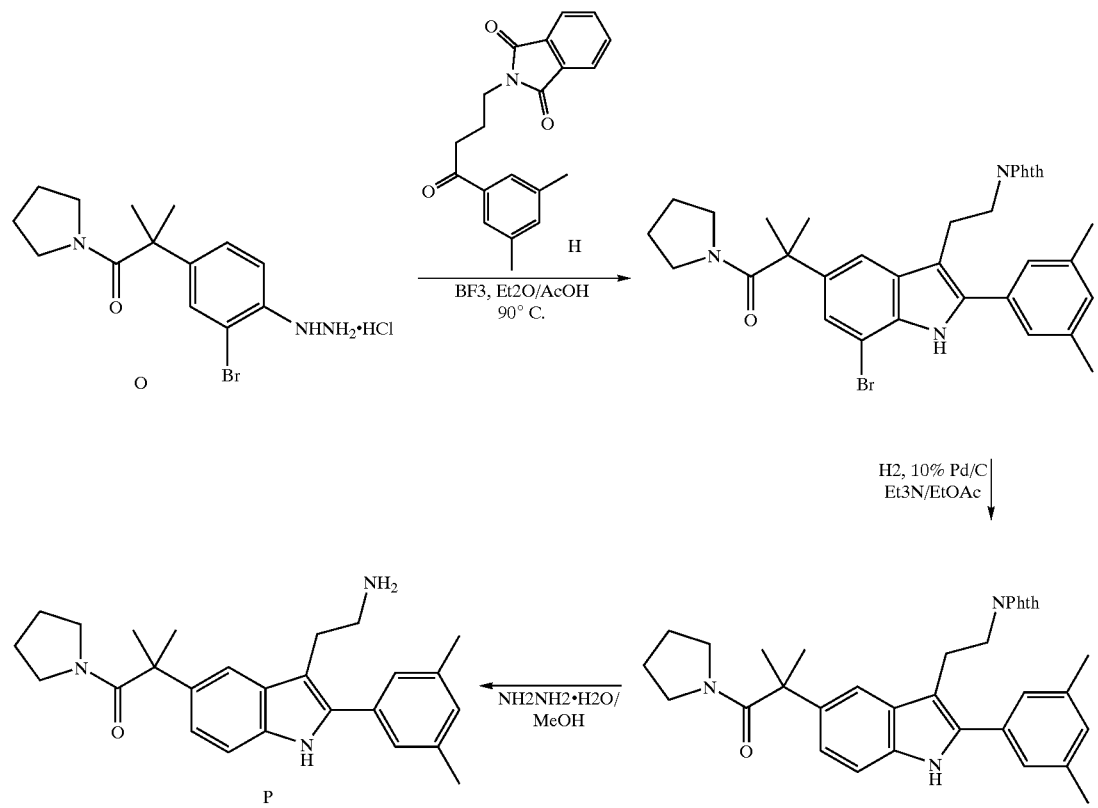
O was treated with the ketone H and deprotected analogously as for the preparation of K (see Example 1) to give P.
$^{1}$H NMR (300 MHz, DMSO-D$_{6}$+CD$_{3}$COOD) δ 1.3–1.7 (m, 10H); 2.35 (s,6); 2.6–2.74 (m,2H); 2.9–3.2 (m,4H); 3.26–3.42 (m,2H); 6.88–6.94 (m,1H); 7.02 (s,1H); 7.18 (s,2H); 7.3 (s,1H); 7.42 (s,1H).
MS (ES$^{+}$) m/z (M+H)$^{+}$404.33
MS (ES$^{-}$) m/z (M−H)$^{-}$402.32
Preparation of Intermediate O
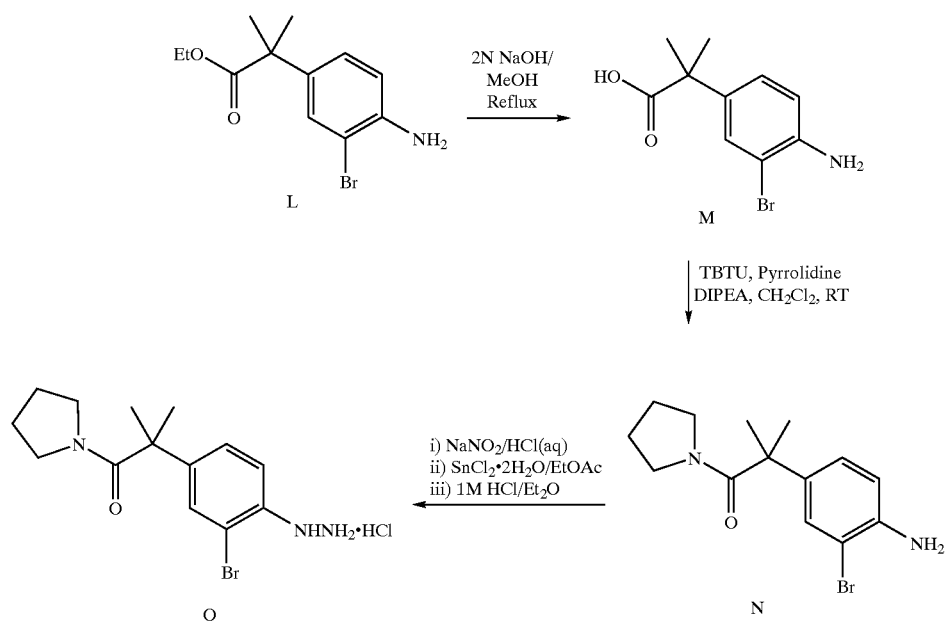

A solution of Ethyl 2-(4-amino-3-bromophenyl)-2-methylpropionate (L) (100 g, 349.6 mmol) in MeOH (400 mL) was treated with 2N NaOH (300 mL, 600 mmol) and the mixture refluxed 18 hrs. The RM was evaporated to dryness and the residues redissolved in water (200 mL).

The pH was adusted to 4 with 2N HCl (aq) and the aqueous was extracted with EtOAc (3×200 mL). The combined organics were washed with brine (2×100 mL), dried (MgSO$_4$), filtered and evaporated to give M as a crystalline solid 86 g (95%).

$^1$H NMR (300 MHz, CDCl$_3$) δ 1.55 (s,6H); 6.70–6.75 (d,1H); 7.1–7.16 (dd,1H); 7.46 (s,1H).

MS (ES$^+$) m/z (M)$^+$258.48

TBTU (1.37 g, 4.268 mmol) was added to a stirred solution of M (1.0 g, 3.87 mmol), pyrrolidine (646 μL, 7.75 mmol) and DIPEA (1.35 mL, 7.75 mmol) in CH$_2$Cl$_2$ (50 mL). The resulting solution was left to stir 64 hrs then washed with water (25 mL). The aqueous was extracted with CH$_2$Cl$_2$ (25 mL) and the combined organics were dried (MgSO$_4$), filtered and evaporated to a yellow solid. The crudes were purified by flash chromatography on SiO$_2$ (Isolute, 50 g). Eluting with a gradient 0–50% EtOAc/CH$_2$Cl$_2$ to give N as a white crystalline solid 1.17 g (96.7%).

$^1$H NMR (300 MHz, CDCl$_3$) δ 1.55 (s,6H); 1.55–1.8 (m,4H+H$_2$O); 2.8 (t,2H); 3.5 (t,2H); 4.02 (s,2H); 6.70(d, 1H); 6.99 (dd,1H); 7.3 (d,1H).

MS (ES$^+$) m/z (M+H)$^+$313.08

N (15.23 g, 48.8 mmol) was diazotised and reduced analogously as for F (see Example 1) to give the HCl salt, O as a white powder 12.83 g(73%).

$^1$H NMR (300 MHz, DMSO-D$_6$+CD$_3$COOD) δ 1.4 (s,6H); 1.3–1.7 (m,4H); 2.6–2.85 (m,2H); 3.2–3.45 (m,2H); 7.0 (d,1H); 7.15 (dd,1H); 7.33 (d,1H).

MS (ES$^+$) m/z (M+H)$^+$327.98

Following a procedure similar to that described in Example 5, the examples 5.01 to 5.06 were prepared.

| | STRUCTURE | MS (ES)+ | $^1$H NMR (300MHz, CDCl$_3$) |
|---|---|---|---|
| 5.01 | 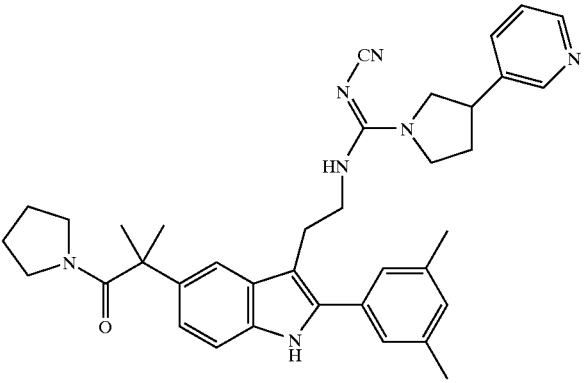 | 602.19 (M + H)$^-$ | δ 1.4–1.8(m, 10H + H$_2$O); 1.80–2.00(m, 1H); 2.15–2.35(m, 1H); 2.35(s, 6H); 2.75(t, 2H); 3.15–3.60(m, 8H); 3.6–3.75(m, 3H); 4.45(t, 1H); 6.95(s,1H); 7.08(dd, 1H); 7.2(s, 2H); 7.2–7.4(m, 2H); 7.4–7.5(m, 2H); 8.3(s, 1H); 8.48(s, 1H); 8.5(d, 1H). |
| 5.02 | 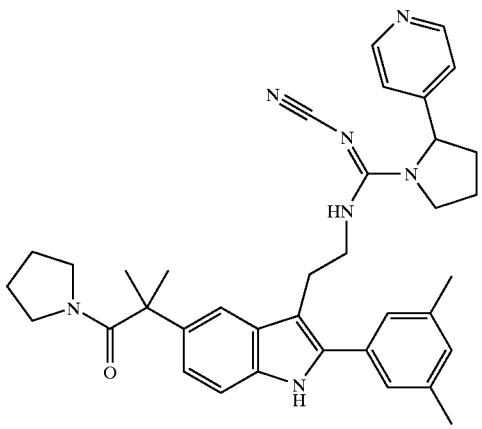 | 602.35 (M + H)$^+$ | δ 1.4–1.9(m, 12H + H$_2$O); 2.1–2.3(m, 1H); 2.4(s, 6H); 2.75(t, 2H; 3.1–3.2(m, 2H); 3.38–3.65(m, 6H); 3.7–3.9(m, 1H); 4.3(t, 1H); 4.6–4.8(m, 1H); 6.72(d, 2H); 7.02(s, 1H); 7.05–7.15(m, 3H); 7.35(d, 1H); 7.42(s, 1H); 8.25(s, 1H); 8.4(d, 2H). |

-continued
| | STRUCTURE | MS (ES)+ | $^1$H NMR (300MHz, CDCl$_3$) |
|---|---|---|---|
| 5.03 | 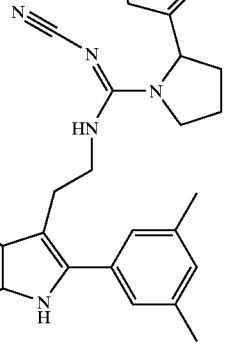 | 602.36 (M + H)$^+$ | δ 1.4–1.8(m, 10H + H$_2$O); 1.8–2.1(m, 2H); 2.1–2.35(m, 1H); 2.4(s, 6H); 2.75(t, 2H); 3.05(t, 2H); 3.4–3.8(m, 7H); 4.7–4.85(m, 1H); 5.4–5.5(m, 1H); 6.98–7.2(m, 6H); 7.3(d, 1H); 7.45(s, 1H); 7.6(t, 1H); 8.1(s, 1H); 8.2–8.3(m, 1H). |
| 5.04 | 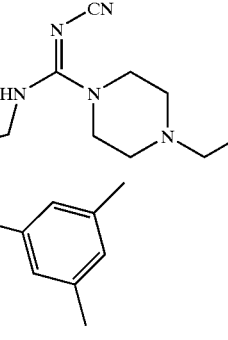 | 631.33 (M + H)$^+$ | δ 1.4–1.8(m, 10H + H$_2$O); 2.2–2.4(m, 10H); 2.75(t, 2H); 3.1–3.2(m, 4H); 3.25(t, 2H); 3.45(s, 2H); 3.45–3.6(m, 2H); 3.6–3.75(m, 2H); 4.4–4.65(m, 1H); 6.98(s, 1H); 7.08(d, 1H); 7.17(s, 2H); 7.21(d, 2H); 7.32(d, 1H); 7.45(s, 1H); 8.28(s, 1H); 8.55(d, 2H). |
| 5.05 | 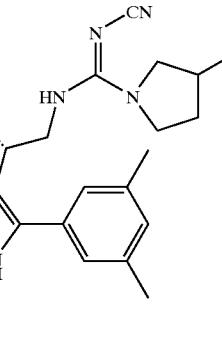 | 642 (M + H)$^+$ | NMR (400Mz, 373° K, DMSO-d6) δ 1.17(m, 5H); 1.35(m, 6H); 1.50(d, 6H); 1.95(m, 1H); 2.27(m, 1H); 2.33(s, 6H); 3.33–3.83(complex, 8H); 4.11(s, 2H); 6.42(s, 1H); 7.01(m, 2H); 7.17(s, 2H); 7.21(d of d, 2H); 7.30(d, 1H); 7.54(s, 1H); 8.48(d of d, 2H; 10.78(s, 1H). |
| 5.06 | 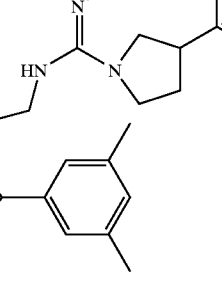 | 656 (M + H)$^+$ | NMR (400Mz, 373° K, DMSO-d6) δ1.15–1.47(m, 10H); 1.50(d, 6H); 1.95(m, 1H); 2.28(m, 1H); 2.33(s, 6H); 3.13–385(complex, 13H); 6.40(s, 1H); 6.94(d, 1H); 6.99(s, 1H); 7.17(s, 2H); 7.21(d, 2H); 7.30(d, 1H); 7.48(s, 1H); 8.48(d, 2H); 10.79(s, 1H). |

Example 6

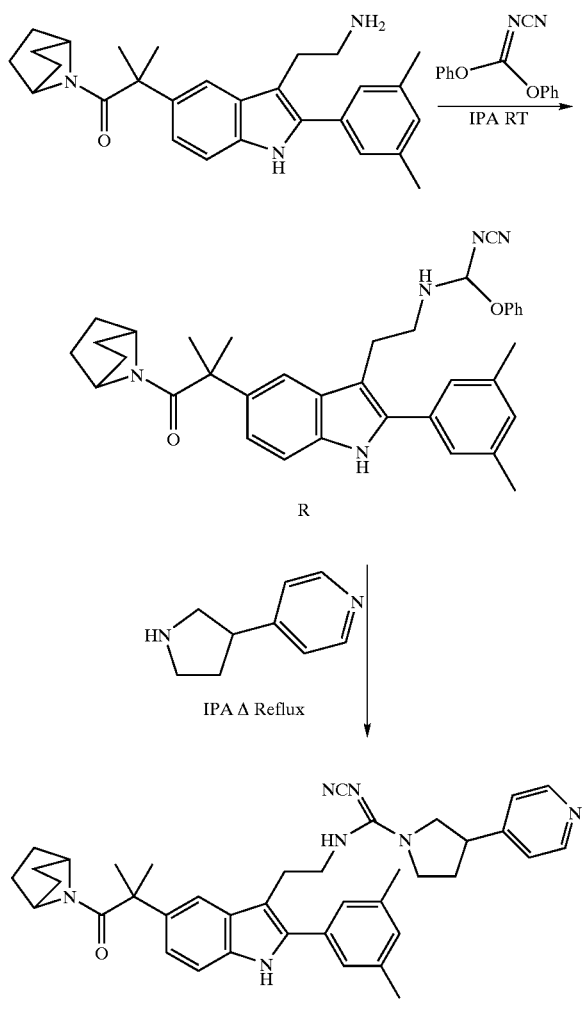

EXAMPLE 6

4-Pyrrolidin-3-yl pyridine (607 mg, 4.1 mmol) was added to a stirred suspension of R (472 mg, 0.82 mmol) in IPA (50 mL) and the mixture heated at reflux for 18 hrs. The RM was concentrated in vacuo and the residues purified by chromatography on $SiO_2$ (Isolute, 50 g), eluting with a gradient 0–10% $MeOH/CH_2Cl_2$ to give Example 6 as a white foam 314 mg(61%).

$^1$H NMR (300 MHz, $CDCl_3$) δ 1.0–1.5 (m,8H); 1.6 (s,6H); 1.85–2.00(m,1H); 2.2–2.35 (m,1H); 2.38 (s,6H); 3.20–3.55 (m, 6H); 3.6–3.8 (m,4H); 4.42–4.52 (m, 1H); 4.6–4.8 (bm,1H); 7.0 (s,1H); 7.07 (d,2H); 7.12–7.2 (m,1H); 7.24 (s,2H); 7.33 (d,1H); 7.48 (s,1H); 8.23 (s,1H); 8.54–8.58 (m,2H).

MS (ES$^+$) m/z (M+H)$^+$628.42
MS (ES$^-$) m/z (M−H)$^-$626.43

Preparation of Intermediate R

7-Azabicyclo[2.2.1]heptane, 7-[2-[3-(2-aminoethyl)-2-(3,5-dimethylphenyl)-1H-indol-5-yl]-2-methyl-1-oxopropyl]-(9CI) (350 mg, 0.815 mmol) was coupled with Diphenyl cyanocarbonimidate analogously as for the preparation of L (see Example 1) to give R,.

$^1$H NMR (300 MHz, $CDCl_3$) δ 1.0–1.45 (m,8H); 1.6 (s,6H); 2.35 (s,6H); 3.10–3.30 (m,2H); 3.5–3.64 (m,1H); 3.64–3.8 (m,2H); 4.6–4.8 (m,1H), 6.14–6.22(m,1H); 6.74–6.82 (d,1H); 7.05 (s,1H); 7.08–7.14 (d,1H); 7.16 (s,2H); 7.2–7.45 (m,5H); 7.5 (s,1H); 8.14 (s,1H).

MS (ES$^+$) m/z (M+H)$^+$628.42
MS (ES$^-$) m/z (M−H)$^-$626.43

Example 7

Example 7

7-Azabicyclo[2.2.1]heptane, 7-[2-[3-(2-aminoethyl)-2-(3,5-dimethylphenyl)-1H-indol-5-yl]-2-methyl-1-oxopropyl]-(9CI) (215 mg, 0.5 mmol) was coupled with 4-Pyrrolidin-3-yl pyridine under the same conditions employed in Example 3 to give Example 7 as a colourless foam, 24 mg (8%).

$^1$H NMR (300 MHz, $CDCl_3$) δ 1.0–1.5 (m,8H); 1.6 (s,6H); 1.5–1.7(m,2H); 1.8–2.0(m,1H); 2.2–2.35 (m,1H); 2.36 (s,6H); 3.10–3.8 (m,8H); 4.24–4.32 (t,1H); 4.6–4.8 (m,1H); 6.96 (s,1H); 7.06–7.12 (m,2H); 7.14 (s,1H) 7.22 (s,2H); 7.3–7.34 (d,1H); 7.52 (s,1H); 8.23 (s,1H); 8.4–8.6 (m,2H).

MS (ES$^+$) m/z (M+H)$^+$604.36
MS (ES$^-$) m/z (M−H)$^-$602.44

Example 8

Example 8

2-Azabicyclo[2.2.2]octane,2-[2-[3-[(1S)-2-amino-1-methylethyl]-2-(3,5-dimethylphenyl)-1H-indol-5-yl]-2-methyl-1-oxopropyl]-(9CI) (250 mg, 0.547 ml) was coupled with 4-Pyrrolidin-3-yl pyridine under the same conditions employed in Example 3 to give Example 8 as a white foam, 99 mg (28%).

¹H NMR (300 MHz, CDCl₃) δ 1.0–1.75 (m,17H); 1.75–2.0 (m,2H); 2.1–2.4 (m,1H); 2.35 (s,6H); 3.05–3.55 (m,9H); 3.55–3.7 (m,1H); 3.7–3.9 (m,1H); 4.05–4.2 (m,1H); 6.9–7.2 (m,6H); 7.33 (d,1H); 7.52 (s,1H); 8.06 (s,1H); 8.4–8.6 (m,2H).

MS (ES⁺) m/z (M+H)⁺632.23

MS (ES⁻) m/z (M–H)⁻630.20

Example 9

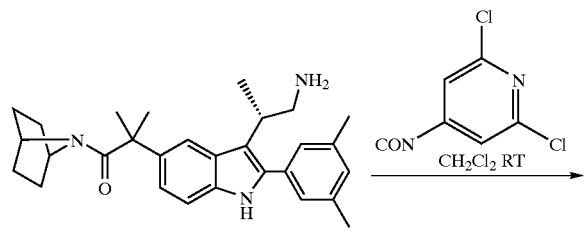

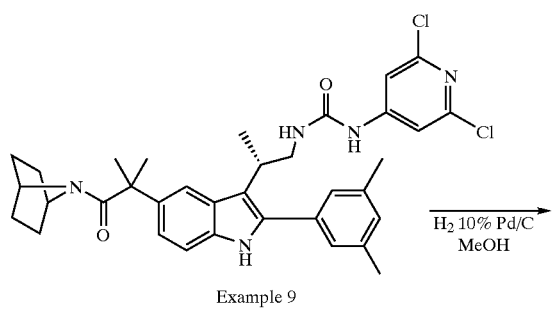

Example 9

A solution of 7-Azabicyclo[2.2.1]heptane, 7-[2-[3-[(1S)-2-amino-1-methylethyl]-2-(3,5-dimethylphenyl)-1H-indol-5-yl]-2-methyl-1-oxopropyl]-(9CI) (150 mg, 0.338 mmol) in CH₂Cl₂ (5 mL) was treated with 2,6-Dichloro-pyridin-4-Yl isocyanate (70 mg, 0.37 mmol) and the resulting mixture left to stir for 18 hrs. The RM was purified by flash chromatography on SiO₂ (Varian, 20 g), eluting with a gradient 0–50% EtOAc/CH₂Cl₂ to give Example 9 as a white foam 120 mg(56%).

¹H NMR (300 MHz, CDCl₃) δ 1.0–1.8 (m,17H); 2.35 (s,6H); 3.5–3.65 (m,3H); 3.65–3.8 (m,1H); 4.4–4.6 (m,1H); 5.8–5.95 (m,1H); 7.0 (s,1H); 7.05 (d,1H); 7.15 (s,2H); 7.2–7.5 (m,4H); 8.05 (s,1H); 8.6–8. (bs,1H).

MS (ES⁺) m/z (M+H)⁺632.08

MS (ES⁻) m/z (M–H)⁻630.12

Example 10

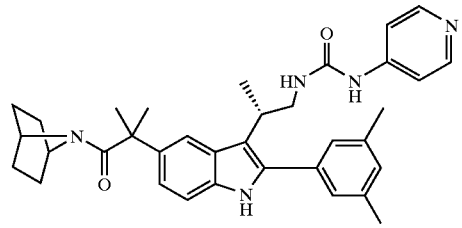

Example 10

A mixture of Example 9 (100 mg, 0.158 mmol) and 10% Pd/C (30 mg) in MeOH (5 mL) and Et₃N (1mL) was stirred under an atmosphere of H₂ for 18 hrs. The mixture was filtered evaporated and the crudes were purified by flash chromatography on SiO₂ (Varian, 20 g), eluting with a gradient 0–10% MeOH/CH₂Cl₂ to give Example 10 as a white foam, 56.4 mg (63.2%).

¹H NMR (300 MHz, CDCl₃) δ 1.0–1.7 (m,14H); 1.75 (s,3H); 2.35 (s,6H); 3.4–3.8 (m,4H); 4.4–4.6 (m,1H); 5.8–5.90 (m,1H); 6.95 (s,1H); 7.05 (d,1H); 7.12 (s,2H); 7.2–7.35 (m,3H); 7.5 (s,1H); 8.18 (d,2H); 8.3 (bs,1H); 8.35 (bs,1H).

MS (ES⁺) m/z (M+H)⁺564.49

MS (ES⁻) m/z (M–H)⁻562.22

Example 11

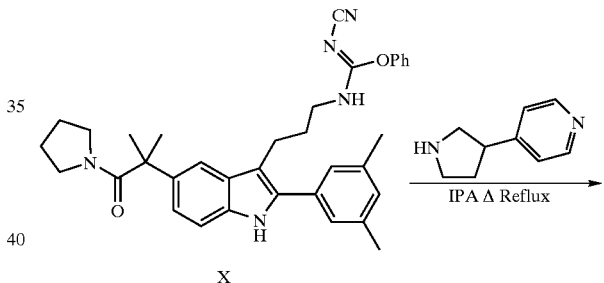

Example 11

Intermediate X (675 mg, 1.2 mmol) was treated with 4-Pyrrolidin-3-yl pyridine analogously as for Example 8 to give Example 11 as a white foam 576.4 mg(78%).

¹H NMR (300 MHz, CDCl₃) δ 1.45–1.8 (m,10H); 1.85–2.1(m,3H); 2.2–2.45 (m,7H); 2.8 (t,2H); 3.0 (t,2H); 3.0–3.70 (m, 9H); 4.35 (t,1H); 6.9 (s,1H); 6.95–7.13(m,3H); 7.17 (s,2H); 7.25(d,1H); 7.44 (s,1H); 8.32 (s,1H); 8.55 (d,2H).

MS (ES⁺) m/z (M+H)⁺616.73

MS (ES⁻) m/z (M–H)⁻614.74

Preparation of Intermediate X
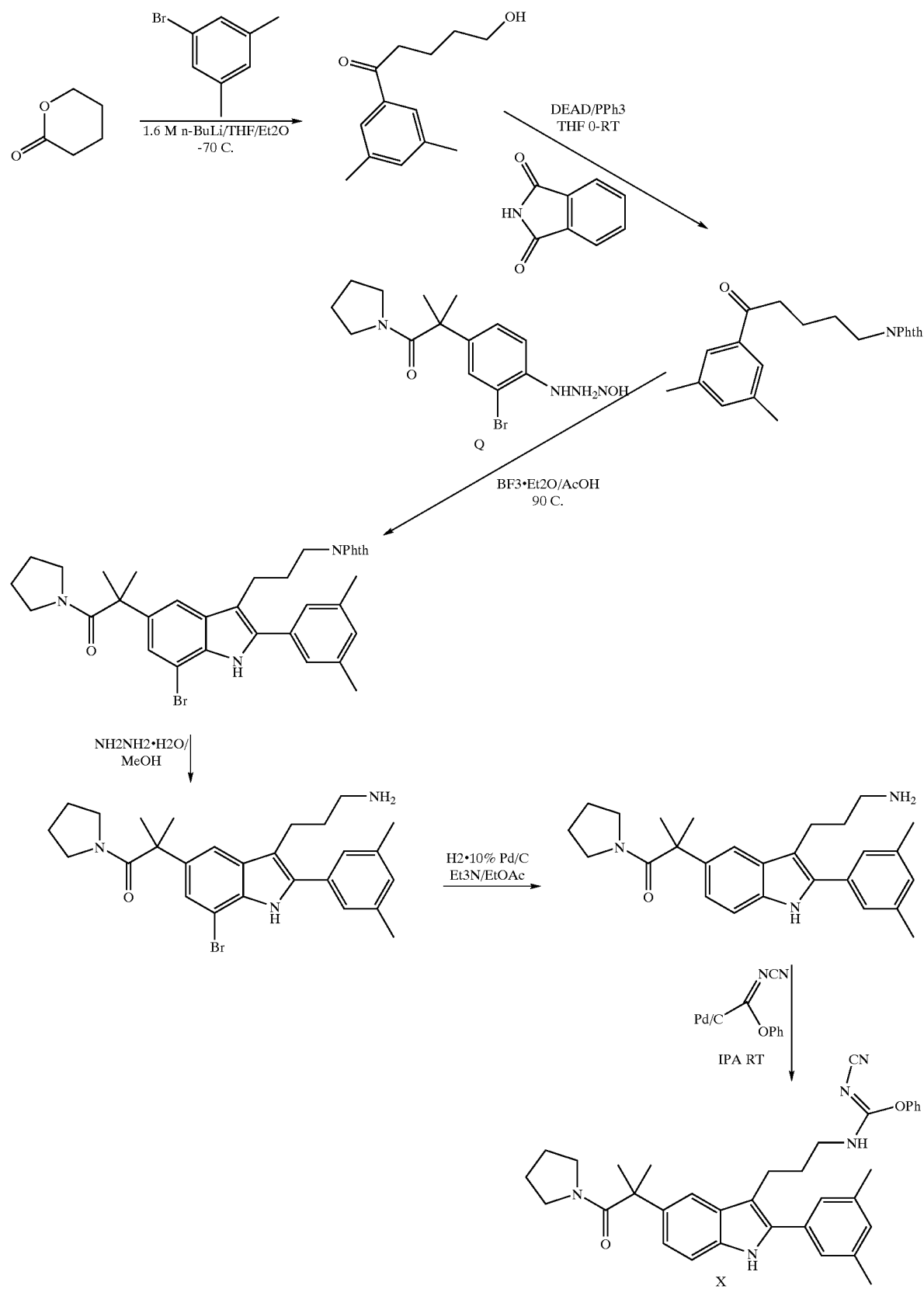
Scheme 18

δ-Valerolactone was modified analogously as for the preparation of Q (see Example 5) to give the homologous tryptamine derivative X.

¹H NMR (300 MHz, CDCl$_3$) δ 1.45–1.58 (m,2H); 1.59–1.73 (m,8H); 1.95–2.1 (m,2H); 2.38 (s,6H); 2.70–2.84 (m,2H); 2.88–3.10 (m,2H); 3.25–3.5 (m,2H); 3.5–3.6 (m,2H); 6.3–6.42 (m,1H); 6.90–7.50 (m,11H); 8.20 (s,1H).
MS (ES$^+$) m/z (M+H)$^+$562.50
MS (ES$^-$) m/z (M–H)$^-$560.51

Following a procedure similar to that described in Example 11, the example 11.01 was prepared.

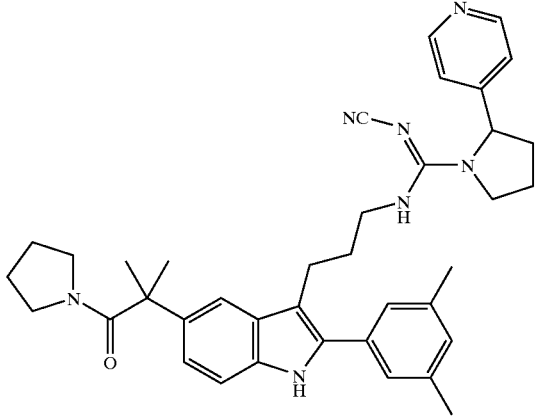

| | STRUCTURE | MS (ES)+ | ¹H NMR(300MHz, CDCl$_3$) |
|---|---|---|---|
| 11.01 | 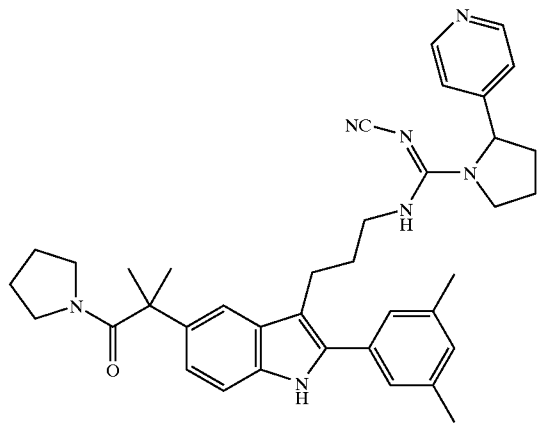 | 616.75 (M + H)$^+$ 614.77 (M − H)$^-$ | δ 1.4–2.0(m, 15H); 2.2–2.50(m, 7H); 2.7–3.0(m, 4H); 3.25–3.65(m, 6H); 4.35(t, 1H); 4.80–4.95(m, 1H); 6.95(d, 2H); 7.05(s, 1H); 7.10(dd, 1H); 7.15(d, 2H); 7.33(d, 1H); 7.4(s, 1H); 8.25(s, 1H); 8.45(d, 2H). |

Example 12

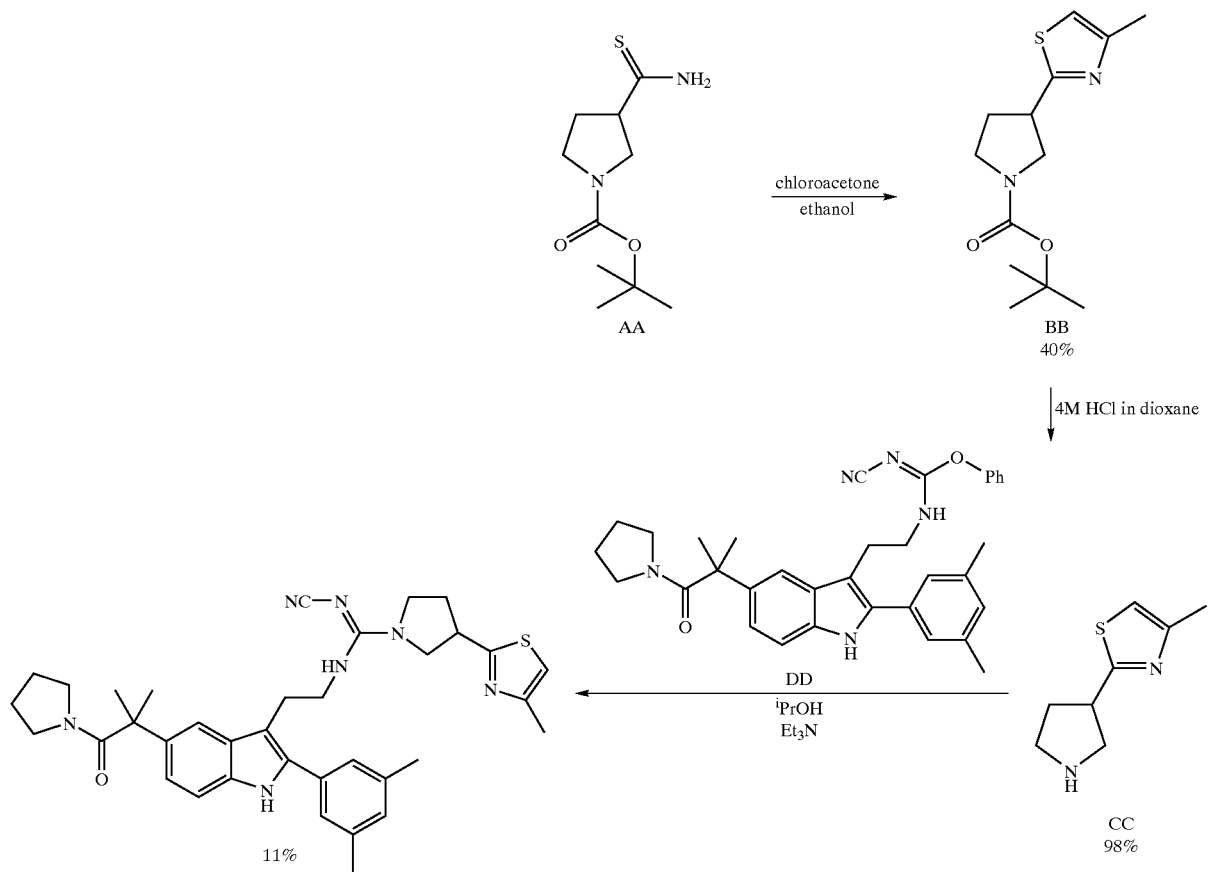

Example 12

Intermediate DD (70.9 mg, 0.13 mmols) and Intermediate CC (53.8 mg, 0.26 mmols) were suspended in iso-propanol (5 ml). Triethylamine (0.06 ml, 0.43 mmols) was added and the reaction mixture was heated to 90° C. for 3 days. The reaction mixture was allowed to cool then concentrated in vacuo. The residue was purified by Prep LCMS to give compound 5 (9.2 mg 0.01 mmols) as a white solid.

Mass spectrum: [MH]⁺=622.46

[M−H]⁻=620.33

$^1$H NMR −300 MHz, CDCl$_3$ δ(ppm); −8.14 (1H, s); 7.46 (1H, s); 7.32−7.30 (1H, d); 7.21 (2H, s); 7.09−7.07 (1H, d); 7.00 (1H, s); 6.78 (1H, s); 4.44−4.37 (1H, m); 3.71−3.61 (4H, m); 3.59−3.47 (4H, m); 3.44−3.36 (2H, m); 3.29−3.22 (2H, m); 2.82−2.74 (2H, m); 2.40 (3H, s); 2.37 (6H, s); 1.73−1.65 (2H, m); 1.60 (6H, s); 1.57−1.51 (2H, m)

Preparation of Intermediate DD

Intermediate DD was prepared using a method analogous to the preparation of Intermediate X (see Example 11).

Preparation of Intermediate CC

Intermediate BB (0.43 g, 1.6 mmols) was dissolved in 1,4-dioxane (40 ml). 4M HCl in dioxane (2 ml, 8 mmols) was added. The reaction mixture was stirred at room temperate under a nitrogen atmosphere for 2 days. More 4M HCl in dioxane (2 ml, 8 mmols) was added and after sting at room temperature for a further 3.5 days the reaction mixture was concentrated in vacuo. Ether was added to the residue. The ether was removed under reduced pressure and the resulting gum was azetroped with toluene (×3). The resulting solid was dried in a desiccator to give Intermediate CC (0.32 g, 1.57 mmols) as the HCl salt.

Mass Spectrum: [MH]⁺=169.14

1H NMR −300 Mz, d$_6$-DMSO+d$_4$-acetic acid δ(ppm): −7.20 (1H, s), 3.95−3.83 (1H, m), 3.65−3.54 (1H, m); 3.37−3.20 (4H, m); 2.44−2.36 (1H, m); 2.33 (3H, s); 2.13−2.03 (1H, m)

Preparation of Intermediate BB

Intermediate AA (0.97 g, 4.2 mmols) was dissolved in ethanol (35 ml). Chloroacetone (0.4 ml, 5.0 mmols) was added and the reaction mixture heated to reflux. After 7 hours the reaction mixture was allowed to cool and concentrated in vacuo. The residue was taken up in a mixture of dichloromethane and water. The organic phase was removed, washed with water, dried (MgSO$_4$), filtered and concentrated in vacuo to give Intermediate BB (0.43 g, 1.6 mmols).

Mass Spectrum:—mass ion not observed

1H NMR −300 MHz, d$_6$-DMSO δ(ppm):−7.12 (1H, s); 3.78−3.64 (2H, m); 3.45−3.32 (1H, m); 2.31 (3H, s); 2.28−2.20 (2H, m), 2.11−1.93 (2H, m); 1.39 (9H, m)

Preparation of Intermediate AA

For the synthesis of Intermediate AA the reader is referred to Journal of Medicinal Chemistry., 1990, Volume 33, Page 2052

Example 13

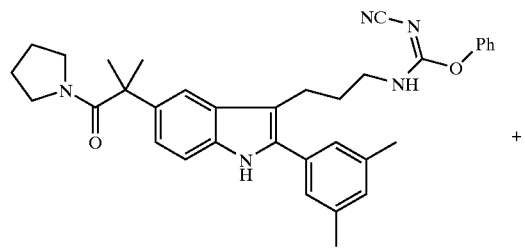

+

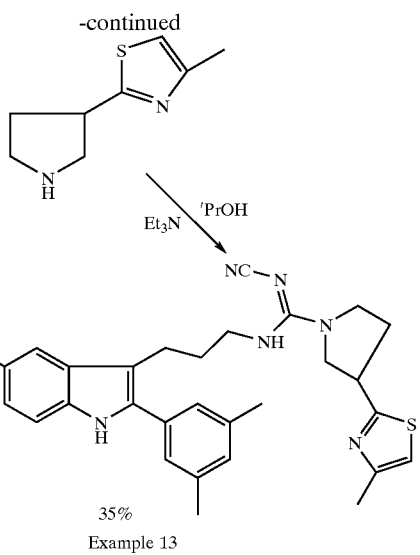

Example 13

Example 13 was prepared using a method analogous to Example 12.

Example 14

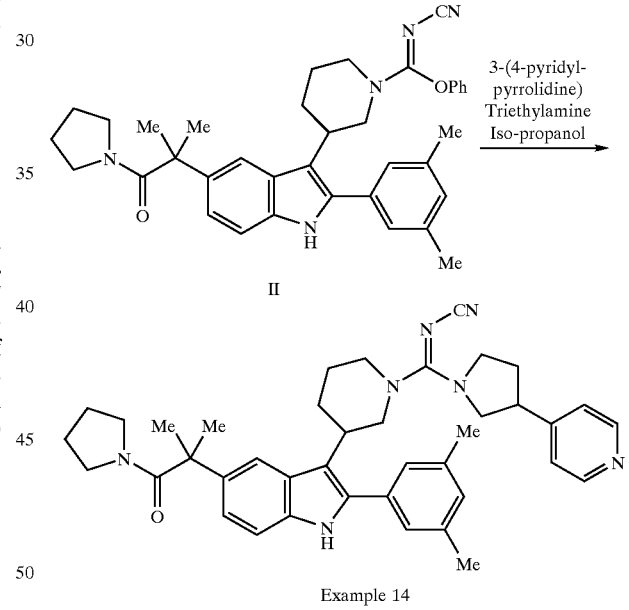

Example 14

A mixture of Intermediate EE (0.66 grms), 3-(4-pyridyl-pyrrolidine)(0.9 grms) and triethylamine(1 ml.) in iso-propanol(40 mls.) was stirred and heated at 90 degs. for 48 hours. The reaction was cooled and evaporated to dryness. The residue was purified by flash column chromatography on silica eluting with methanol/dichloromethane(1:20 and 1:10) to give Example 14 as a pale yellow foam(0.21 grms.).

$^1$H NMR (d-6-DMSO, δ values) 1.29−1.69 (m, 6H); 1.47 (d, 6H); 1.75−2,40(m, 4H); 2.30 (d, 6H); 2.60−2.85 (m, 2H); 2.95−3.90 (m, 12H); 6.87 (m, 1H); 7.00 (d, 1H); 7.10 (s, 1H); 7.14 (s, 1H); 7.21−7.35(m, 3H); 7.50 (d, 1H); 8.46 (d, 2H); 11.11 & 11.14 (2br.s, 1H).

MS(ES⁺) m/z (M+H)⁺642.56

Preparation of Intermediate II
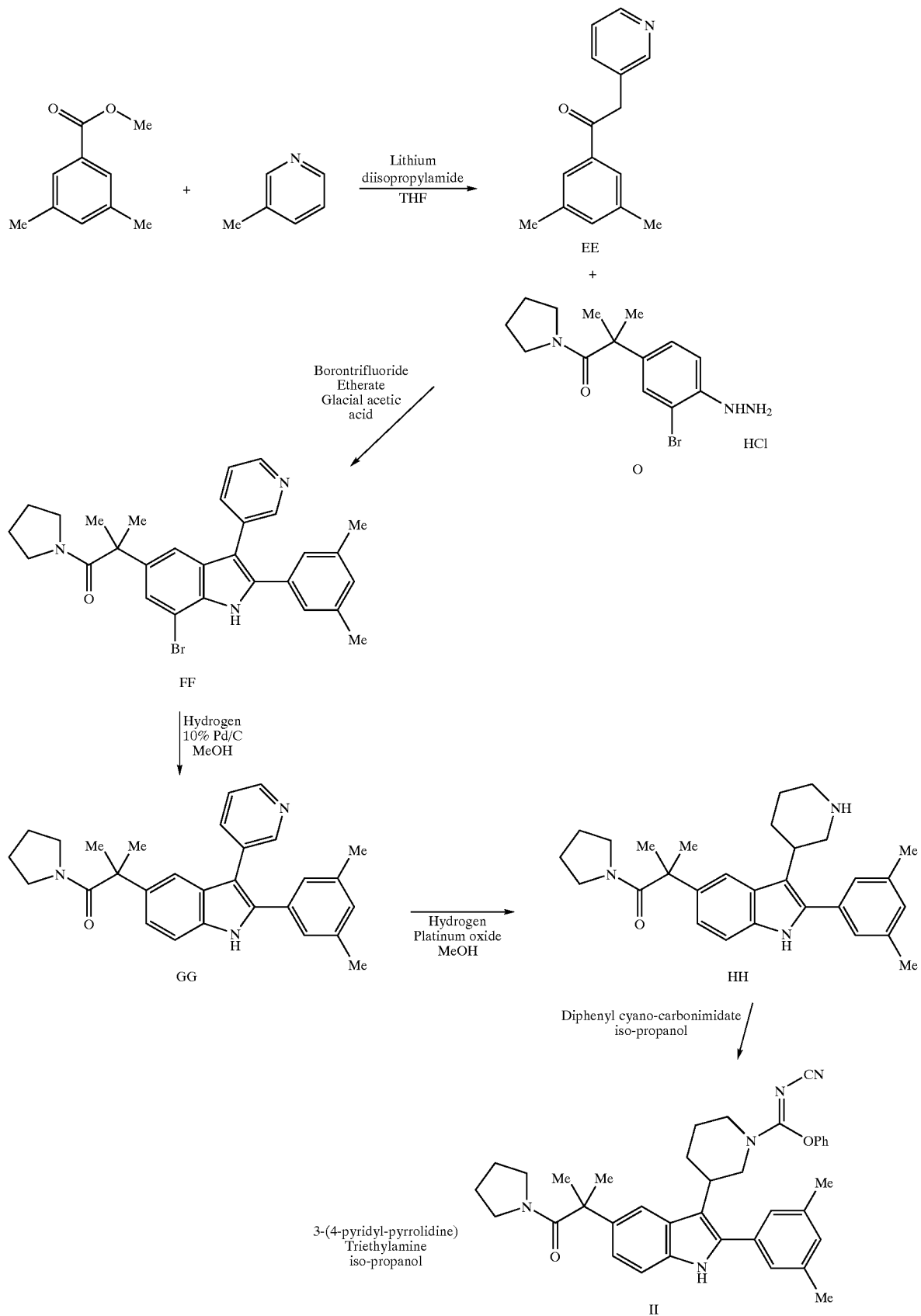

A solution of lithium diisopropylamide(31 mls, 2M in THF) was added dropwise to a stirred solution of 3-picoline (5.7 grms.) in THF(100 mls.) cooled to 0 degs. under a nitrogen atmosphere. After 30 mins. at this temperature a solution of methyl 3,5-dimethylbenzoate(5 grms.) in THF (20 mls.) was added maintaining the temperature below 0 degs. during the addition and for 1 hour afterwards. The reaction was quenched with saturated ammonium chloride (100 mls.) and extracted with ethyl acetate. The extracts were dried and evaporated to dryness. The residue was purified by flash column chromatography on silica eluting with ethyl acetate/iso-hexane(1:1) to give Intermediate EE as a yellow oil which slowly crystallized(3.2 grms).

$^1$H NMR (d-6-DMSO, δ values) 2.33 (s, 6H); 4.41 (s, 2H); 7.25–7.37 (m, 2H); 7.6–7.7 (m, 3H); 8.42 (m, 2H).

MS(ES$^+$) m/z (M+H)$^+$226.02

A mixture of Intermediate EE (3.0 grms.), Intermediate O (see Example 5)(5.8 grms.), glacial acetic acid(50 mls,) and boron trifluoride diethyl etherate(5 mls.) was stirred and heated at 95–100 degs. for 18 hours under a nitrogen atmosphere. The reaction mixture was cooled and the acetic acid was evaporated away. The residue was basified with saturated sodium bicarbonate solution and extracted with ethyl acetate. The extracts were dried, evaporated to dryness and the residue purified by flash column chromatography on silica eluting with ethyl acetate/iso-hexane(1:1, 4:1) and ethyl acetate to give Intermediate FF (5.00 grms.) as a yellowish solid.

$^1$H NMR (d-6-DMSO, δ values) 1.35–1.69 (m, 4H); 1.40 (s, 6H); 2.2 (s, 6H); 2.64–2.8 (m, 2H); 3.21–3.40 (m, 2H); 6.98 (s, 1H); 7.03 (s, 2H); 7.14 (s, 1H); 7.27 (s, 1H); 7.35–7.44 (m, 1H); 7.66 (d, 1H); 8.40–8.50 (m, 2H); 11.63 (br.s, 1H).

MS(ES$^+$) m/z (M+H)$^+$515.97, 517.96

A mixture of Intermediate FF (5.00 grms.) and 10% palladium on carbon(1.3 grms.) in methanol(200 mls.) was stirred under an atmosphere of hydrogen for 18 hours. The reaction was filtered and the filtrate evaporated to dryness, basified with saturated sodium bicarbonate and extracted with ethyl acetate, the extracts dried and evaporated to give Intermediate GG as a white solid(3.9 grms.).

$^1$H NMR (d-6-DMSO, δ values) 1.36–1.70 (m, 4H); 1.46 (s, 6H); 2.23 (s, 6H); 2.70 (m, 2H); 3.35 (m, 2H); 6.95–7.10 (m, 4H); 7.43 (m, 2H); 7.91 (m, 1H); 8.29 (d, 1H); 8.7 (m, 2H); 11.85 (br.s, 1H).

MS(ES$^+$) m/z (M+H)$^+$438.03

A mixture of Intermediate GG (3.5 grms.) and platinum oxide(800 mgs.) was stirred under an atmosphere of hydrogen for 8 hours. The catalyst was filtered off and the filtrate evaporated to dryness to give a white solid. Recrystallisation from ethyl acetate gave the starting material(0.45 grms.). The mother liquors were evaporated to give (5) as a white solid(2.9 grms.). This was converted to the hydrochloride salt by addition of ethereal HCl to a solution of Intermediate HH in ethyl acetate and the solid isolated by centrifugation.

$^1$H NMR (d-6-DMSO, δ values) 1.32–2.00 (m, 7H); 1.50 (d, 6H); 2.00–2.10 (m, 1H); 2.36 (s, 6H); 2.62–2.80 (m, 2H); 2.90–3.11 (m, 1H); 3.20–3.48 (m, 6H); 6.89 (d, 1H); 7.05 (s, 1H); 7.10 (s, 2H); 7.30 (d, 1H).); 7.58 (s, 1H); 8.83 (br.s, 2H); 11.20 (br.s, 1H).

MS(ES$^+$) m/z (M+H)$^+$444.04

A mixture of Intermediate HH (0.5 grms.), diphenyl cyano-carbonimidate(0.45 grms.) in iso-propanol(50 mls.) was stirred at ambient temperature for 18 hours. It was then evaporated to dryness and the residue purified by flash column chromatography on a silica column eluting with ethyl acetate/iso-hexane(4:1) to give Intermediate II as a white foam(0.66 grms.).

$^1$H NMR (d-6-DMSO, δ values) 1.20–1.72 (m, 8H); 1.49 (s, 6H); 1.88(m, 2H); 2.13–2.60 (m, 2H); 2.34 (s, 6H); 2.70 (m, 2H); 3.34 (m, 2H); 3.65 (m, 1H); 6.72 (m, 3); 6.85 (m, 1H); 7.00–7.60(m, 7H); 11.16 (br.s, 1H).

MS(ES$^+$) m/z (M+H)$^+$5.58

Example 15

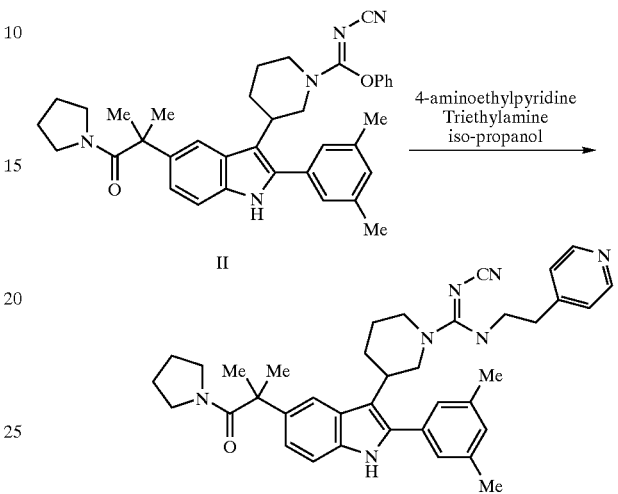

Example 15

By a method analogous to Example 14, Example 15 was prepared from Intermediate II (see Example 14) using 4-aminoethylpyridine instead of 3-(4-pyridyl-pyrrolidine).

$^1$H NMR (d-6-DMSO, δ values) 1.32–1.53 (m, 6H); 1.49 (s, 6H); 1.53–1.89(m, 4H); 2.00–2.20 (m, 1H); 2.33 (s, 6H); 2.70 (m, 2H); 2.80 (t, 2H); 2.90–3.08 (m, 2H); 3.26–3.47 (m, 3H); 3.55 (m, 2H); 3.94(m, 1H); 4.15 (m, 1H); 6.87 (d, 1H); 7.02 (s, 1H); 7.13–7.33 (m, 3H); 7.49 (s, 1H); 8.40(d, 2H); 11.12 (br.s, 1H).

MS(ES$^+$) m/z (M+H)$^+$616.20

Example 16

Example 16 was prepared from Intermediate MM using a method analogous to the preparation of Example 14.

NMR (400 Mz, 373° K, DMSO-d6): δ 1.54 (m, 10H), 1.97 (m, 1H), 2.30 (m, 1H), 2.52 (s, 6H), 3.08 (broard s, 4H), 3.19 (t, 2H), 3.42 (m, 2H), 3.55 (m, 3H), 3.63 (m, 1H), 3.70 (m, 1H), 6.71 (t, 1H), 6.97 (d of d, 1H), 7.26 (d of d, 2H), 7.32 (s, 2H), 7.35 (d, 1H), 7.54 (d, 1H), 8.51 (d of d, 2H), 10.98 (s, 1H).

Mass: ES+ (M+E)=603

Preparation of Intermediate MM

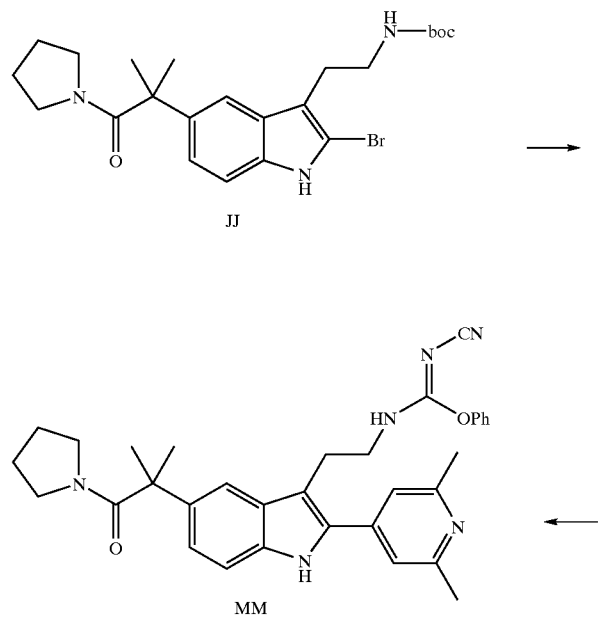

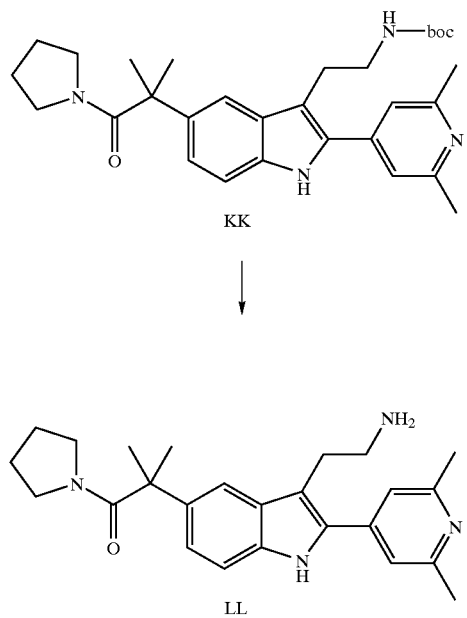

Intermediate JJ was prepared using a method analogous to the preparation of Intermediate NN (see Example 17).

NMR (300 Mz, DMSO-d6): δ 1.28 (broad s, 2H), 1.36 (s, 9H), 1.47 (s, 6H), 1.58 (m, 2H), 2.63 (t, 2H), 2.72 (t, 2H), 3.07 (q, 2H), 3.35 (m, 2H), 6.88 (m, 2H), 7.21 (d, 1H), 7.34 (s, 1H), 11.60 (s, 1H).

Mass: ES− (M−H)=476/478

A mixture of Intermediate JJ (1.43 g, 3.0 mM), 2,6-dimethyl-4-trimethylstannane (890 mg, 3.3 mM), and Pd$_2$(dba)$_3$ (173 mg, 0.15 mM) in toluene (30 ml) under nitrogen was heated under reflux for 3 hr. Additional stannane and catalyst (as above) were added and reflux was continued for a further 9 hr. The solvent was evaporated and Intermediate KK was isolated by MPLC (70–100% ethyl acetate/isohexane gradient) and triturated with ether.

Yield=760 mg, 50%.

NMR (300 Mz, CDCl$_3$): δ 1.37 (s, 9H), 1.52 (m, 2H), 1.65 (m, 8H), 2.60 (s, 6H), 2.77 (t, 2H), 3.12 (t, 2H), 3.48 (m, 2H), 3.55 (t, 2H), 4.67 (t, 1H), 7.11 (d, 1H), 7.24 (s, 2H), 7.33 (d, 1H), 7.48 (s, 1H), 8.36 (s, 1H).

Mass: ES+ (M+H)=505.

Intermediate KK. (750 mg, 1.49 mM) was dissolved in TFA (5 ml) and the solution was heated briefly to 50° C. The TFA was evaporated and the residue was dissolved in ethyl acetate. Excess sat. HCl/ethyl acetate was added giving a white precipitate of Intermediate LL as a 2HCl salt. This was filtered off, washed with ethyl acetate and ether and dried under hi-vac.

Yield=616 mg, (87%)

NMR (300 Mz, DMSO-d6): δ 1.44 (m, 2H), 1.50 (s, 6H), 1.59 (m, 2H), 2.69 (m, 2H), 2.79 (s, 6H), 3.00 (m, 2H), 3.44 (m, 4H+water), 7.07 (d, 1H), 7.45 (d, 1H), 7.60 (s, 2H), 7.92 (s, 2H), 8.3 (broad s, 3H)

Mass: ES− (M−H)=403

Intermediate LL ease prepared using a method analogous to the preparation of Intermediate LL (see Example 1).

Mass: ES+ (M+H)=549

Example 17

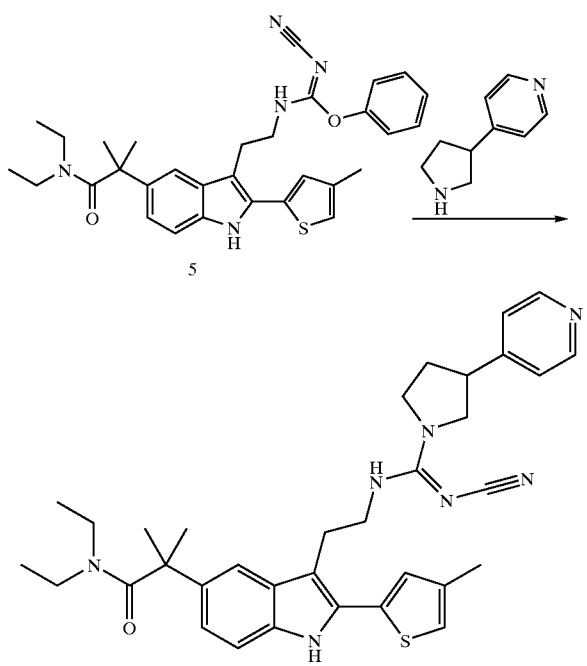

Example 17

Phenyl N'-cyano-N-{2-[5-[2-(diethylamino)-1,1-dimethyl-2-oxoethyl]-2-(4-methylthien-2-yl)-1H-indol-3-yl]ethyl}imidocarbamate (5), 124 mg(0.23 mmol) and 4-pyrrolidin-3-yl pyridine, 170 mg(1.15 mmol) in 2-propanol (2 ml) were refluxed for 24 hr then a further 150 mg amine added and reflux continued for a further 24 hr. The resulting solution was then purified by chromatography on silica (Bond Elut, 20 g), using increasing concentrations (1–6%) of methanol in dichloromethane eluent, to give the Example 17, 52 mg(38%) as a pale orange solid.

$^1$H-NMR (300 MHz, CDCl$_3$): δ=0.75 (m, 3H), 1.16 (m, 3H), 1.58 (s, 6H), 1.95 (m, 1H), 2.22–2.40 (m, 1H), 2.30 (s, 3H), 2.92 (m, 2H), 3.20–3.62 (m, 8H), 3.65–3.84 (m, 3H), 4.60 (t, 1H), 6.88 (s, 1H), 7.02–7.14 (m, 3H), 7.16 (s, 1H), 7.31 (d, 1H), 7.40 (s, 1H), 8.45 (s, 1H), 8.54 (d, 2H).

MS: ESP$^+$ (M+H)$^+$=596.

Preparation of Intermediate RR raphy (Merck 9385 silica, 40% ethyl acetate in iso-hexane eluent) to give Intermediate PP, 234 mg(91%), as a pale orange gum.

MS: ESP$^+$ (M+H)$^+$=498.

tert-butyl 2-[5-[2-(diethylamino)-1,1-dimethyl]-2-oxoethyl]-2-(4-methylthien-2yl)-1H-indol-3-yl]ethylcarbamate (Intermediate PP), 246 mg(0.49 mmol), in ethanol (3 ml) was treated, at room temperature, with a saturated solution of hydrogen chloride in ethanol (3 ml) then the reaction stirred 48 hr. The solvent was then evaporated in vacuo to give Intermediate QQ as a pale green solid which was triturated with diethyl ether, filtered and dried. Yield 130 mg(61%).

$^1$H-NMR (300 MHz, DMSO-d6): δ=0.65 (m, 3H), 1.07 (m, 3H), 1.48 (s, 6H), 2.30 (s, 3H), 2.80–3.00 (m, 4H), 3.15–3.30 (m, 4H), 6.93 (dd, 1H), 7.23 (d, 1H), 7.32 (d, 1H), 7.35 (s, 1H), 7.43 (d, 1H), 8.14(broad s, 3H).

MS: ESP$^+$ (M+H)$^+$=398.

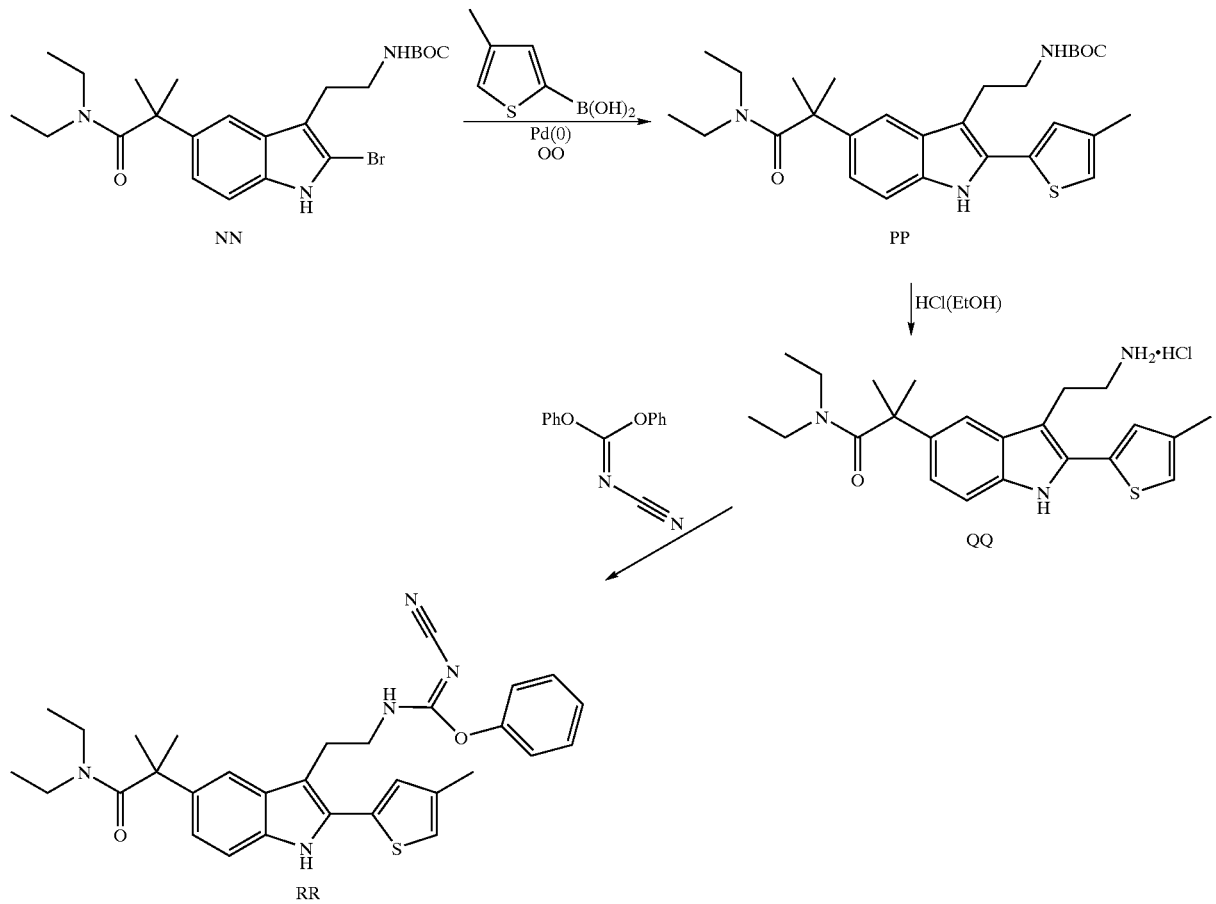

A mixture of tert-butyl 2-{2-bromo-5-[2-(diethylamino)-1,1-dimethyl-2-oxoethyl]-1H-indol-3-yl}ethylcarbamate (Intermediate NN), 240 mg(0.5 mmol), 4-methylthiophene-2-boronic acid (Intermediate OO), 100 mg (0.7 mmol) and tetrakis(triphenylphosphine)palladium(0), 28 mg(5 mol %) in a mixture of 1,2-dimethoxyethane (5 ml) and a saturated aqueous solution of sodium hydrogen carbonate (1.6 ml) were refluxed for 5 hr. then quenched in water and extracted with tert-butyl methylether. The extract was washed with water and saturated brine, dried over magnesium sulfate and evaporated to an orange gum. Purified by flash chromatog- 2-[3-(2-aminoethyl)-2-(4-methylthien-2-yl)-1H-indol-5-yl]-N,N-diethyl-2-methylpropanamide Intermediate QQ (hydrochloride salt), 100 mg(0.23 mmol), diphenyl cyanocarbonimidate, 58 mg(0.24 mmol) and triethylamine, 23 mg(0.23 mmol) in 2-propanol (5 ml) were stirred at room temperature for 8 hr then left to stand overnight. The resulting solution was purified by flash chromatography (Merck 9385 silica, 70% ethyl acetate in iso-hexane eluent) to give Intermediate RR, 124 mg(99%), as a colourless gum.

MS: ESP$^+$ (M+H)$^+$=542.

Preparation of Intermediate NN

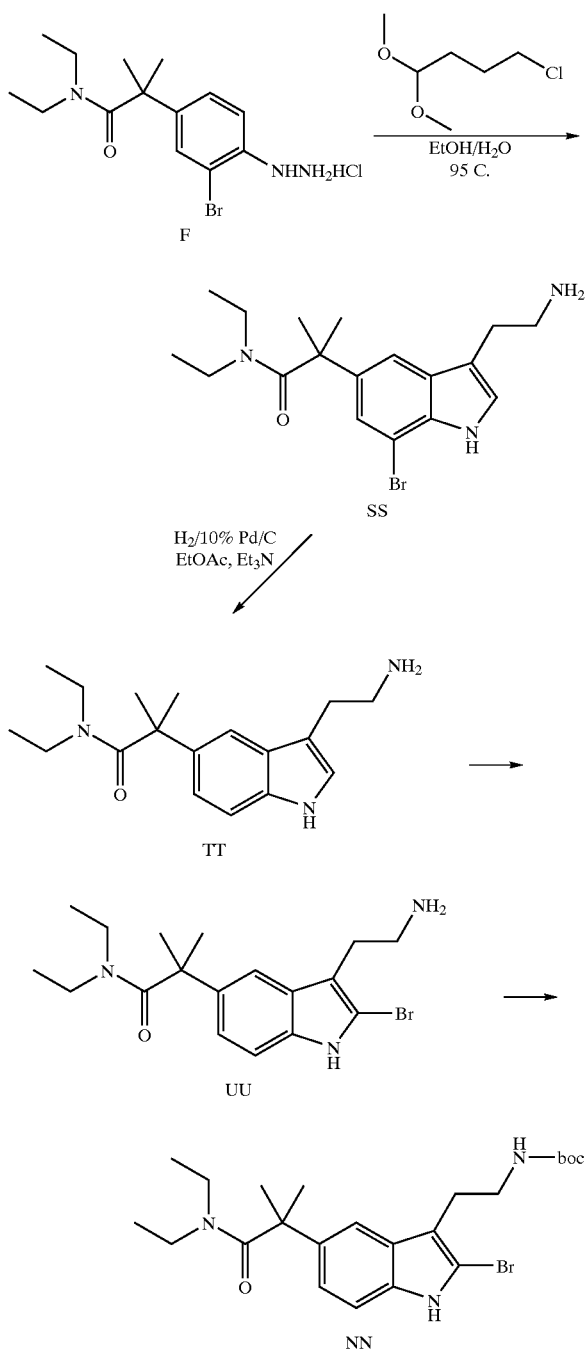

A solution of Intermediate F (see Example 1) (7.2 g, 20 mmol) and 4-Chlorobutyraldehyde dimethyl acetal (2.64 g, 20 mmol) in EtOH (200 mL) and water (40 mL) was heated at 95° C. for 18 hrs. The RM was concentrated and the residues treated with satd NaHCO3 (aq) to give Intermediate SS as a yellow solid which was collected by filtration and dried. 2.0 g (26.5%)

$^1$H NMR (300 MHz, CDCl$_3$) δ0.6–0.8 (m,3H); 1.04–1.2 (m,3H); 1.5–1.7 (bs,8H); 2.8–2.94 (m,4H); 2.95–3.03 (m,2H); 3.26–3.42 (m,2H); 7.1 (s,1H); 7.22 (s,1H); 7.35 (s, 1H); 8.48 (bs,1H).

MS (ES$^+$) m/z (M)$^+$380.13

Intermediate SS (6.0 g,15.8 mmol) was reduced analogously as for the preparation of Intermediate J (see Example 1) to give Intermediate TT as a brown foam, 3.8 g (80%).

$^1$H NMR (300 MHz, CDCl$_3$) δ0.63 (m,3H); 1.10 (m,3H); 1.52 (s,6H); 1.6 (bs,2H); 2.83 (m,4H); 2.95 (t,2H); 3.3 (m,2H); 6.97 (d,1H); 6.98 (dd,1H); 7.23 (d,1H); 7.35 (s,1H); 8.1 (bs,$_1$H).

MS (ES$^+$) m/z (M+H)$^+$302

To a stirred solution of Intermediate TT (3.01 g, 10 mM) in acetic acid (40 ml), was added 5.5M HBr/acetic acid (1.82 ml, 10 mM), followed by 2.0M bromine/acetic acid (5.5 ml, 11.0 mM). The solvent was evaporated under reduced pressure and the residue (Intermediate UU) was taken into ethyl acetate. It was washed with aq. ammonia and brine, dried over anh. sodium sulphate and evaporated to a gum. This was not characterised and was used without purification.

To a solution of Intermediate UU (3.33 mM) in dichloromethane (10 ml) was added Boc-O-Boc (5.0 mM, 1.09 g) and the solution was stirred for 30 mins. The solution was evaporated to ~5 ml and applied directly to a MPLC column, eluting with 40% ethyl acetate/isohexane. Intermediate NN was isolated as a crisp foam on evaporation.

Yield=895 mg, 56% (2 stages).

NMR (300 Mz, DMSO-d6) δ0.56 (broad s, 3H), 1.00 (broad s, 3H), 1.35 (s, 9H), 1.45 (s, 6H), 2.70 (t, 2H), 2.80 (broad s, 2H), 3.07 (q, 2H), 3.20 (broad s, 2H), 6.82 (m, 1H), 6.86 (d of d, 1H), 7.20 (d, 1H), 7.30 (s, 1H), 11.53 (s, 1H).

Mass: ES– (M–H)=480

Therapeutic Uses

Compounds of formula I are provided as medicaments for antagonising gonadotropin releasing hormone (GnRH) activity in a patient, eg, in men and/or women. To this end, a compound of formula I can be provided as part of a pharmaceutical formulation which also includes a pharmaceutically acceptable diluent or carrier (eg, water). The formulation may be in the form of tablets, capsules, granules, powders, syrups, emulsions (eg, lipid emulsions), suppositories, ointments, creams, drops, suspensions (eg, aqueous or oily suspensions) or solutions (eg, aqueous or oily solutions). If desired, the formulation may include one or more additional substances independently selected from stabilising agents, wetting agents, emulsifying agents, buffers, lactose, sialic acid, magnesium stearate, terra alba, sucrose, corn starch, talc, gelatin, agar, pectin, peanut oil, olive oil, cacao butter and ethylene glycol.

The compound is preferably orally administered to a patient, but other routes of administration are possible, such as parenteral or rectal administration. For intravenous, subcutaneous or intramuscular administration, the patient may receive a daily dose of 0.1 mgkg$^{-1}$ to 30 mgkg$^{-1}$ (preferably, 5 mgkg$^{-1}$ to 20 mgkg$^{-1}$) of the compound, the compound being administered 1 to 4 times per day. The intravenous, subcutaneous and intramuscular dose may be given by means of a bolus injection. Alternatively, the intravenous dose may be given by continuous infusion over a period of time. Alternatively, the patient may receive a daily oral dose which is approximately equivalent to the daily parenteral dose, the composition being administered 1 to 4 times per day. A suitable pharmaceutical formulation is one suitable for oral administration in unit dosage form, for example as a tablet or capsule, which contains between 10 mg and 1 g (preferably, 100 mg and 1 g) of the compound of the invention.

The following illustrate representative pharmaceutical dosage forms containing a compound of the invention, or a pharmaceutically acceptable salt or solvate thereof (hereafter referred to as "compound X"), for use in humans.

(a)

| Tablet I | mg/tablet |
| --- | --- |
| Compound X. | 100 |
| Lactose Ph.Eur. | 179 |
| Croscarmellose sodium | 12.0 |
| Polyvinylpyrrolidone | 6 |
| Magnesium stearate | 3.0 |

(b)

| Tablet II | mg/tablet |
| --- | --- |
| Compound X | 50 |
| Lactose Ph.Eur. | 229 |
| Croscarmellose sodium | 12.0 |
| Polyvinylpyrrolidone | 6 |
| Magnesium stearate | 3.0 |

(c)

| Tablet III | mg/tablet |
| --- | --- |
| Compound X | 1.0 |
| Lactose Ph.Eur. | 92 |
| Croscarmellose sodium | 4.0 |
| Polyvinylpyrrolidone | 2.0 |
| Magnesium stearate | 1.0 |

(d)

| Capsule | mg/capsule |
| --- | --- |
| Compound X | 10 |
| Lactose Ph.Eur. | 389 |
| Croscarmellose sodium | 100 |
| Magnesium stearate | 1. |

(e)

| Injection I | (50 mg/ml) |
| --- | --- |
| Compound X | 5.0% w/v |
| Isotonic aqueous solution | to 100% |

Buffers, pharmaceutically acceptable cosolvents (eg, polyethylene glycol, propylene glycol, glycerol or EtOH) or complexing agents such as hydroxy-propyl β cyclodextrin may be used to aid formulation.

One aspect of the invention relates to the use of compounds according to the invention for reducing the secretion of LH and/or FSH by the pituitary gland of a patient. In this respect, the reduction may be by way of a reduction in biosynthesis of the LH and FSH and/or a reduction in the release of LH and FSH by the pituitary gland. Thus, compounds according to the invention can be used for therapeutically treating and/or preventing a sex hormone related condition in the patient. By "preventing" we mean reducing the patient's risk of contracting the condition. By "treating" we mean eradicating the condition or reducing its severity in the patient. Examples of sex hormone related conditions are: a sex hormone dependent cancer, benign prostatic hypertrophy, myoma of the uterus, endometriosis, polycystic ovarian disease, uterine fibroids, prostatauxe, myoma uteri, hirsutism and precocious puberty. Examples of sex hormone dependent cancers are: prostatic cancer, uterine cancer, breast cancer and pituitary gonadotrophe adenoma.

Assays

The ability of compounds according to the invention to act as antagonists of GnRH can be determined using the following in vitro assays.

Binding Assay Using Rat Pituitary GnRH Receptor

The assay is performed as follows:
1. Incubate crude plasma membranes prepared from rat pituitary tissues in a Tris.HCl buffer (pH. 7.5, 50 mM) containing bovine serum albumin (0.1%), [I-125]D-t-Bu-Ser6-Pro9-ethyl amide-GnRH, and the test compound. Incubation is at 4° C. for 90 minutes to 2 hours.
2. Rapidly filter and repeatedly wash through a glass fibre filter.
3. Determine the radioactivity of membrane bound radio-ligands using a gamma counter.

From this data, the $IC_{50}$ of the test compound can be determined as the concentration of the compound required to inhibit radio-ligand binding to GnRH receptors by 50%. Compounds according to the present invention have activity at a concentration from 1 nM to 5 $\mu$M.

Binding Assay Using Human GnRH Receptor

Crude membranes prepared from CHO cells expressing human GnRH receptors are sources for the GnRH receptor. The binding activity of compounds according to the invention can be determined as an $IC_{50}$ which is the compound concentration required to inhibit the specific binding of [$^{125}$I]buserelin to GnRH receptors by 50%. [$^{125}$I]Buserelin (a peptide GnRH analogue) is used here as a radiolabelled ligand of the receptor.

Assay to Determine Inhibition of LH Release

The LH release assay can be used to demonstrate antagonist activity of compounds, as demonstrated by a reduction in GnRH-induced LH release.

Preparation of Pituitary Glands

Pituitary glands obtained from rats are prepared as follows. Suitable rats are Wistar male rats (150–200 g) which have been maintained at a constant temperature (eg, 25° C.) on a 12 hour light/12 hour dark cycle. The rats are sacrificed by decapitation before the pituitary glands are aseptically removed to tube containing Hank's Balanced Salt Solution (HBSS).

The glands are further processed by:
1. Centrifugation at 250×g for 5 minutes;
2. Aspiration of the HBSS solution;
3. Transfer of the glands to a petri dish before mincing with a scalpel;
4. Transfer of the minced tissue to a centrifuge tube by suspending the tissue three successive times in 10 ml aliquots of HBSS containing 0.2% collagenase and 0.2% hyaluronidase;
5. Cell dispersion by gentle stirring of the tissue suspension while the tube is kept in a water bath at 37° C.;
6. Aspiration 20 to 30 times using a pipette, undigested pituitary fragments being allowed to settle for 3 to 5 minutes;
7. Aspiration of the suspended cells followed by centrifugation at 1200×g for 5 minutes;
8. Resuspension of the cells in culture medium of DMEM containing 0.37% $NaHCO_3$, 10% horse serum, 2.5% foetal bovine serum, 1% non essential amino acids, 1% glutamine and 0.1% gentamycin;
9. Treatment of the undigested pituitary fragments 3 times with 30 ml aliquots of the collagenase and hyaluronidase.
10. Pooling of the cell suspensions and dilution to a concentration of 3×10$^5$ cells/ml;
11. Placing of 1.0 ml of this suspension in each of a 24 well tray, with the cells being maintained in a humidified 5% $CO_2$/95% air atmosphere at 37° C. for 3 to 4 days Testing of Compounds The test compound is dissolved in DMSO to a final concentration of 0.5% in the incubation medium.

1.5 hours prior to the assay, tie cells are washed three times with DMEM containing 0.37% NaHCO$_3$, 10% horse serum, 2.5% foetal bovine serum, 1% non essential amino acids (100x), 1% glutamine (100x), 1% penicillin/streptomycin (10,000 units of each per ml) and 25 mM HEPES at pH 7.4. Immediately prior to the assay, the cells are again washed twice in this medium.

Following this, 1 ml of fresh medium containing the test compound and 2 nM GnRH is added to two wells. For other test compounds (where it is desired to test more than one compound), these are added to other respective duplicate wells. Incubation is then carried out at 37° C. for three hours.

Following incubation, each well is analysed by removing the medium from the well and centrifuging the medium at 2000xg for 15 minutes to remove any cellular material. The supernatant is removed and assayed for LH content using a double antibody radio-immuno assay. Comparison with a suitable control (no test compound) is used to determine whether the test compound reduces LH release. Compounds according to the present invention have activity at a concentration from 1 nM to 5 µM,

What is claimed is:

1. A compound of formula I or a pharmaceutically acceptable salt or solvate thereof

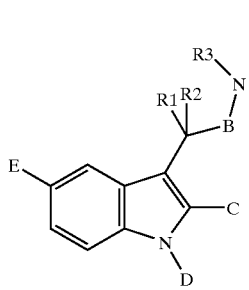

I

For A, either:
(i) A represents a single bond; optionally substituted C1 to C8 alkylene; a C2 to C12 group having at least one alkene double bond; a 3- to 8-membered heterocyclic ring containing from 1 to 4 heteroatoms independently selected from O, N and S or —R—Ar—R'—, where R and R' are independently selected from a bond, optionally substituted C1 to C8 alkylene and a C2 to C12 group having at least one alkene double bond; and Ar represents optionally substituted aryl; or (ii) the structure N—A(—R4) represents a 3- to 8-membered heterocyclic ring optionally containing from 1 to 3 further heteroatoms independently selected from O, N and S, N—A(—R4) being optionally substituted;

B represents a bond or optionally substituted C1 to C5 alkylene;

C represents a mono- or bi-cyclic aromatic ring structure optionally having at least one substituent selected from CN; NR5R6; an optionally substituted C1 to C8 alkyl; optionally substituted C1 to C8 alkoxy; halogen;

D represents hydrogen; optionally substituted C1 to C8 alkyl; or (CH$_2$)$_b$—R, wherein R represents C3 to C8 cycloalkyl;

E is selected from an optionally substituted 3- to 8-membered heterocyclic ring containing from 1 to 4 heteroatoms independently selected from O, N and S; II; III; IV; V; VI and VII

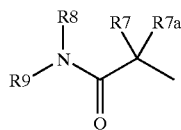

II

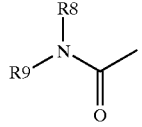

III

IV

V

VI

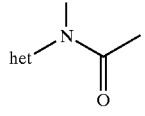

VII

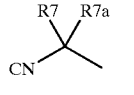

VIIa

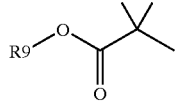

VIIb

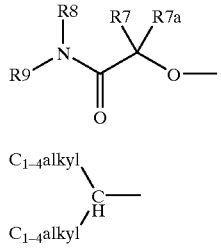

VIIc

VIId wherein het represents an optionally substituted 3- to 8-membered heterocyclic ring containing from 1 to 4 heteroatoms independently selected from O, N and S;

F is optionally substituted and represents phenyl or a 3- to 8-membered heterocyclic ring containing from 1 to 4 heteroatoms independently selected from O, N and S;

For X and Y, either:
(iii) X represents N and Y represents CN or H; or X represents CH and Y represents NO$_2$; or
(iv) X—Y represents O;

For R1 and R2; either:
(v) R1 and R2 are independently selected from hydrogen and optionally substituted C1 to C8 alkyl; or
(vi) R1 and R2 together represent carbonyl; or (vii)

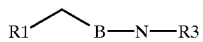

represents an optionally substituted 3- to 8-membered heterocyclic ring containing from 1 to 3 further heteroatoms independently selected from O, N and S, and R2 meets the definition in option (v);

R3 meets the definition in option (vii) or represents hydrogen or optionally substituted C1 to C8 alkyl;

R4 meets the definition in option (ii) or represents hydrogen or optionally substituted C1 to C8 alkyl;

R5 and R6 are independently selected from H; optionally substituted C1 to C8 alkyl and optionally substituted aryl;

For R7 and R7a, either:

(viii) R7 and R7a are independently selected from H or optionally substituted C1 to C8 alkyl; or (ix)

represents an optionally substituted 3 to 7-membered cycloalkyl ring;

For R8 and R9; either:

(x) R8 is selected from H; optionally substituted C1 to C8 alkyl; optionally substituted aryl; R—Ar, where R represents C1 to C8 alkylene and Ar represents optionally substituted aryl; and an optionally substituted 3- to 8-membered heterocyclic ring optionally containing from 1 to 3 further heteroatoms independently selected from O, N and S; and R9 is selected from H; optionally substituted C1 to C8 alkyl and optionally substituted aryl; or (xi) wherein E represents structure II or III, NR8(-R9) represents an optionally substituted 3- to 8-membered heterocyclic ring optionally containing from 1 to 3 further heteroatoms independently selected from O, N and S; or (xii) wherein E represents structure VI,

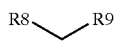

represents an optionally substituted 3- to 8-membered heterocyclic ring optionally containing from 1 to 4 heteroatoms independently selected from O, N and S;

b represents zero or an integer from 1 to 6.

2. The compound of claim 1, wherein F is optionally substituted and represents pyridyl, VIII, IX, X, XI, XII, XIII, XIV or XIVa

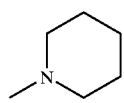

VIII

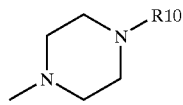

IX

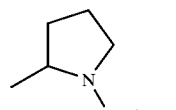

X

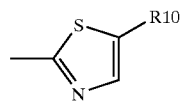

XI

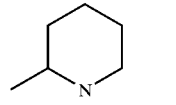

XII

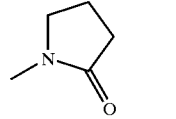

XIII

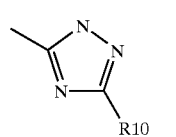

XIV

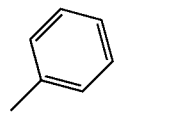

XIVa wherein
R10 represents hydrogen; optionally substituted C1 to C8 alkyl; OH; halogen; CN; C1 to C8 alkoxy; or CF$_3$; and
R10' represents hydrogen or optionally substituted C1 to C8 alkyl.

3. The compound of claim 1 or 2, wherein, E represents one of the following groups

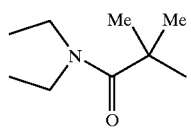 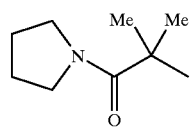

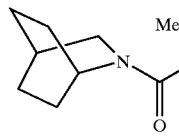 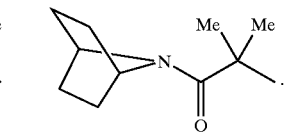

4. The compound of any preceding claim, wherein C represents

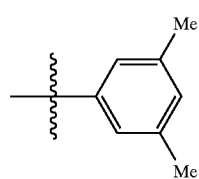

wherein Me represents methyl.

5. The compound of any preceding claim, wherein X represents CH and Y represents NO$_2$.

6. The compound of any one of claims 1 to 4, wherein X represents N and Y represents CN.

7. The compound of any one of claims 1 to 4, wherein X and Y represent O.

8. The compound of any preceding claim, wherein R1 and R2 each represent H and B represents C1 alkylene.

9. The compound of claim 1, wherein the compound is selected from 2-(2-(3,5-dimethylphenyl)-3-{2-[(2-nitro-1-{[2-(4-pyridinyl)ethyl]amino}ethenyl)amino]ethyl}-1H-indol-5-yl)-N,N-diethyl-2-methylpropanamide;

2-[3-2{-[((cyanoimino){[2-(4-pyridinyl)ethyl[amino}methyl)amino]ethyl}-2-(3,5-2-[3-2{-[((cyanoimino){[2-(2-pyridinyl)ethyl]amino}methyl)amino]ethyl}-2-(3,5-dimethylphenyl)-1H-indol-5yl]-N,N-diethyl-2-methylpropanamide;

2-[3-2{-[((cyanoimino){[2-(1-imidazoyl)ethyl]amino}methyl)amino]ethyl}-2-(3,5-dimethylphenyl)-1H-indol-5yl]-N,N-diethyl-2-methylpropanamide;

2-[2-(3,5-dimethylphenyl)-3-(2-{[(phenethylamino)carbonyl]amino}ethyl)-1H-indol-5-yl]-N,N-diethyl-2-methylpropanamide;

2-[2-(3,5-dimethylphenyl)-3-(2-{[[(4-pyridinyl)ethyl]amino)carbonyl]amino}ethyl)-1H-indol-5-yl]-N,N-diethyl-2-methylpropanamide;

2-[3-2{-[((cyanoimino){[3-(4-methylpiperazino)propyl]amino}methyl)amino]ethyl}-2-(3,5-dimethylphenyl)-1H-indol-5-yl]-N,N-diethyl-2-methylpropanamide;

2-[3-2{-[((cyanoimino){[2-(2-piperidinyl)ethyl]amino}methyl)amino]ethyl)-2-(3,5-dimethylphenyl)-1H-indol-5-yl]-N,N-diethyl-2-methylpropanamide;

2-[3-2-({(cyanoimino)[3-(4-pyridinyl)-pyrrolidin-1-yl]methy}lamino)ethyl]-2-(3,5-dimethylphenyl)-1H-indol-5-yl]N,N-diethy-1-2-methylpropanamide;

2-[3-2{-[((cyanoimino){[2-(4-pyridinyl)ethyl]aminomethyl}methyl)amino]ethyl}-2-(3,5-dimethylphenyl)-1H-indol-5-yl]-N,N-diethyl-2-methylpropanamide;

2-[3-[2(2-nitro-1-([3-(4-pyridinyl)-pyrrolidin-1-yl]ethenyl}amino)ethyl]-2-(3,5-dimethylphenyl)-1H-indol-5-yl]-N,N-diethyl-2-methylpropanamide;

2-[3-[2-((carbonyl)[3-(4-pyridinyl)-pyrrolidin-1-yl]amino)ethyl]-2-(3,5-dimethylphenyl)-1H-indol-5-yl]-N,N-diethyl-2-methylpropanamide;

2-[3-[2-({(imino)[3-(4-pyridinyl)-pyrrolidin-1-yl]methyl}amino)ethyl]-2-(3,5-dimethylphenyl)-1H-indol-5-yl]-N,N-diethyl-2-methylpropanamide; and 2-[3-[2-({(cyanoimino)[3-(4-pyridinyl)-pyrrolidin-1-yl]methyl}amino)ethyl]-2-(3,5-dimethylphenyl)-1H-indol-5-yl]-1-cyclopropylcarboxylic acid-diethylamide.

10. A pharmaceutical formulation comprising a compound according to any one of claims 1 to 9 and a pharmaceutically acceptable diluent or carrier.

11. A method for reducing the secretion of luteinising hormone by the pituitary gland of a patient, comprising administering a compound according to any one of claims 1 to 9.

12. A method of antagonising gonadotropin releasing hormone activity in a patient, comprising administering to the patient a compound according to any one of claims 1 to 9.

13. A process of producing a compound according to any one of claims 1 to 9, wherein the process comprises a reaction step selected from steps (a) to (e):

(a) Reaction of XV as follows

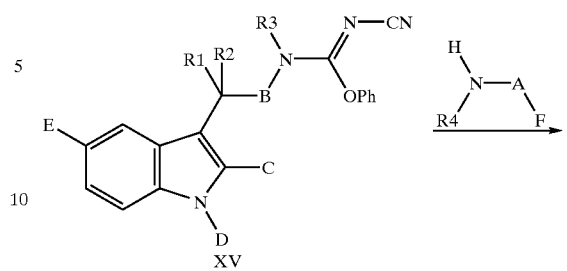

XV

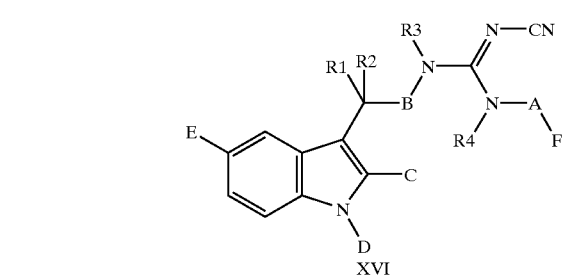

XVI (b) Cleavage of the CN group of XVI in the presence of acid to produce XVII

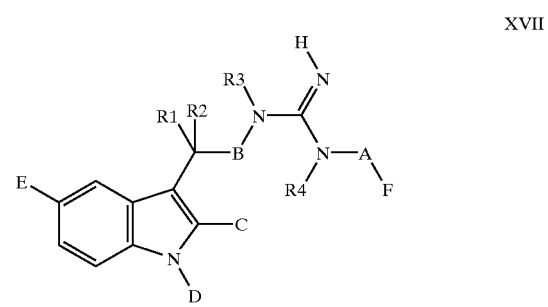

XVII (c) Reaction of XVIII as follows

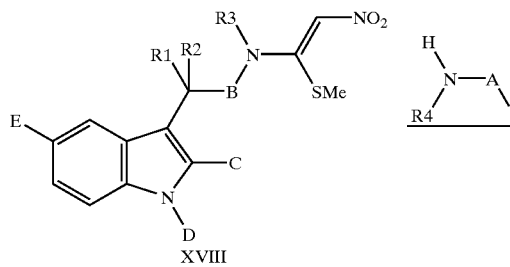

XVIII

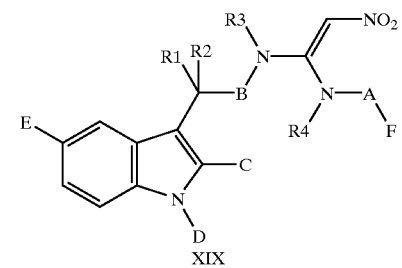

XIX (d) Reaction of XX as follows
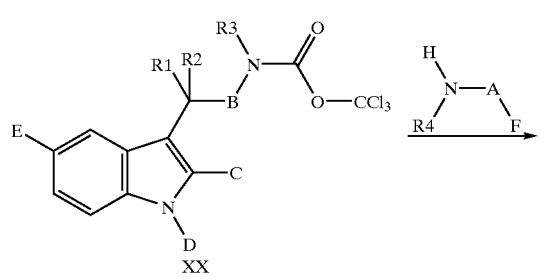
(e) Reaction of XXII as follows
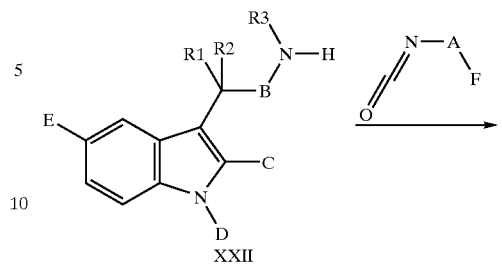
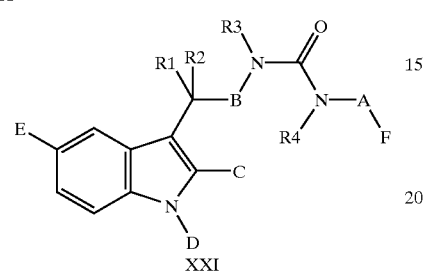
XXI
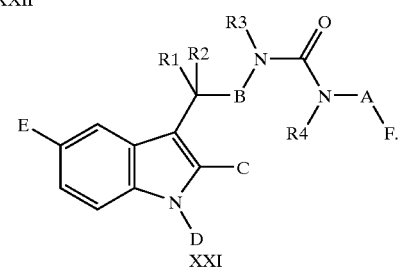
XXI
* * * * *

UNITED STATES PATENT AND TRADEMARK OFFICE
CERTIFICATE OF CORRECTION

PATENT NO. : 6,809,098 B2  
APPLICATION NO. : 10/227193  
DATED : October 26, 2004  
INVENTOR(S) : Michael Wardleworth et al.

It is certified that error appears in the above-identified patent and that said Letters Patent is hereby corrected as shown below:

On the Title Page:

Col. 1, insert item --(30) Foreign Application Priority Data

Feb. 20, 2001            (SE) ..........................................0100566-9--;

In the Specification:

Col. 2, line 29, delete "is";

Col. 14, line 50, delete

" 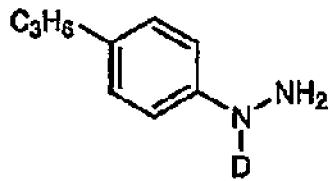 " and instead insert -- 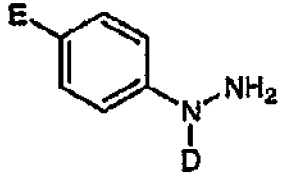 --

Col. 19, after line 9, delete

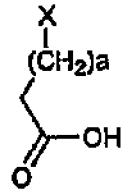 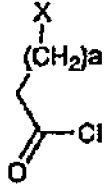

"X = Cl, Br, I" and instead insert --X = Cl, Br, I --

UNITED STATES PATENT AND TRADEMARK OFFICE
CERTIFICATE OF CORRECTION

PATENT NO. : 6,809,098 B2
APPLICATION NO. : 10/227193
DATED : October 26, 2004
INVENTOR(S) : Michael Wardleworth et al.

It is certified that error appears in the above-identified patent and that said Letters Patent is hereby corrected as shown below:

Col. 25, before line 60, delete

"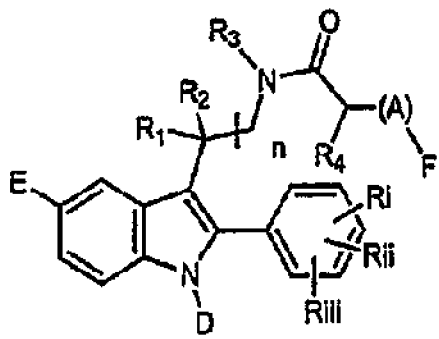" and instead insert

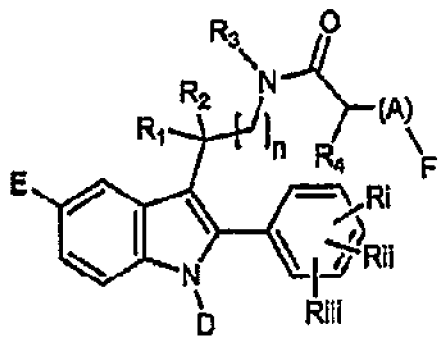

--

Col. 32, line 10, after "100%)" delete "p" and insert a new paragraph before "A solution";

Col. 32, line 44, delete "(M+M)" and instead insert --(M+H)--;21, delete "(s,1);" and instead insert --(s,1H);--;

UNITED STATES PATENT AND TRADEMARK OFFICE
CERTIFICATE OF CORRECTION

| | |
|---|---|
| PATENT NO. | : 6,809,098 B2 |
| APPLICATION NO. | : 10/227193 |
| DATED | : October 26, 2004 |
| INVENTOR(S) | : Michael Wardleworth et al. |

It is certified that error appears in the above-identified patent and that said Letters Patent is hereby corrected as shown below:

In the claims:

Claim 9, Col. 93, line 19, delete "5yl" and instead insert --5-yl--; and

Claim 9, Col. 93, line 31, please delete "ethyl)" and instead insert --ethyl}--.

Signed and Sealed this

Sixth Day of March, 2007

JON W. DUDAS
*Director of the United States Patent and Trademark Office*